(12) United States Patent
Voelkel et al.

(10) Patent No.: US 11,098,132 B2
(45) Date of Patent: Aug. 24, 2021

(54) ANTI-FACTOR IX PADUA ANTIBODIES

(71) Applicant: TAKEDA PHARMACEUTICAL COMPANY LIMITED, Osaka (JP)

(72) Inventors: Dirk Voelkel, Vienna (AT); Robert Pachlinger, Vienna (AT); Hanspeter Rottensteiner, Vienna (AT); Alfred Weber, Vienna (AT); Andrea Engelmaier, Vienna (AT)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 99 days.

(21) Appl. No.: 16/301,962

(22) PCT Filed: May 16, 2017

(86) PCT No.: PCT/US2017/032808
§ 371 (c)(1),
(2) Date: Nov. 15, 2018

(87) PCT Pub. No.: WO2017/200981
PCT Pub. Date: Nov. 23, 2017

(65) Prior Publication Data
US 2019/0194351 A1 Jun. 27, 2019

Related U.S. Application Data

(60) Provisional application No. 62/340,834, filed on May 24, 2016, provisional application No. 62/337,118, filed on May 16, 2016.

(51) Int. Cl.
| | |
|---|---|
| *C07K 16/36* | (2006.01) |
| *G01N 33/573* | (2006.01) |
| *C07K 16/00* | (2006.01) |
| *G01N 33/86* | (2006.01) |

(52) U.S. Cl.
CPC ............ *C07K 16/36* (2013.01); *C07K 16/005* (2013.01); *G01N 33/573* (2013.01); *G01N 33/86* (2013.01); *C07K 2317/21* (2013.01); *C07K 2317/33* (2013.01); *C07K 2317/34* (2013.01); *C07K 2317/35* (2013.01); *C07K 2317/55* (2013.01); *C07K 2317/76* (2013.01); *C07K 2317/92* (2013.01); *C07K 2319/21* (2013.01); *C07K 2319/43* (2013.01); *G01N 2333/9645* (2013.01)

(58) Field of Classification Search
None
See application file for complete search history.

(56) References Cited

U.S. PATENT DOCUMENTS

| | | | | |
|---|---|---|---|---|
| 6,180,370 B1 * | 1/2001 | Queen | ................ | C07K 16/2866 435/69.6 |
| 7,279,161 B2 | 10/2007 | Scheiflinger et al. | | |
| 7,297,336 B2 * | 11/2007 | Kerschbaumer | ....... | C07K 16/36 424/146.1 |
| 2010/0003254 A1 * | 1/2010 | Hattori | ..................... | A61P 7/02 424/136.1 |

FOREIGN PATENT DOCUMENTS

| | | |
|---|---|---|
| EP | 2881463 | 6/2015 |
| RU | 2002109586 | 3/2004 |
| WO | 2015086406 | 6/2015 |
| WO | 2016/004113 | 1/2016 |

OTHER PUBLICATIONS

Lescar, Julien, et al. "Crystal structure of a cross-reaction complex between Fab F9. 13.7 and guinea fowl lysozyme." Journal of Biological Chemistry 270.30 (1995): 18067-18076 (Year: 1995).*
Sela-Culang, Inbal, Vered Kunik, and Yanay Ofran. "The structural basis of antibody-antigen recognition." Frontiers in immunology 4 (2013): 302 (Year: 2013).*
Janeway, Charles A. "Immunobiology: The Immune System in Health and Disease." (2005) (Year: 2005).*
Sedrak, Peter, Kelvin Hsu, and Chandra Mohan. "Molecular signatures of anti-nuclear antibodies—contribution of heavy chain framework residues." Molecular immunology 40.8 (2003): 491-499. (Year: 2003).*
Davies, David R., and Susan Chacko. "Antibody structure." Accounts of chemical research 26.8 (1993): 421-427. (Year: 1993).*
Xiang, Jim, et al. "Framework residues 71 and 93 of the chimeric B72. 3 antibody are major determinants of the conformation of heavy-chain hypervariable loops." (1995): 385-390. (Year: 1995).*
Kipriyanov, Sergey M., and Fabrice Le Gall. "Generation and production of engineered antibodies." Molecular biotechnology 26.1 (2004): 39-60. (Year: 2004).*
Janeway, A. C., et al. "Immunobiology: the immune system in health and disease. London." Current Biology (1997): 3:1-3:11. (Year: 1997).*
Russian Office Action and Search Report issued Jul. 14, 2020 in connection with RU Patent Application No. 2018138782.
International Search Report dated Nov. 13, 2017 for PCT/US17/32808.
Simioni et al., "X-Linked Thrombophilia with a Mutant Factor IX (Factor IX Padua)", New England Journal of Medicine, vol. 361, No. 17, Oct. 22, 2009, pp. 1671-1675.
Finn et al., "The efficacy and the risk of immunogenicity of FIX Padua (R338L) in hemophilia B dogs treated by AAV muscle gene therapy", Blood, vol. 120, No. 23, Nov. 29, 2012, pp. 4521-4523.
Crudele et al., "AAV liver expression of FIX-Padua prevents and eradicates FIX inhibitor without increasing thrombogenicity in hemophilia B dogs and mice", Blood, vol. 125, No. 10, Mar. 1, 2015, pp. 1553-1561, retrieved from https://ww.ncbi.nlm.nih.gov/pmc/articles/PMC4351503.

* cited by examiner

Primary Examiner — Michael Szperka
Assistant Examiner — Lia E Taylor
(74) Attorney, Agent, or Firm — Troutman Pepper Hamilton Sanders LLP

(57) ABSTRACT

Provided herein are anti-Factor IX Padua binding constructs, e.g., antibodies and antigen-binding fragments thereof. Related polypeptides, conjugates and kits are also provided. The inventions may be used in methods of detecting Factor IX Padua in a sample.

52 Claims, 32 Drawing Sheets
Specification includes a Sequence Listing.

FIX-WT: SIGNAL PEPTIDE    PROPEPTIDE    LIGHT CHAIN

MQRVNMIMAESPGLITICLLGYLLSAECTVFLDHENANKILNRPKRYNSGKLEEFVQGNLERECMEEK
CSFEEAREVFENTERTTEFWKQYVDGDQCESNPCLNGGSCKDDINSYECWCPFGFEGKNCELDVTCNI
KNGRCEQFCKNSADNKVVCSCTEGYRLAENQKSCEPAVPFPCGRVSVSQTSKLTRAETVFPDVDYVNS
TEAETILDNITQSTQSFNDFTRVVGGEDAKPGQFPWQVVLNGKVDAFCGGSIVNEKWIVTAAHCVETG
VKITVVAGEHNIEETEHTEQKRNVIRIIPHHNYNAAINKYNHDIALLELDEPLVLNSYVTPICIADKE
YTNIFLKFGSGYVSGWGRVFHKGRSALVLQYLRVPLVDRATCLRSTKFTIYNNMFCAGFHEGGRDSCQ
GDSGGPHVTEVEGTSFLTGIISWGEECAMKGKYGIYTKVSRYVNWIKEKTKLT (ACTIVATION PEPTIDE / HEAVY CHAIN)

FIX-PADUA:

MQRVNMIMAESPGLITICLLGYLLSAECTVFLDHENANKILNRPKRYNSGKLEEFVQGNLERECMEEK
CSFEEAREVFENTERTTEFWKQYVDGDQCESNPCLNGGSCKDDINSYECWCPFGFEGKNCELDVTCNI
KNGRCEQFCKNSADNKVVCSCTEGYRLAENQKSCEPAVPFPCGRVSVSQTSKLTRAETVFPDVDYVNS
TEAETILDNITQSTQSFNDFTRVVGGEDAKPGQFPWQVVLNGKVDAFCGGSIVNEKWIVTAAHCVETG
VKITVVAGEHNIEETEHTEQKRNVIRIIPHHNYNAAINKYNHDIALLELDEPLVLNSYVTPICIADKE
YTNIFLKFGSGYVSGWGRVFHKGRSALVLQYLRVPLVDRATCLLSTKFTIYNNMFCAGFHEGGRDSCQ
GDSGGPHVTEVEGTSFLTGIISWGEECAMKGKYGIYTKVSRYVNWIKEKTKLT

*PADUA MUTANT:*

REPLACEMENT OF THE AMINO ACID ARGININE (R) TO LEUCINE (L) AT POSITION 384 LEADS TO A HYPERFUNCTIONAL FIX ACTIVITY (~5-10X). POSITION 384 IS POSITION 338 OF THE MATURE PEPTIDE SEQUENCE WHICH EXCLUDES SIGNAL PEPTIDE AND PROPEPTIDE.

FIGURE 1

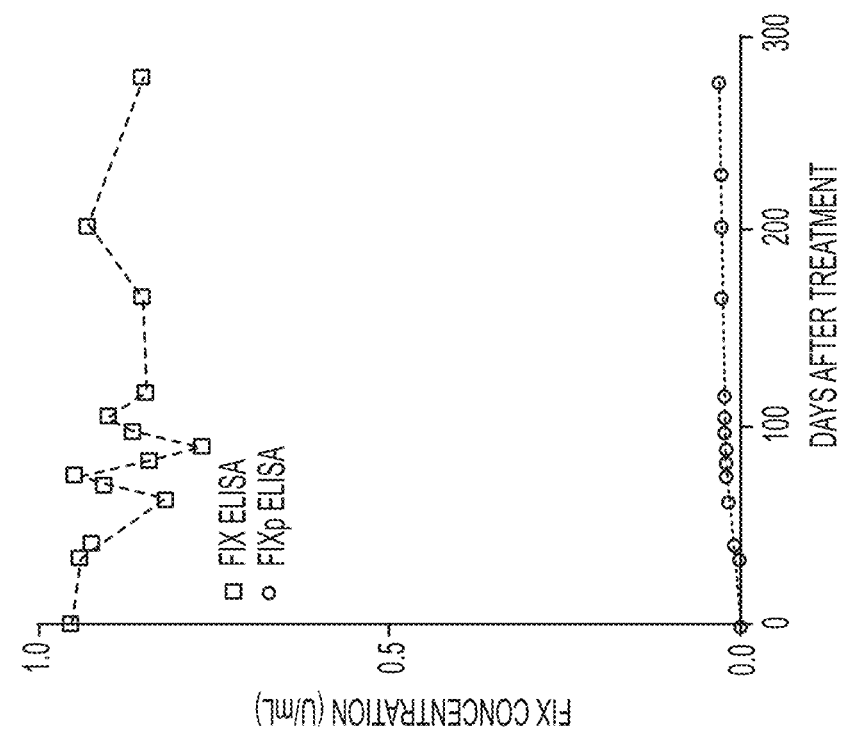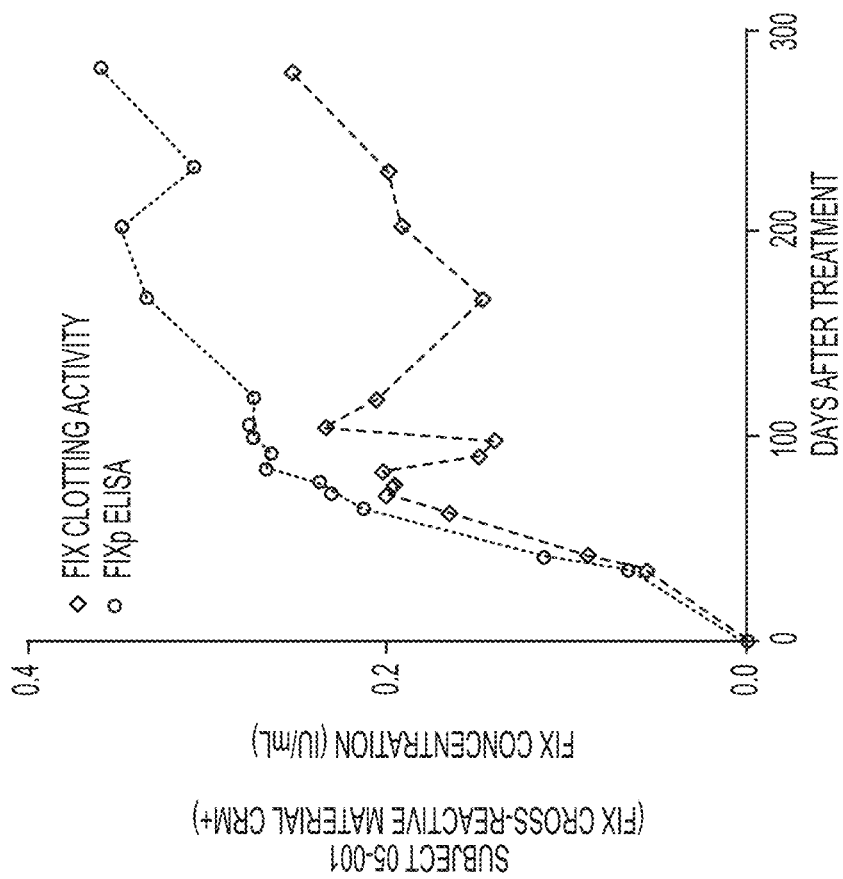
FIGURE 30

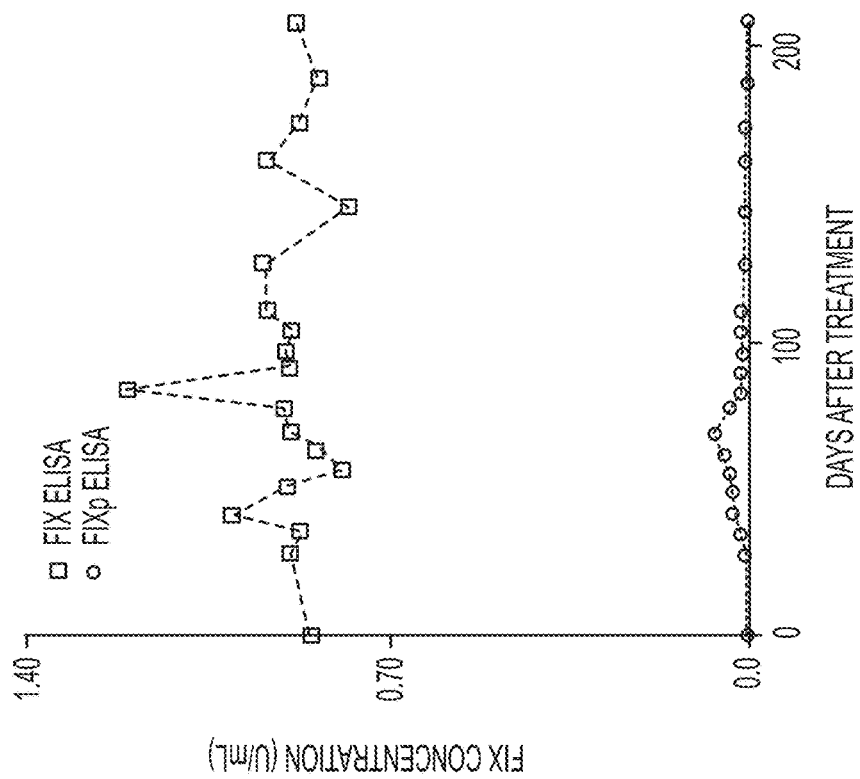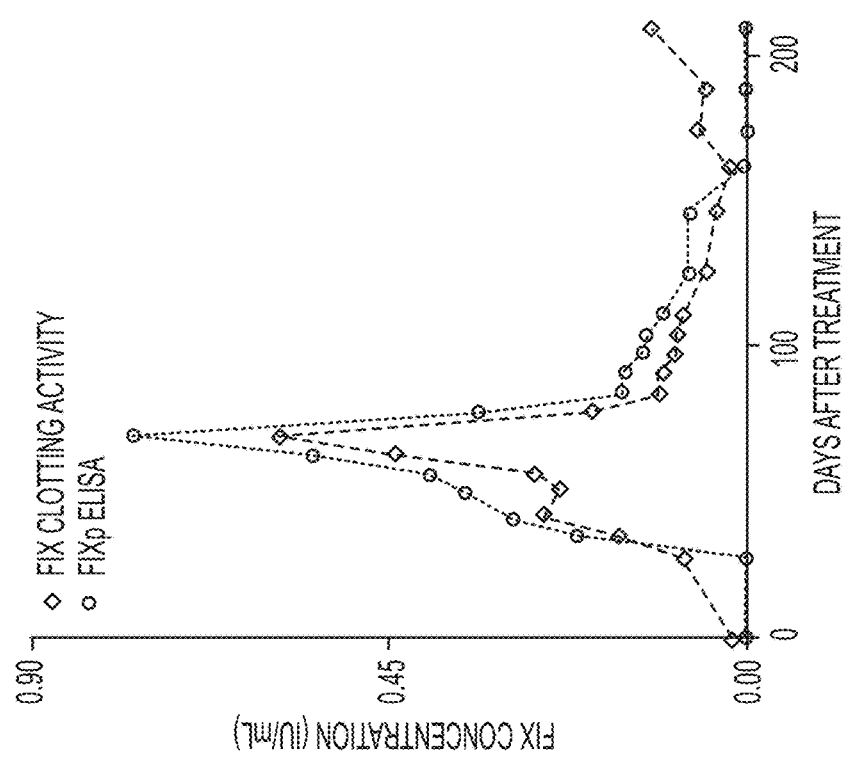
FIGURE 31

SEQUENCE LISTING

```
<160> NUMBER OF SEQ ID NOS: 28

<210> SEQ ID NO 1
<211> LENGTH: 461
<212> TYPE: PRT
<213> ORGANISM: Homo sapiens

<400> SEQUENCE: 1

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
```

```
            260                 265                 270
Val Lys Ile Thr Val Ala Gly Glu His Asn Ile Glu Glu Thr Glu
        275                 280                 285

His Thr Glu Gln Lys Arg Asn Val Ile Arg Ile Ile Pro His His Asn
        290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
                340                 345                 350

Val Ser Gly Trp Gly Arg Val Phe His Lys Gly Arg Ser Ala Leu Val
                355                 360                 365

Leu Gln Tyr Leu Arg Val Pro Leu Val Asp Arg Ala Thr Cys Leu Arg
                370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
                420                 425                 430

Glu Glu Cys Ala Met Lys Gly Lys Tyr Gly Ile Tyr Thr Lys Val Ser
                435                 440                 445

Arg Tyr Val Asn Trp Ile Lys Glu Lys Thr Lys Leu Thr
                450                 455                 460

<210> SEQ ID NO 2
<211> LENGTH: 461
<212> TYPE: PRT
<213> ORGANISM: Homo sapiens

<400> SEQUENCE: 2

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
                100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
        130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175
```

```
Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
            210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
            245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
            275                 280                 285

His Thr Glu Gln Lys Arg Asn Val Ile Arg Ile Ile Pro His His Asn
            290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
            325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Leu
370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
            405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr
450                 455                 460

<210> SEQ ID NO 3
<211> LENGTH: 12
<212> TYPE: PRT
<213> ORGANISM: Homo sapiens

<400> SEQUENCE: 3

Asp Arg Ala Thr Cys Leu Leu Ser Thr Lys Phe Thr
1               5                   10

<210> SEQ ID NO 4
<211> LENGTH: 26
<212> TYPE: PRT
<213> ORGANISM: Homo sapiens

<400> SEQUENCE: 4

Leu Val Asp Arg Ala Thr Cys Leu Leu Ser Thr Lys Phe Thr Ile Tyr
1               5                   10                  15

Asn Asn Met Phe Cys Ala Gly Phe His Glu
            20                  25
```

<210> SEQ ID NO 5
<211> LENGTH: 25
<212> TYPE: PRT
<213> ORGANISM: Homo sapiens

<400> SEQUENCE: 5

Leu Val Asp Arg Ala Thr Cys Leu Leu Ser Thr Lys Phe Thr Ile Tyr
1               5                   10                  15

Asn Asn Met Phe Cys Ala Gly Phe His
            20                  25

<210> SEQ ID NO 6
<211> LENGTH: 6
<212> TYPE: PRT
<213> ORGANISM: Homo sapiens

<400> SEQUENCE: 6

Ser Ser Tyr Ala Ile Ser
1               5

<210> SEQ ID NO 7
<211> LENGTH: 17
<212> TYPE: PRT
<213> ORGANISM: Homo sapiens

<400> SEQUENCE: 7

Gly Ile Val Pro Ala Phe Gly Thr Ala Asn Tyr Ala Gln Lys Phe Gln
1               5                   10                  15

Gly

<210> SEQ ID NO 8
<211> LENGTH: 9
<212> TYPE: PRT
<213> ORGANISM: Homo sapiens

<400> SEQUENCE: 8

Ser Trp Gly Val Ile Ser Phe Ala Tyr
1               5

<210> SEQ ID NO 9
<211> LENGTH: 11
<212> TYPE: PRT
<213> ORGANISM: Homo sapiens

<400> SEQUENCE: 9

Arg Ala Ser Gln Asp Ile Ser Ser Tyr Leu Asn
1               5                   10

<210> SEQ ID NO 10
<211> LENGTH: 7
<212> TYPE: PRT
<213> ORGANISM: Homo sapiens

<400> SEQUENCE: 10

Ala Ala Ser Asn Leu Gln Ser
1               5

<210> SEQ ID NO 11
<211> LENGTH: 10
<212> TYPE: PRT
<213> ORGANISM: Homo sapiens

<400> SEQUENCE: 11

Met Gln Tyr Asp Ser Leu Pro Phe Thr Phe
1               5                   10

<210> SEQ ID NO 12
<211> LENGTH: 8
<212> TYPE: PRT
<213> ORGANISM: Homo sapiens

<400> SEQUENCE: 12

Asp Tyr Lys Asp Asp Asp Asp Lys
1               5

<210> SEQ ID NO 13
<211> LENGTH: 6
<212> TYPE: PRT
<213> ORGANISM: Homo sapiens

<400> SEQUENCE: 13

His His His His His His
1               5

<210> SEQ ID NO 14
<211> LENGTH: 12
<212> TYPE: PRT
<213> ORGANISM: Homo sapiens

<400> SEQUENCE: 14

Asp Arg Ala Thr Cys Leu Arg Ser Thr Lys Phe Thr
1               5                   10

<210> SEQ ID NO 15
<211> LENGTH: 25
<212> TYPE: PRT
<213> ORGANISM: Homo sapiens

<400> SEQUENCE: 15

Leu Val Asp Arg Ala Thr Cys Leu Arg Ser Thr Lys Phe Thr Ile Tyr
1               5                   10                  15

Asn Asn Met Phe Cys Ala Gly Phe His
                20                  25

<210> SEQ ID NO 16
<211> LENGTH: 622
<212> TYPE: PRT
<213> ORGANISM: Homo sapiens
<300> PUBLICATION INFORMATION:
<308> DATABASE ACCESSION NUMBER: GenBank / AAH51332.1
<309> DATABASE ENTRY DATE: 2006-07-15
<313> RELEVANT RESIDUES IN SEQ ID NO: (1)..(622)

<400> SEQUENCE: 16

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
                20                  25                  30

Gln Ala Arg Ser Leu Leu Gln Arg Val Arg Arg Ala Asn Thr Phe Leu
            35                  40                  45

Glu Glu Val Arg Lys Gly Asn Leu Glu Arg Glu Cys Val Glu Glu Thr
        50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

```
Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
            115                 120                 125

Cys Gln Leu Trp Arg Ser Arg Tyr Pro His Lys Pro Glu Ile Asn Ser
            130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                    165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
            195                 200                 205

Pro Leu Glu Gln Cys Val Pro Asp Arg Gly Gln Gln Tyr Gln Gly Arg
            210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                    245                 250                 255

Leu Val Glu Asn Phe Cys Arg Asn Pro Asp Gly Asp Glu Glu Gly Ala
            260                 265                 270

Trp Cys Tyr Val Ala Gly Lys Pro Gly Asp Phe Gly Tyr Cys Asp Leu
            275                 280                 285

Asn Tyr Cys Glu Glu Ala Val Glu Glu Thr Gly Asp Gly Leu Asp
            290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                    325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
            355                 360                 365

Asp Ala Glu Ile Gly Met Ser Pro Trp Gln Val Met Leu Phe Arg Lys
370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                    405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
            435                 440                 445

Ile His Pro Arg Tyr Asn Trp Arg Glu Asn Leu Asp Arg Asp Ile Ala
            450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                    485                 490                 495

Tyr Lys Gly Arg Val Thr Gly Trp Gly Asn Leu Lys Glu Thr Trp Thr
            500                 505                 510
```

Ala Asn Val Gly Lys Gly Gln Pro Ser Val Leu Gln Val Asn Leu
            515                 520                 525

Pro Ile Val Glu Arg Pro Val Cys Lys Asp Ser Thr Arg Ile Arg Ile
530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
    610                 615                 620

<210> SEQ ID NO 17
<211> LENGTH: 467
<212> TYPE: PRT
<213> ORGANISM: Homo sapiens
<300> PUBLICATION INFORMATION:
<308> DATABASE ACCESSION NUMBER: PRF / 1205236A
<309> DATABASE ENTRY DATE: 1996-10-18
<313> RELEVANT RESIDUES IN SEQ ID NO: (1)..(467)

<400> SEQUENCE: 17

Leu Leu Gly Glu Ser Leu Phe Ile Arg Arg Glu Gln Ala Asn Asn Ile
1               5                   10                  15

Leu Ala Arg Val Thr Arg Ala Asn Ser Phe Leu Glu Glu Met Lys Lys
            20                  25                  30

Gly His Leu Glu Arg Glu Cys Met Glu Glu Thr Cys Ser Tyr Glu Glu
        35                  40                  45

Ala Arg Glu Val Phe Glu Asp Ser Asp Lys Thr Asn Glu Phe Trp Asn
    50                  55                  60

Lys Tyr Lys Asp Gly Asp Gln Cys Glu Thr Ser Pro Cys Gln Asn Gln
65                  70                  75                  80

Gly Lys Cys Lys Asp Gly Leu Gly Glu Tyr Thr Cys Thr Cys Leu Glu
                85                  90                  95

Gly Phe Glu Gly Lys Asn Cys Glu Leu Phe Thr Arg Lys Leu Cys Ser
            100                 105                 110

Leu Asp Asn Gly Asp Cys Asp Gln Phe Cys His Glu Glu Gln Asn Ser
        115                 120                 125

Val Val Cys Ser Cys Ala Arg Gly Tyr Thr Leu Ala Asp Asn Gly Lys
    130                 135                 140

Ala Cys Ile Pro Thr Gly Pro Tyr Pro Cys Gly Lys Gln Thr Leu Glu
145                 150                 155                 160

Arg Arg Lys Arg Ser Val Ala Gln Ala Thr Ser Ser Ser Gly Glu Ala
                165                 170                 175

Pro Asp Ser Ile Thr Trp Lys Pro Tyr Asp Ala Ala Asp Leu Asp Pro
            180                 185                 190

Thr Glu Asn Pro Phe Asp Leu Leu Asp Phe Asn Gln Thr Gln Pro Glu
        195                 200                 205

Arg Gly Asp Asn Asn Leu Thr Arg Ile Val Gly Gly Gln Glu Cys Lys
    210                 215                 220

Asp Gly Glu Cys Pro Trp Gln Ala Leu Leu Ile Asn Glu Glu Asn Glu
225                 230                 235                 240

Gly Phe Cys Gly Gly Thr Ile Leu Ser Glu Phe Tyr Ile Leu Thr Ala

-continued

```
                245                 250                 255
Ala His Cys Leu Tyr Gln Ala Lys Arg Phe Glu Gly Asp Arg Asn Thr
            260                 265                 270
Glu Gln Glu Glu Gly Gly Glu Ala Val His Glu Val Glu Val Val Ile
            275                 280                 285
Lys His Asn Arg Phe Thr Lys Glu Thr Tyr Asp Phe Asp Ile Ala Val
            290                 295                 300
Leu Arg Leu Lys Thr Pro Ile Thr Phe Arg Met Asn Val Ala Pro Ala
305                 310                 315                 320
Cys Leu Pro Glu Arg Asp Trp Ala Glu Ser Thr Leu Met Thr Gln Lys
                325                 330                 335
Thr Gly Ile Val Ser Gly Phe Gly Arg Thr His Glu Lys Gly Arg Gln
            340                 345                 350
Ser Thr Arg Leu Lys Met Leu Glu Val Pro Tyr Val Asp Arg Asn Ser
            355                 360                 365
Cys Lys Leu Ser Ser Ser Phe Ile Ile Thr Gln Asn Met Phe Cys Ala
            370                 375                 380
Gly Tyr Asp Thr Lys Gln Glu Asp Ala Cys Gln Gly Asp Ser Gly Gly
385                 390                 395                 400
Pro His Val Thr Arg Phe Lys Asp Thr Tyr Phe Val Thr Gly Ile Val
                405                 410                 415
Ser Trp Gly Glu Gly Cys Ala Arg Lys Gly Lys Tyr Gly Ile Tyr Thr
            420                 425                 430
Lys Val Thr Ala Phe Leu Lys Trp Ile Asp Arg Ser Met Lys Thr Arg
            435                 440                 445
Gly Leu Pro Lys Ala Lys Ser His Ala Pro Glu Val Ile Thr Ser Ser
            450                 455                 460
Pro Leu Lys
465
```

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24
<211> LENGTH: 118
<212> TYPE: PRT
<213> ORGANISM: Homo sapiens

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Val Pro Ala Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Gly Val Ile Ser Phe Ala Tyr Trp Gly Gln Gly Thr
            100                 105                 110

Leu Val Thr Val Ser Ser
        115

<210> SEQ ID NO 25
<211> LENGTH: 109
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Met Gln Tyr Asp Ser Leu Pro Phe
                85                  90                  95

Thr Phe Gly Gln Gly Thr Lys Val Glu Ile Lys Arg Thr
            100                 105

<210> SEQ ID NO 26
<211> LENGTH: 220
<212> TYPE: PRT
<213> ORGANISM: Homo sapiens

<400> SEQUENCE: 26

Gln Val Gln Leu Val Gln Ser Gly Ala Glu Val Lys Lys Pro Gly Ser
1               5                   10                  15

```
Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Val Pro Ala Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Gly Val Ile Ser Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser
210                 215                 220

<210> SEQ ID NO 27
<211> LENGTH: 214
<212> TYPE: PRT
<213> ORGANISM: Homo sapiens

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Met Gln Tyr Asp Ser Leu Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Ala
            210

<210> SEQ ID NO 28
<211> LENGTH: 290
<212> TYPE: PRT
<213> ORGANISM: Homo sapiens

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Val Pro Ala Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Gly Val Ile Ser Phe Ala Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Glu Phe Pro Lys
        210                 215                 220

Pro Ser Thr Pro Pro Gly Ser Ser Gly Glu Leu Glu Glu Leu Leu Lys
225                 230                 235                 240

His Leu Lys Glu Leu Leu Lys Gly Pro Arg Lys Gly Glu Leu Glu Glu
                245                 250                 255

Leu Leu Lys His Leu Lys Glu Leu Leu Lys Gly Gly Ser Gly Gly Ala
            260                 265                 270

Pro Asp Tyr Lys Asp Asp Asp Lys Asp Ala Pro His His His His
            275                 280                 285

His His
290
```

ANTI-FACTOR IX PADUA ANTIBODIES

CROSS REFERENCE TO RELATED APPLICATIONS

This patent application is a U.S. National Phase Application under 35 U.S.C. § 371 of International Patent Application No. PCT/US2017/032808, filed May 16, 2017 and published on Nov. 23, 2017 as International Publication No. WO 2017/200981A1, which claims priority pursuant to 35 U.S.C. § 119(e) to U. S. Provisional Patent Applications Nos. 62/337,118, filed May 16, 2016 and 62/340,834, filed May 24, 2016. The entire contents of these applications are hereby incorporated by reference in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 28,804 byte ACII (Text) file named "50573_SeqListing.txt"; created on May 16, 2016.

BACKGROUND

Gene therapy holds great promise as a future treatment option for hemophilia. In one clinical trial, subjects with severe hemophilia B are treated with an adeno-associated viral (AAV) vector encoding Factor IX (FIX) Padua, a hyper-functional variant of FIX with a single amino acid substitution of Leu for the Arg at position 338 of the mature peptide sequence (or position 384 of the preproprotein sequence). Specific detection of the transgene product (FIX Padua) would be useful for assessing the success of factor replacement. However, specific detection of FIX Padua in treated patients remains a challenge, as some patients have Factor IX cross-reactive material (CRM). Some CRM-positive (CRM+) patients express, for example, wild-type (WT) Factor IX, which cross-reacts with currently available FIX Padua-binding agents, thus making it difficult to determine if FIX Padua is expressed by such CRM+ patients.

SUMMARY

Provided herein are binding constructs which specifically recognize FIX Padua (FIXp) without cross-reactivity to wild-type FIX. In exemplary embodiments, the binding construct is an antibody or an antigen-binding fragment thereof that binds FIX Padua comprising the amino acid sequence of SEQ ID NO: 1 and does not bind to a WT Factor IX comprising the amino acid sequence SEQ ID NO: 2. In exemplary embodiments, the binding construct is a polypeptide comprising an amino acid sequence comprising each of SEQ ID NOs: 6-11, optionally, wherein (i) one or more amino acids are present between each of SEQ ID NOs: 6-11, and/or (ii) the polypeptide optionally further comprises a FLAG tag comprising DYKDDDDK (SEQ ID NO: 12) and/or a hexa-His tag comprising HHHHHH (SEQ ID NO: 13), optionally, wherein the FLAG tag and/or the hexa-His tag are located at the C-terminal end of the polypeptide. In exemplary embodiments, the binding construct is a conjugate comprising an antigen-binding fragment as described herein conjugated to (i) a constant region of an immunoglobulin heavy chain, (ii) a constant region of an immunoglobulin light chain, or (iii) both a constant region of an immunoglobulin heavy chain and a constant region of an immunoglobulin light chain. In exemplary embodiments, the binding construct is a conjugate comprising an antibody or antigen-binding fragment as described herein linked or conjugated to a heterologous moiety. In exemplary aspects, the conjugate comprises an antibody or antigen-binding fragment as described herein conjugated to a polymer, a carbohydrate, a lipid, a nucleic acid, an oligonucleotide, an amino acid, peptide, polypeptide, protein, or a detecting agent.

Nucleic acids comprising a nucleotide sequence encoding the antibody, antigen-binding fragment, polypeptide, conjugate, or a fragment thereof, as described herein, are additionally provided. Vectors comprising the nucleic acid and host cells comprising the nucleic acid or vector are further provided.

Also provided herein are related kits. In exemplary embodiments, the kit comprises an antibody, antigen-binding fragment, polypeptide, conjugate, nucleic acid, vector, host cell, as described herein, or a combination thereof, and, optionally, instructions for use. In exemplary aspects, the kit also comprises a solid support and optionally, the antibody, antigen-binding fragment, polypeptide, or conjugate is pre-coated on the solid support. In exemplary aspects, the kit also comprises a secondary antibody which binds to the antibody, antigen-binding fragment, polypeptide, or conjugate provided in the kit.

The invention further provides compositions comprising an antibody or antigen-binding fragment or polypeptide or conjugate, as described herein, admixed with a biological sample, e.g., a biological sample obtained from a human. In exemplary aspects, the biological sample comprises human plasma, or a diluted fraction thereof, and/or human tissue, or cells thereof. In exemplary aspects, the biological sample comprises human plasma proteins, wherein at least one of the human plasma proteins is selected from the group consisting of Factor IX, Factor II, and Factor X, and variants thereof. Optionally, the composition comprises a detecting agent.

Such binding constructs provided herein are useful in, e.g., detection methods that allow for unambiguous or specific detection of FIX Padua in samples, e.g., clinical or preclinical samples comprising, e.g., wild-type FIX. Accordingly, provided herein are methods of detecting Factor IX Padua comprising the amino acid sequence of SEQ ID NO: 1 in a sample obtained from a subject. In exemplary embodiments, the method comprises (i) contacting the sample with a binding construct (e.g., an antibody, antigen-binding fragment, polypeptide or conjugate, as described herein) to form a complex, e.g., an immunocomplex, comprising the FIXp and the binding construct, and (ii) detecting the complex in the sample.

BRIEF DESCRIPTION OF THE DRAWINGS

FIG. 1 represents a schematic of the amino acid sequences of WT Factor IX (SEQ ID NO: 2) and of FIX Padua (SEQ ID NO: 1).

FIG. 22 represents a graph of an ELISA from purified bivalent Fabs against wt and Padua antigens. Bivalent Fabs, obtained from different panning strategies were tested for specificity against wt and Padua peptide and protein. Results are represented as fold increase over background (FIG. 22A), and (FIG. 22B) shows the scheme of the ELISA set up. The order of the columns is the same as in the legend (i.e., Ab42 column is to the left). For details, see the methods description in Example 5.

FIG. 23 represents a graph of an ELISA of purified bivalent Fabs in the presence of 20% plasma. (FIG. 23A) Purified bivalent Fabs were coated and incubated with 20% human plasma containing 5 μg/mL FIX wt and the denoted Padua FIX concentrations. Detection was performed with an HRP labeled polyclonal goat anti FIX antibody (100 ng/ml). (FIG. 23B) Scheme of ELISA set up. The lines are in the same order as the legend.

(FIG. 24A) His-tagged mini antibody Ab42 binds FIX Padua with a KD=59 nM (ka: $4.3 \times 10^4$ 1/Ms; kd:0.002531 1/s), (FIG. 24B) but not FIX wt on a NTA-BIAcore sensor chip. Dashed lines represent raw data, while solid lines indicated fitted data. The lines are in the same order as the legend.

FIG. 30 represents a set of graphs demonstrating the analysis of citrated plasma samples from a first patient treated with an AAV2/8 viral vector in a phase 1/2 trial. The plasma sample obtained from the first patient was FIX cross-reactive material positive (CRM+).

FIG. 31 represents a set of graphs demonstrating the analysis of citrated plasma samples from a second patient treated with an AAV2/8 viral vector in a phase 1/2 trial. The plasma sample obtained from the second patient was FIX cross-reactive material positive (CRM+).

DETAILED DESCRIPTION

Figure 2:
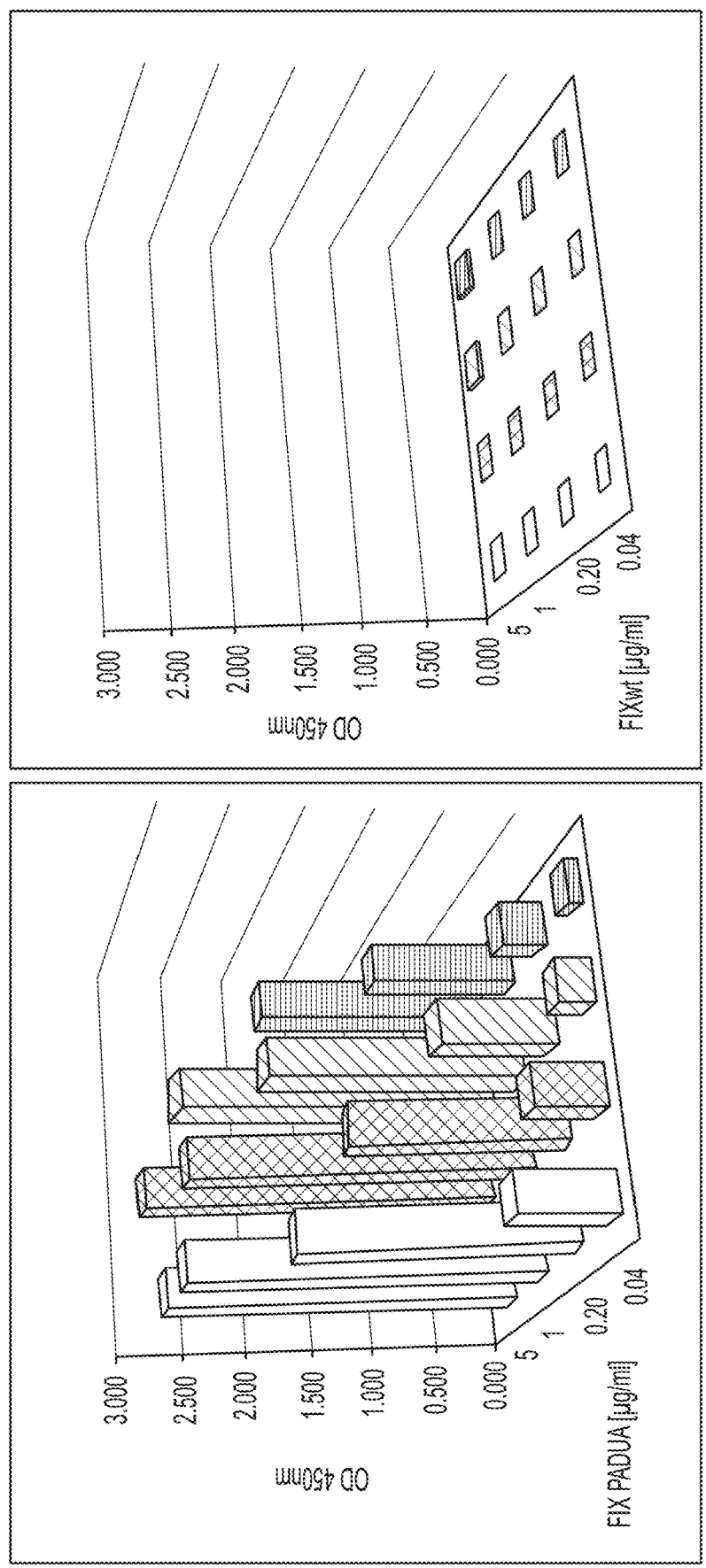
FIG. 2 represents a graph of the binding signals of FIX Padua (left panel) or WT Factor IX (right panel) to $Ni^{2+}$ plates coated with 5 µg/ml BC1 (blue bars closest to Z-axis (i.e., to the left)), 1 µg/ml BC1 (red bars right of the blue bars), 0.2 µg/ml BC1 (green bars adjacent to the red bars) or 0.04 µg/ml BC1.

Provided herein are binding constructs which specifically recognize FIX Padua with minimal or no cross-reactivity to wild-type FIX. In exemplary aspects, the binding constructs bind to FIX Padua and do not bind to wild-type (WT) Factor IX. In exemplary aspects, the binding constructs bind to FIX Padua (and not to WT Factor IX) in the presence of WT Factor IX. In exemplary aspects, the binding constructs bind to FIX Padua and do not bind to one WT Factor IX and one or both of Factor II and Factor X, or any other mutated or modified forms thereof (except FIX Padua) under similar or the same conditions. In exemplary aspects, the binding constructs bind to FIX Padua and bind to neither Factor II nor Factor X. In exemplary aspects, the binding constructs bind to FIX Padua and bind to none of WT Factor IX, Factor II and Factor X. In exemplary aspects, the binding constructs bind to FIX Padua and (not to WT Factor IX, Factor II and Factor X) in the presence of WT Factor IX, Factor II and Factor X. In exemplary embodiments, the binding constructs bind an epitope of FIX Padua (SEQ ID NO: 1) even when present in a solution comprising levels of WT Factor IX, Factor II, and Factor X which are present in human plasma.

Epitopes

By "epitope" as used herein is meant the region of or within FIX Padua which is bound by the binding construct. In some embodiments, the epitope is a linear epitope. By "linear epitope" as used herein refers to the region of or within the FIX Padua which is bound by the binding construct and which region is composed of contiguous amino acids of the amino acid sequence of the FIX Padua. The amino acids of a linear epitope are adjacent to each other in the primary structure of the Factor IX Padua. Accordingly, a linear epitope is a fragment or portion of the amino acid sequence of the antigen, i.e., FIX Padua.

In other exemplary embodiments, the epitope is a conformational or structural epitope. By "conformational epitope" or "structural epitope" is meant an epitope which is composed of amino acids which are located in close proximity to one another when the Factor IX Padua is in its properly folded state. Unlike linear epitopes, the amino acids of a conformational or structural epitope need not be adjacent to each other in the primary structure (i.e., amino acid sequence) of the FIX Padua. A conformational or structural epitope is not necessarily made of contiguous amino acids of the amino acid sequence of the antigen (FIXp).

In exemplary embodiments, the binding construct binds to an epitope of FIX Padua comprising the amino acid sequence of SEQ ID NO: 1, wherein the epitope is a linear epitope within the amino acid sequence of SEQ ID NO: 1. In exemplary aspects, the linear epitope is within the amino acid sequence of DRATCLLSTKFT (SEQ ID NO: 3). In exemplary aspects, the linear epitope comprises at least L-L of SEQ ID NO: 3. In exemplary embodiments, the binding construct binds to the linear epitope of FIX Padua even in the present of WT Factor IX, Factor II, and/or Factor X. In exemplary embodiments, the binding construct binds to the epitope of FIX Padua even in the presence of 5 µg/mL WT Factor IX. In exemplary embodiments, the binding construct binds to the epitope of FIX Padua even in the presence of 5 µg/mL WT Factor IX and in a 20% human plasma matrix.

In exemplary aspects, the binding construct does not bind to an epitope of WT FIX. In exemplary aspects, the binding construct does not bind to an epitope within SEQ ID NO: 2 or within DRATCLRSTKFT (SEQ ID NO: 14) or within LVDRATCLRSTKFTIYNNMFCAGFH (SEQ ID NO: 15). In exemplary aspects, the binding construct does not bind to an epitope of WT FIX under similar or same conditions as when the binding construct binds to FIX Padua. In exemplary aspects, the binding construct does not bind to an epitope of WT FIX when in a solution comprising normal plasma levels of WT FIX. In exemplary aspects, the binding construct does not bind to an epitope of WT FIX when in a solution (e.g., buffer) comprising 5 µg/mL WT FIX (e.g., a human plasma matrix comprising about 5 µg/mL WT FIX).

In exemplary embodiments, the binding construct binds to an epitope of FIX Padua (SEQ ID NO: 1), wherein the epitope is a conformational epitope of the folded structure of the amino acid sequence LVDRATCLL-STKFTIYNNMFCAGFH (SEQ ID NO: 5). In exemplary embodiments, the binding construct binds to an epitope of FIX Padua (SEQ ID NO: 1), wherein the epitope is a conformational epitope of the folded structure of the amino acid sequence LVDRATCLLSTKFTIYNNMFCAGFH (SEQ ID NO: 5), wherein the folded structure comprises a disulfide bridge. In exemplary embodiments, the binding construct binds to the conformational epitope of FIX Padua even in the present of WT Factor IX, Factor II, and/or Factor X. In exemplary embodiments, the binding construct binds to the epitope of FIX Padua even in the presence of 5 µg/mL WT Factor IX.

Affinity and Avidity

The binding constructs provided herein bind to FIX Padua in a non-covalent and reversible manner. In exemplary embodiments, the binding strength of the binding construct to FIX Padua may be described in terms of its affinity, a measure of the strength of interaction between the binding site of the binding construct and the epitope. In exemplary aspects, the binding constructs provided herein have high-affinity for FIX Padua and thus will bind a greater amount of FIX Padua in a shorter period of time than low-affinity binding constructs. In exemplary aspects, the binding construct has an equilibrium association constant, KA, which is at least $10^5$ mol$^{-1}$, at least $10^6$ mol$^{-1}$, at least $10^7$ mol$^{-1}$, at least $10^8$ mol$^{-1}$, at least $10^9$ mol$^{-1}$, or at least $10^{10}$ mol$^{-1}$. In exemplary aspects, the binding constructs provided herein exhibit high affinity for FIX Padua in human plasma. In exemplary aspects, the binding construct binds to the Factor IX Padua and does not bind to a WT Factor IX in a sample comprising human plasma. In exemplary aspects, the binding construct binds to the Factor IX Padua and does not bind to a WT Factor IX in a sample comprising at least or about 5% human plasma (e.g., a 5% human plasma matrix). In exemplary aspects, the binding construct binds to the Factor IX Padua and does not bind to a WT Factor IX in a sample comprising at least or about 10% human plasma (e.g., a 10% human plasma matrix). In exemplary aspects, the binding construct binds to the Factor IX Padua and does not bind to a WT Factor IX in a sample comprising at least or about 20% human plasma (e.g., a 20% human plasma matrix). In exemplary aspects, the binding construct binds to the Factor IX Padua and does not bind to a WT Factor IX in a sample comprising at least or about 5% to about 40%, about 10% to about 30%, or about 15% to about 20% human plasma. In exemplary aspects, the binding construct binds to the Factor IX Padua even when a substantial amount of WT Factor IX is present in the sample. In exemplary aspects, the binding construct binds to the Factor IX Padua and does not bind to a WT Factor IX in a sample comprising an amount of human plasma (e.g., at least or about 5% human plasma, at least or about 10% human plasma, at least or about 20% human plasma) and at least or about 1 µg/mL WT Factor IX or at least or about 2.5 µg/mL WT Factor IX or at least or about 5 µg/m L WT Factor IX or at least or about 10 µg/m L WT Factor IX. In exemplary aspects, the binding construct binds to the Factor IX Padua and does not bind to a WT Factor IX in a sample comprising other coagulation factors, including, but not limited to Factor II, Factor V, Factor VI, Factor VII, Factor VIII, Factor X, Factor XI, Factor XII, and Factor XIII. In exemplary aspects, the binding construct binds to the Factor IX Padua and does not bind to a WT Factor IX and further does not bind to Factor II or Factor X. In exemplary aspects, the binding construct binds to the Factor IX Padua and does not bind to a WT Factor IX and further binds to neither Factor II nor Factor X.

In exemplary embodiments, the binding strength of the binding construct to FIX Padua may be described in terms of its sensitivity. KD is the equilibrium dissociation constant, a ratio of $k_{off}/k_{on}$, between the binding construct and FIX Padua. KD and KA are inversely related. The KD value relates to the concentration of the binding construct (the amount of binding construct needed for a particular experiment) and so the lower the KD value (lower concentration) the higher the affinity of the binding construct. In exemplary aspects, the binding strength of the binding construct to FIX Padua may be described in terms of KD. In exemplary aspects, the KD of the binding constructs provided herein for FIXp is about $1.0 \times 10^{-6}$ or less, about $1.0 \times 10^{-7}$ or less, about $1.0 \times 10^{-8}$ or less, about $1.0 \times 10^{-9}$ or less, about $1.0 \times 10^{-10}$ or less. In exemplary aspects, the KD of the binding constructs provided herein is micromolar, nanomolar, picomolar or femtomolar. In exemplary aspects, the KD of the binding constructs provided herein is within a range of about $10^{-4}$ to $10^{-6}$ or $10^{-7}$ to $10^{-9}$ or $10^{-10}$ to $10^{-12}$ or $10^{-13}$ to $10^{-16}$. In exemplary aspects, the KD of the binding constructs provided herein is about 100 nM or less. In certain aspects, the KD of the binding constructs provided herein is about 20 nM to about 100 nM, about 25 nM to about 95 nM, about 30 nM to about 90 nM, about 35 nM to about 85 nM, about 40 nM to about 80 nM, about 45 nM to about 75 nM, about 50 nM to about 70 nM, or about 55 nM to about 65 nM. In exemplary aspects, the KD of the binding constructs is within a range of about 25 nM to about 75 nM. In exemplary aspects, the KD of the binding constructs is within a range of about 50 nM to about 60 nM. In exemplary aspects, the KD of the binding constructs is about 56 nM.

Avidity gives a measure of the overall strength of an antibody-antigen complex. It is dependent on three major parameters: affinity of the binding construct for the epitope, valency of both the binding construct and FIX Padua, and structural arrangement of the parts that interact. The greater a binding construct's valency (number of antigen binding sites), the greater the amount of antigen (FIX Padua) it can bind. In exemplary aspects, the binding constructs have a strong avidity for FIXp. In exemplary aspects, the binding constructs are multivalent. In exemplary aspects, the binding constructs are bivalent.

Structure

The binding constructs described herein may be engineered to have one of a multitude of structures. In exemplary aspects, the binding constructs provided herein have a structure of an antibody or antigen-binding fragment thereof. In exemplary aspects, the binding constructs provided herein have a structure based on or derived from an antibody. In exemplary aspects, the binding constructs provided herein have a structure of a synthetic antibody mimic, an engineered protein, or an aptamer, such as those described herein and in McEnaney et al., "Chemically Synthesized Molecules with the Targeting and Effector Functions of Antibodies" J. Am. Chem. Soc., 136 (52): 18034-18043 (2014); Binz and PlUckthun, "Engineered proteins as specific binding reagents" Curr Opin Biotechnol. 16(4):459-69 (2005); and Roque et al., "Antibodies and genetically engineered related molecules: production and purification" Biotechnol Prog. 20(3):639-54 (2004).

Antibodies and Antigen-binding Fragments

In exemplary embodiments, the binding construct is an antibody. The antibody may be any type of antibody, i.e., immunoglobulin, known in the art. In exemplary embodiments, the antibody is an antibody of class or isotype IgA, IgD, IgE, IgG, or IgM. In exemplary embodiments, the antibody described herein comprises one or more alpha, delta, epsilon, gamma, and/or mu heavy chains. In exemplary embodiments, the antibody described herein comprises one or more kappa or light chains. In exemplary aspects, the antibody is an IgG antibody and optionally is one of the four human subclasses: IgG1, IgG2, IgG3 and IgG4.

Also, the antibody in some embodiments is a monoclonal antibody. In other embodiments, the antibody is a polyclonal antibody.

In some embodiments, the antibody is structurally similar to or derived from a naturally-occurring antibody, e.g., an antibody isolated and/or purified from a mammal, e.g., mouse, rabbit, goat, horse, chicken, hamster, human, and the like. In this regard, the antibody may be considered as a mammalian antibody, e.g., a mouse antibody, rabbit antibody, goat antibody, horse antibody, chicken antibody, hamster antibody, human antibody, and the like. In exemplary aspects, the antibody comprises sequence of only mammalian antibodies. Methods of producing such antibodies are known in the art, some of which are described further herein under the section entitled "Methods of Antibody Production." In exemplary aspects, the binding construct is a fully human antibody, or does not comprise sequences of non-human antibodies.

In some embodiments, the antibody is a genetically-engineered antibody and does not occur in nature. In exemplary embodiments, the antibody is a single chain antibody, a humanized antibody, a chimeric antibody, a CDR-grafted antibody, a humaneered antibody, a bispecific antibody, a trispecific antibody, and the like. Genetic engineering techniques also provide the ability to make fully human antibodies from a non-human source.

In some aspects, the genetically-engineered antibody is a single chain antibody (SCA) specific for FIX Padua. Methods of making SCAs are known in the art. See, for example, Davis et al., Nature Biotechnology 9: 165-169 (1991).

In some aspects, the antibody is a chimeric antibody. The term "chimeric antibody" is used herein to refer to an antibody containing constant domains from one species and the variable domains from a second, or more generally, containing stretches of amino acid sequence from at least two species. In particular aspects, the chimeric antibody binds to FIX Padua.

In some aspects, the antibody is a humanized antibody. The term "humanized" when used in relation to antibodies refers to antibodies having at least CDR regions from a non-human source which are engineered to have a structure and immunological function more similar to true human antibodies than the original source antibodies. For example, humanizing can involve grafting CDR from a non-human antibody, such as a mouse antibody, into a human antibody. Humanizing also can involve select amino acid substitutions to make a non-human sequence look more like a human sequence.

Use of the terms "chimeric or humanized" herein is not meant to be mutually exclusive, and rather, is meant to encompass chimeric antibodies, humanized antibodies, and chimeric antibodies that have been further humanized. Except where context otherwise indicates, statements about (properties of, uses of, testing of, and so on) chimeric antibodies apply to humanized antibodies, and statements about humanized antibodies pertain also to chimeric antibodies. Likewise, except where context dictates, such statements also should be understood to be applicable to antibodies and antigen-binding fragments of such antibodies.

In some aspects, the antibody is a Humaneered™ antibody. Humaneering technology is a proprietary method of KaloBios Pharmaceuticals, Inc. (South San Francisco, Calif.) for converting non-human antibodies into engineered human antibodies. Humaneered™ antibodies have high affinity, and highly similar to human germ line antibody sequences. See, e.g., Tomasevic et al., Growth Factors 32: 223-235 (2014).

In some aspects, the antibody is a CDR-grafted antibody specific for FIX Padua. Methods of making CDR-grafted antibodies are known in the art. See, for example, Lo, Benny, *Antibody Engineering: Methods and Protocols*, Volume 248 (2004), which is incorporated by reference in its entirety.

In exemplary embodiments, the antibody is engineered to be bispecific, trispecific, or multi-specific, and the antibody comprises two or more distinct antigen-binding regions. In some aspects, the antibody is a bispecific or trispecific antibody specific for FIX Padua. Methods of making bispecific or trispecific antibodies are known in the art. See, for example, Marvin and Zhu, *Acta Pharmacologica Sinica* 26: 649-658 (2005) and U.S. Pat. No. 6,551,592. In exemplary aspects, the binding construct is a bi-specific antigen-binding construct specific for a first epitope of FIX Padua and a second epitope of FIX Padua. In exemplary embodiments, the antibody is quadroma, heterodimeric bispecific antibody, bispecific antibody fusion, bispecific antibody fragment, a bispecific T-cell engager (BiTE), or a multi-specific antibody. In exemplary embodiments, the antibody is engineered to be bivalent, trivalent, or multivalent. See, e.g., Cuesta et al., "Multivalent antibodies: when design surpasses evolution" Trends in Biotechnology 28, 355-362 (2010); Holliger et al., "Engineered antibody fragments and the rise of single domains" Nat. Biotechnol. 23, 1126-1136 (2005); Chan et al., "Therapeutic antibodies for autoimmunity and inflammation" Nat Rev Immunol 10, 301-316 (2010); Byrne et al., "A tale of two specificities: bispecific antibodies for therapeutic and diagnostic applications" Trends Biotechnol. 31, 621-632 (2013). In some embodiments, the antibody is in monomeric form, while in other embodiments, the antibody is conjugated to one or more antibodies (e.g., each of which recognize the same epitope of the first antibody). Accordingly, in some aspects, the antibody is in dimeric, polymeric, oligomeric, or multimeric form.

In exemplary aspects, the binding construct is an antigen-binding fragment of an antibody or comprises an antigen-binding fragment of an antibody. The antigen-binding fragment (also referred to herein as "antigen-binding portion") may be an antigen-binding fragment of any of the antibodies described herein. The antigen-binding fragment can be any part of an antibody that has at least one antigen binding site, including, but not limited to, Fab, F(ab')2, a monospecific or bispecific Fab2, a trispecific Fabs, a monovalent IgG, scFv, dsFv, scFv-Fc, bispecific diabodies, trispecific triabodies, minibodies, or a fragment of IgNAR (e.g., V-NAR), or a fragment of hcIgG (e.g., VhH), or bis-scFvs, fragments expressed by a Fab expression library, and the like. In exemplary aspects, the antigen-binding fragment is a domain antibody, VhH domain, V-NAR domain, VH domain, VL domain, or the like. Antibody fragments of the disclosure, however, are not limited to these exemplary types of antibody fragments. In exemplary aspects, the binding construct comprises a Fab fragment. In exemplary aspects, the binding construct comprises two Fab fragments. In exemplary aspects, the binding construct comprises two Fab fragments connected via a linker. In exemplary aspects, the binding construct comprises or is a minibody comprising two Fab fragments. In exemplary aspects, the binding construct comprises or is a minibody comprising two Fab fragments joined via a linker. Minibodies are known in the art. See, e.g., Hu et al., Cancer Res 56: 3055-3061 (1996). In exemplary aspects, the binding construct comprises or is a minibody comprising two Fab fragments joined via a linker, optionally, comprising an alkaline phosphatase domain.

A domain antibody comprises a functional binding unit of an antibody, and can correspond to the variable regions of either the heavy (VH) or light (VL) chains of antibodies. A domain antibody can have a molecular weight of approximately 13 kDa, or approximately one-tenth of a full antibody. Domain antibodies may be derived from full antibodies such as those described herein.

The binding constructs in some embodiments are monomeric or polymeric, bispecific or trispecific, bivalent or trivalent. In exemplary aspects, the binding construct provided herein is monospecific. In exemplary aspects, the binding construct provided herein is bispecific. In exemplary aspects, the binding construct provided herein is fully human. In exemplary aspects, the binding construct comprises two Fab fragments and is bivalent. In exemplary aspects, the binding construct is a homodimer of two Fab fragments that are identical in structure. Thus, in exemplary aspects, the binding construct is bivalent but monospecific for FIX Padua. In exemplary aspects, the homodimer is dimerized via a helix-turn-helix motif. In exemplary aspects, the binding construct is a homodimer of two Fab mini antibodies that are identical in structure. Thus, in exemplary aspects, the binding construct is bivalent but monospecific for FIX Padua. In exemplary aspects, the homodimer of two Fab mini antibodies are dimerized via an alkaline phosphatase domain.

Antibody fragments that contain the antigen-binding, or idiotype, of the antibody molecule may be generated by techniques known in the art. For example, such fragments include, but are not limited to, the $F(ab')_2$ fragment which may be produced by pepsin digestion of the antibody molecule; the Fab' fragments which may be generated by reducing the disulfide bridges of the $F(ab')_2$ fragment; and the two Fab' fragments which may be generated by treating the antibody molecule with papain and a reducing agent.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7, 697-704 (1994)).

Recombinant antibody fragments, e.g., scFvs, can also be engineered to assemble into stable multimeric oligomers of high binding avidity and specificity to different target antigens. Such diabodies (dimers), triabodies (trimers) or tetrabodies (tetramers) are well known in the art, see e.g., Kortt et al., Biomol Eng. 2001 18:95-108, (2001) and Todorovska et al., J Immunol Methods. 248:47-66, (2001).

Bispecific antibodies (bscAb) are molecules comprising two single-chain Fv fragments joined via a glycine-serine linker using recombinant methods. The V light-chain (VL) and V heavy-chain (VH) domains of two antibodies of interest in exemplary embodiments are isolated using standard PCR methods. The VL and VH cDNA's obtained from each hybridoma are then joined to form a single-chain fragment in a two-step fusion PCR. Bispecific fusion proteins are prepared in a similar manner. Bispecific single-chain antibodies and bispecific fusion proteins are antibody substances included within the scope of the present disclosure. Exemplary bispecific antibodies are taught in U.S. Patent Application Publication No. 2005-0282233A1 and International Patent Application Publication No. WO 2005/087812, both applications of which are incorporated herein by reference in their entirety.

In exemplary embodiments, the binding construct is a biparatopic antibody, or a biparatopic antigen-binding fragment thereof, having the capability of binding two different non-overlapping epitopes on the same target antigen molecule. By simultaneously binding to the same cell surface targets, biparatopic antibodies and biparatopic antigen-binding fragments thereof may result in enhanced binding avidity, leading to preferential (strong) binding to only cells that express the targets, thus fine-tuning the antibody selectivity. It has been demonstrated that biparatopic antibodies or biparatopic antigen-binding fragments thereof, by simultaneously binding to two different epitopes on the same target molecule, could even potentially acquire new functionality that could not be achieved with the parent antibodies (or antigen-binding fragments) when used alone or in combination. In exemplary aspects, the binding constructs provided herein are biparatopic for FIX Padua.

In exemplary embodiments, the antigen-binding fragment is engineered to be bispecific, trispecific, or multi-specific. In exemplary aspects, the antigen-binding fragment comprises two or more distinct antigen-binding regions. In some aspects, the antigen-binding fragment is a bispecific or trispecific antibody specific for FIX Padua and at least one other antigen. In exemplary aspects, the binding construct is a bi-specific antigen-binding fragment specific for a first epitope of FIX Padua and a second epitope of FIX Padua. In exemplary embodiments, the antigen-binding fragment is engineered to be bivalent, trivalent, or multivalent. In exemplary embodiments, the binding construct is a bivalent Fab fragment monospecific for FIX Padua. In some embodiments, the antigen-binding fragment is in monomeric form, while in other embodiments, the antigen-binding fragment is conjugated to one or more antigen-binding fragments (e.g., each of which recognize the same epitope of the first antigen-binding fragment). Accordingly, in some aspects, the antigen-binding fragment is dimerized, polymerized, oligomerized, or multimerized. In exemplary aspects, the binding construct is a dimerized Fab fragment. In exemplary aspects, the binding construct is a fully human dimerized Fab fragment. In exemplary aspects, the binding construct is dimerized via a helix-turn-helix motif. In exemplary embodiments, the antigen-binding fragment is engineered to be bivalent, trivalent, or multivalent. In exemplary embodiments, the binding construct is a dimerized bivalent Fab fragment monospecific for FIX Padua, wherein the binding construct is dimerized via a helix-turn-helix motif.

In exemplary aspects, the binding construct, e.g., antibody or antigen-binding fragment thereof, comprises the amino acid sequences of: SSYAIS (SEQ ID NO: 6); GIVPAFGTANYAQKFQG (SEQ ID NO: 7); SWGVISFAY (SEQ ID NO: 8); RASQDISSYLN (SEQ ID NO: 9); AASNLQS (SEQ ID NO: 10); and MQYDSLPFTF (SEQ ID NO: 11). In exemplary aspects, one or more amino acids are present between each of SEQ ID NOs: 6-11. In exemplary aspects, the binding construct, e.g., antibody or antigen-binding fragment thereof, comprises the sequence of SEQ ID NO: 24 or SEQ ID NO: 25 or both SEQ ID NOs: 24 and 25. In exemplary aspects, the binding construct, e.g., antibody or antigen-binding fragment thereof, comprises the sequence of SEQ ID NO: 26 or SEQ ID NO: 27 or both SEQ ID NOs: 26 and 27. In exemplary aspects, the amino acid sequence of the binding construct, e.g., antibody or antigen-binding fragment thereof, comprises additional sequences of, e.g., linker(s), expression tags (e.g., His tags, FLAG tags, myc tags, fluorescent proteins (e.g., green fluorescent protein, blue fluorescent protein, red fluorescent protein, yellow fluorescent protein, cyan fluorescent protein, enhanced green fluorescent protein, and the like). In exemplary aspects, the binding construct, e.g., antibody or antigen-binding fragment thereof, comprises the sequence of a His tag and/or a FLAG tag. In exemplary aspects, the FLAG tag comprises a sequence of SEQ ID NO: 12. In exemplary aspects, the His tag comprises a sequence of SEQ ID NO: 13. In exemplary aspects, the binding construct, e.g., antibody or antigen-binding fragment thereof, comprises a linker. In exemplary aspects, the binding construct, e.g., antibody or antigen-binding fragment thereof, comprises a synthetic double helix loop helix motif, such as that described in Haylock et al., Int J. Oncol. 48(2): 461-470 (2016) or Wang et al., Anal. Chem. 78: 997-1004 (2006). In exemplary aspects, the binding construct, e.g., antibody or antigen-binding fragment thereof, comprises a constant antibody domain. Such antibody domains are described in Hu et al., Cancer Res 56: 3055-3061 (1996) and McGregor et al., Mol Immuno 31: 219-226 (1994). In exemplary aspects, the binding construct, e.g., antibody or antigen-binding fragment thereof, comprises a bacterial alkaline phosphatase domain, such as that described in Wang et al. (2006), supra. In exemplary aspects, the binding construct, e.g., antibody or antigen-binding fragment thereof, comprises the sequence of SEQ ID NO: 28 or SEQ ID NO: 27 or both SEQ ID NOs: 28 and 27.

Aptamers

In some embodiments, the binding construct is an analog of an antibody. In some aspects, the binding construct is an aptamer. Recent advances in the field of combinatorial sciences have identified short polymer sequences (e.g., oligonucleic acid or peptide molecules) with high affinity and specificity to a given target. For example, SELEX technology has been used to identify DNA and RNA aptamers with binding properties that rival mammalian antibodies, the field of immunology has generated and isolated antibodies or antibody fragments which bind to a myriad of compounds and phage display has been utilized to discover new peptide sequences with very favorable binding properties. Based on the success of these molecular evolution techniques, it is certain that molecules can be created which bind to any target molecule. A loop structure is often involved with providing the desired binding attributes, as in the case of aptamers which often utilize hairpin loops created from short regions without complimentary base pairing, and naturally derived antibodies that utilize combinatorial arrangement of looped hyper-variable regions and new phage display libraries utilizing cyclic peptides that have shown improved results when compared to linear peptide phage display results. For more on aptamers, see, generally, Gold, L., Singer, B., He, Y. Y., Brody. E., "Aptamers As Therapeutic And Diagnostic Agents," J. Biotechnol. 74:5-13 (2000). Relevant techniques for generating aptamers may be found in U.S. Pat. No. 6,699,843, which is incorporated by reference in its entirety.

Methods of Antibody or Antigen-binding Fragment Production

Suitable methods of making antibodies are known in the art. For instance, standard hybridoma methods are described in, e.g., Harlow and Lane (eds.), Antibodies: A Laboratory Manual, CSH Press (1988), and CA. Janeway et al. (eds.), Immunobiology, 5th Ed., Garland Publishing, New York, N.Y. (2001)).

Briefly, a polyclonal antibody is prepared by immunizing an animal with an immunogen comprising a polypeptide of the present disclosure and collecting antisera from that immunized animal. A wide range of animal species can be used for the production of antisera. In some aspects, an animal used for production of anti-antisera is a non-human animal including rabbits, mice, rats, hamsters, goat, sheep, pigs or horses. Because of the relatively large blood volume of rabbits, a rabbit is a preferred choice for production of polyclonal antibodies. In an exemplary method for generating a polyclonal antisera immunoreactive with the chosen FIX Padua epitope, 50 µg of FIX Padua antigen is emulsified in Freund's Complete Adjuvant for immunization of rabbits. At intervals of, for example, 21 days, 50 µg of epitope are emulsified in Freund's Incomplete Adjuvant for boosts. Polyclonal antisera may be obtained, after allowing time for antibody generation, simply by bleeding the animal and preparing serum samples from the whole blood.

Monoclonal antibodies for use in the methods of the disclosure may be prepared using any technique which provides for the production of antibody molecules by continuous cell lines in culture. These include but are not limited to the hybridoma technique originally described by Koehler and Milstein (Nature 256: 495-497, 1975), the human B-cell hybridoma technique (Kosbor et al., Immunol Today 4:72, 1983; Cote et al., Proc Natl Acad Sci 80: 2026-2030, 1983) and the EBV-hybridoma technique (Cole et al., Monoclonal Antibodies and Cancer Therapy, Alan R Liss Inc, New York N.Y., pp 77-96, (1985).

Briefly, in exemplary embodiments, to generate monoclonal antibodies, a mouse is injected periodically with recombinant FIX Padua against which the antibody is to be raised (e.g., 10-20 µg emulsified in Freund's Complete Adjuvant). The mouse is given a final pre-fusion boost of FIX Padua in PBS, and four days later the mouse is sacrificed and its spleen removed. The spleen is placed in 10 ml serum-free RPMI 1640, and a single cell suspension is formed by grinding the spleen between the frosted ends of two glass microscope slides submerged in serum-free RPMI 1640, supplemented with 2 mM L-glutamine, 1 mM sodium pyruvate, 100 units/ml penicillin, and 100 µg/ml streptomycin (RPMI) (Gibco, Canada). The cell suspension is filtered through sterile 70-mesh Nitex cell strainer (Becton Dickinson, Parsippany, N.J.), and is washed twice by centrifuging at 200 g for 5 minutes and resuspending the pellet in 20 ml serum-free RPMI. Splenocytes taken from three naïve Balb/c mice are prepared in a similar manner and used as a control. NS-1 myeloma cells, kept in log phase in RPMI with 11% fetal bovine serum (FBS) (Hyclone Laboratories, Inc., Logan, Utah) for three days prior to fusion, are centrifuged at 200 g for 5 minutes, and the pellet is washed twice.

Spleen cells ($1\times10^8$) are combined with $2.0\times10^7$ NS-1 cells and centrifuged, and the supernatant is aspirated. The cell pellet is dislodged by tapping the tube, and 1 ml of 37° C. PEG 1500 (50% in 75 mM Hepes, pH 8.0) (Boehringer Mannheim) is added with stirring over the course of 1 minute, followed by the addition of 7 ml of serum-free RPMI over 7 minutes. An additional 8 ml RPMI is added and the cells are centrifuged at 200 g for 10 minutes. After discarding the supernatant, the pellet is resuspended in 200 ml RPMI containing 15% FBS, 100 µM sodium hypoxanthine, 0.4 µM aminopterin, 16 µM thymidine (HAT) (Gibco), 25 units/ml IL-6 (Boehringer Mannheim) and $1.5\times10^6$ splenocytes/ml and plated into 10 Corning flat-bottom 96-well tissue culture plates (Corning, Corning N.Y.).

On days 2, 4, and 6, after the fusion, 100 µl of medium is removed from the wells of the fusion plates and replaced with fresh medium. On day 8, the fusion is screened by ELISA, testing for the presence of mouse IgG binding to FIX Padua as follows. Immulon 4 plates (Dynatech, Cambridge, Mass.) are coated for 2 hours at 37° C. with 100 ng/well of EGFR diluted in 25 mM Tris, pH 7.5. The coating solution is aspirated and 200 µl/well of blocking solution (0.5% fish skin gelatin (Sigma) diluted in CMF-PBS) is added and incubated for 30 min. at 37° C. Plates are washed three times with PBS with 0.05% Tween 20 (PBST) and 50 µl culture supernatant is added. After incubation at 37° C. for 30 minutes, and washing as above, 50 µl of horseradish peroxidase conjugated goat anti-mouse IgG(fc) (Jackson ImmunoResearch, West Grove, Pa.) diluted 1:3500 in PBST is added. Plates are incubated as above, washed four times with PBST, and 100 µl substrate, consisting of 1 mg/ml o-phenylene diamine (Sigma) and 0.1 µl/ml 30% $H_2O_2$ in 100 mM Citrate, pH 4.5, are added. The color reaction is stopped after 5 minutes with the addition of 50 µl of 15% $H_2SO_4$. $A_{490}$ is read on a plate reader (Dynatech).

Selected fusion wells are cloned twice by dilution into 96-well plates and visual scoring of the number of colonies/well after 5 days. The monoclonal antibodies produced by hybridomas are isotyped using the Isostrip system (Boehringer Mannheim, Indianapolis, Ind.).

When the hybridoma technique is employed, myeloma cell lines may be used. Such cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and 5194/15XX0 Bul; for rats, one may use R210.RCY3, Y3-Ag 1.2.3, IR983F and 46210; and U-266, GM1500-GRG2, LICR-LON-HMy2 and UC729-6 are all useful in connection with cell fusions.

Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Alternatively, other methods, such as EBV-hybridoma methods (Haskard and Archer, J. Immunol. Methods, 74(2), 361-67 (1984), and Roder et al., Methods Enzymol., 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Antibodies may also be produced by inducing in vivo production in the lymphocyte population or by screening recombinant immunoglobulin libraries or panels of highly specific binding reagents as disclosed in Orlandi et al (Proc Natl Acad Sci 86: 3833-3837; 1989), and Winter G and Milstein C (Nature 349: 293-299, 1991). If the full sequence of the antibody or antigen-binding fragment is known, then methods of producing recombinant proteins may be employed. See, e.g., "Protein production and purification" Nat Methods 5(2): 135-146 (2008).

Phage display also can be used to generate the antibody of the present disclosures. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, 3rd Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150). Related methods also are described in U.S. Pat. Nos. 5,403, 484; 5,571,698; 5,837,500; 5,702,892. The techniques described in U.S. Pat. Nos. 5,780,279; 5,821,047; 5,824, 520; 5,855,885; 5,858,657; 5,871,907; 5,969,108; 6,057, 098; and 6,225,447.

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 BI, and United Kingdom Patent No. 2188638. Humanized antibodies can also be generated using the antibody resurfacing technology described in U.S. Pat. No. 5,639,641 and Pedersen et al., J. Mol. Biol, 235, 959-973 (1994). A preferred chimeric or humanized antibody has a human constant region, while the variable region, or at least a CDR, of the antibody is derived from a non-human species. Methods for humanizing non-human antibodies are well known in the art. (See U.S. Pat. Nos. 5,585,089, and 5,693,762.) Generally, a humanized antibody has one or more amino acid residues introduced into its framework region from a source which is non-human. Humanization can be performed, for example, using methods described in Jones et al. (Nature 321: 522-525, 1986), Riechmann et al., (Nature, 332: 323-327, 1988) and Verhoeyen et al. (Science 239:1534-1536, 1988), by substituting at least a portion of a rodent complementarity-determining region (CDRs) for the corresponding regions of a human antibody. Numerous techniques for preparing engineered antibodies are described, e.g., in Owens and Young, J. Immunol. Meth., 168:149-165 (1994). Further changes can then be introduced into the antibody framework to modulate affinity or immunogenicity.

Techniques developed for the production of "chimeric antibodies", the splicing of mouse antibody genes to human antibody genes to obtain a molecule with appropriate antigen specificity and biological activity, can be used (Morrison et al., Proc Natl Acad Sci 81: 6851-6855 (1984); Neuberger et al., Nature 312: 604-608 (1984); Takeda et al., Nature 314: 452-454 (1985)). Alternatively, techniques described for the production of single chain antibodies (U.S. Pat. No. 4,946,778) can be adapted to produce EGFR- or HSP90-specific single chain antibodies.

Likewise, using techniques known in the art to isolate CDRs, compositions comprising CDRs are generated. Complementarity determining regions are characterized by six polypeptide loops, three loops for each of the heavy or light chain variable regions. The amino acid position in a CDR is defined by Kabat et al., "Sequences of Proteins of Immunological Interest," U.S. Department of Health and Human Services, (1983), which is incorporated herein by reference. For example, hypervariable regions of human antibodies are roughly defined to be found at residues 28 to 35, from 49-59 and from residues 92-103 of the heavy and light chain variable regions (Janeway and Travers, Immunobiology, $2^{nd}$ Edition, Garland Publishing, New York, (1996)). The murine CDRs also are found at approximately these amino acid residues. It is understood in the art that CDR regions may be found within several amino acids of these approximated residues set forth above. An immunoglobulin variable region also consists of four "framework" regions surrounding the CDRs (FR1-4). The sequences of the framework regions of different light or heavy chains are highly conserved within a species, and are also conserved between human and murine sequences.

Compositions comprising one, two, and/or three CDRs of a heavy chain variable region or a light chain variable region of a monoclonal antibody are generated. Techniques for cloning and expressing nucleotide and polypeptide sequences are well-established in the art (see e.g. Sambrook et al., *Molecular Cloning: A Laboratory Manual*, $2^{nd}$ Edition, Cold Spring Harbor, N.Y. (1989)). The amplified CDR sequences are ligated into an appropriate expression vector. The vector comprising one, two, three, four, five and/or six cloned CDRs optionally contains additional polypeptide encoding regions linked to the CDR.

Framework regions (FR) of a murine antibody are humanized by substituting compatible human framework regions chosen from a large database of human antibody variable sequences, including over twelve hundred human VH sequences and over one thousand VL sequences. The database of antibody sequences used for comparison is downloaded from Andrew C. R. Martin's KabatMan web page (http://www.rubic.rdg.ac.uk/abs/). The Kabat method for identifying CDR provides a means for delineating the approximate CDR and framework regions from any human antibody and comparing the sequence of a murine antibody for similarity to determine the CDRs and FRs. Best matched human VH and VL sequences are chosen on the basis of high overall framework matching, similar CDR length, and minimal mismatching of canonical and VH/VL contact residues. Human framework regions most similar to the murine sequence are inserted between the murine CDR. Alternatively, the murine framework region may be modified by making amino acid substitutions of all or part of the native framework region that more closely resemble a framework region of a human antibody.

Additionally, another useful technique for generating antibodies for use in the present disclosure may be one which uses a rational design type approach. The goal of rational design is to produce structural analogs of biologically active polypeptides or compounds with which they interact (agonists, antagonists, inhibitors, peptidomimetics, binding partners, etc.). In one approach, one would generate a three-dimensional structure for the antibodies or an epitope binding fragment thereof. This could be accomplished by x-ray crystallography, computer modeling or by a combination of both approaches. An alternative approach, "alanine scan," involves the random replacement of residues throughout molecule with alanine, and the resulting effect on function determined.

Chemically constructed bispecific antibodies may be prepared by chemically cross-linking heterologous Fab or F(ab')$_2$ fragments by means of chemicals such as heterobifunctional reagent succinimidyl-3-(2-pyridyldithiol)-propionate (SPDP, Pierce Chemicals, Rockford, Ill.). The Fab and F(ab')$_2$ fragments can be obtained from intact antibody by digesting it with papain or pepsin, respectively (Karpovsky et al., J. Exp. Med. 160:1686-701 (1984); Titus et al., J. Immunol., 138:4018-22 (1987)).

Methods of testing antibodies for the ability to bind to the epitope of the FIX Padua regardless of how the antibodies are produced are known in the art and include any antibody-antigen binding assay, such as, for example, radioimmunoassay (RIA), ELISA, Western blot, immunoprecipitation, surface plasmon resonance, and competitive inhibition assays (see, e.g., Janeway et al., infra, and U.S. Patent Application Publication No. 2002/0197266).

Polypeptides

A polypeptide comprising an amino acid sequence comprising each of SEQ ID NOs: 6-11 is further provided herein. The polypeptide binds to FIXp and not to WT FIX, e.g., the polypeptide binds to FIXp only even in the presence of WT FIX, optionally, even in the presence of other coagulation factors, e.g., Factor II and Factor X. In exemplary aspects, the polypeptide binds to FIXp in a sample comprising at least 5%, at least 10% or at least 20% human plasma. In exemplary aspects, one or more amino acids are present between each of SEQ ID NOs: 6-11. In exemplary aspects, the polypeptide comprises the sequence of SEQ ID NO: 24 or SEQ ID NO: 25 or both SEQ ID NOs: 24 and 25. In exemplary aspects, the polypeptide comprises the sequence of SEQ ID NO: 26 or SEQ ID NO: 27 or both SEQ ID NOs: 26 and 27. In exemplary aspects, the amino acid sequence of the polypeptide comprises additional sequences of, e.g., linker(s), expression tags (e.g., His tags, FLAG tags, myc tags, fluorescent proteins (e.g., green fluorescent protein, blue fluorescent protein, red fluorescent protein, yellow fluorescent protein, cyan fluorescent protein, enhanced green fluorescent protein, and the like). In exemplary aspects, the polypeptide comprises the sequence of a His tag and/or a FLAG tag. In exemplary aspects, the FLAG tag comprises a sequence of SEQ ID NO: 12. In exemplary aspects, the His tag comprises a sequence of SEQ ID NO: 13. In exemplary aspects, the polypeptide comprises a linker. In exemplary aspects, the polypeptide comprises a sequence of a synthetic double helix loop helix motif, such as that described in Haylock et al., Int J. Oncol. 48(2): 461-470 (2016) or Wang et al., Anal. Chem. 78: 997-1004 (2006). In exemplary aspects, the polypeptide comprises a sequence of a constant antibody domain. Such antibody domains are described in Hu et al., Cancer Res 56: 3055-3061 (1996) and McGregor et al., Mol Immuno 31: 219-226 (1994). In exemplary aspects, the polypeptide comprises a bacterial alkaline phosphatase domain, such as that described in Wang et al. (2006), supra. In exemplary aspects, the polypeptide comprises the sequence of SEQ ID NO: 28 or SEQ ID NO: 27 or both SEQ ID NOs: 28 and 27.

Conjugates

The binding constructs described herein can be modified, for instance, by glycosylation, amidation, carboxylation, or phosphorylation, or by the creation of acid addition salts, amides, esters, in particular C-terminal esters, and N-acyl derivatives. The binding construct also can be modified to create derivatives by forming covalent or noncovalent complexes with other moieties, i.e., conjugates. Covalently bound complexes can be prepared by linking the chemical moieties to functional groups on the side chains of amino acids comprising the binding construct, or at the N- or C-terminus.

In some embodiments, the binding constructs of the present disclosure are attached, linked, joined, or conjugated to a second moiety (e.g., a heterologous moiety) and the resulting product is a conjugate. Accordingly, provided herein are conjugates comprising the binding constructs described herein (covalently or non-covalently) linked to a heterologous moiety. As used herein, the term "heterologous moiety" refers to any molecule (chemical or biochemical, naturally-occurring or non-coded) which is different from the binding constructs of the invention. Exemplary heterologous moieties include, but are not limited to, a polymer, a carbohydrate, a lipid, a nucleic acid, an oligonucleotide, a DNA or RNA, an amino acid, peptide, polypeptide, protein, therapeutic agent, (e.g., a cytotoxic agent, cytokine), a diagnostic agent or a detecting agent.

In some embodiments, the binding constructs are chemically modified with various heterologous moieties. In some embodiments, the chemical modifications impart additional desirable characteristics as discussed herein. Chemical modifications in some aspects take a number of different forms such as heterologous peptides, polysaccharides, lipids, radioisotopes, non-standard amino acid resides and nucleic acids, metal chelates, and various cytotoxic agents.

In some embodiments, the binding constructs are fused to heterologous peptides to confer various properties, e.g., increased solubility and/or stability and/or half-life, resistance to proteolytic cleavage, modulation of clearance, targeting to particular cell or tissue types. In some embodiments, the binding constructs are linked to an Fc domain of IgG or other immunoglobulin. In some embodiments, the binding construct is fused to alkaline phosphatase (AP). Methods for making Fc or AP fusion constructs are found in International Patent Publication No. WO 02/060950. By fusing the binding construct with protein domains that have specific properties (e.g., half-life, bioavailability) it is possible to confer these properties to the binding construct of the invention.

The binding constructs can be conjugated to a detecting agent (e.g., a detectable label or a reporter group), including, but not limited to a radiolabel, a fluorescent label, an enzyme (e.g., that catalyzes a calorimetric or fluorometric reaction), a substrate, a solid matrix, or a carrier (e.g., biotin or avidin). In exemplary aspects, the fluorescent label comprises a rhodamine dye, fluorescein dye and/or a cyanine dye. In exemplary embodiments, the fluorescent label comprises a set of dyes, e.g., a rhodamine dye, TAMRA, and a fluorescein dye, FAM. In another embodiment, the fluorescent label comprises of a set of fluorescent dyes formed by selecting two or more dyes from the group consisting of Oregon Green 488, Flitorescein-EX, fluorescein isothiocyanate, Rhodamine Red-X, Lissamine rhodamine B, Calcein, Fluorescein, Rhodamine, one or more BODIPY dyes, Texas Red, Oregon Green 514, and one or more Alexa Fhiors. Representative BOD1PY dyes include BODIPY FL, BODIPY R6G, BOD1PY TMR, BOD1PY 581/591, BODIPY TR, BODIPY 630/650 and BODIPY 650/665. Representative Alexa Fluors include Alexa Fluor 350, 405, 430, 488, 500, 514, 532, 546, 555, 568, 594, 610, 633, 635, 647, 660, 680, 700, 750 and 790. In exemplary aspects, the fluorescent label comprises one or more of Oregon Green 488, fluorescein-EX, FITC, Rhodamine Red-X, Lissamine rhodamine B, calcein, fluorescein, rhodamine, BODIPYS, and Texas Red, e.g. which are disclosed in Molecular Probes Handbook, 1 1th Edition (2010). In exemplary aspects, the detectable label is selected from radioisotopes, chromophores, fluorophores, fluorochromes, enzymes (e.g., horseradish peroxidase), linker molecules or other moieties or compounds which either emit a detectable signal (e.g., radioactivity, fluorescence, color) or emit a detectable signal after exposure of the label to its substrate. A variety of detectable label/substrate pairs (e.g., horseradish peroxidase/diaminobenzidine, biotin/streptavidin, luciferase/luciferin), methods for labeling antibodies, and methods for using labeled secondary antibodies to detect an antigen are well known in the art. See, e.g., Harlow and Lane, eds. (Using Antibodies: A Laboratory Manual (1999) Cold Spring Harbor Laboratory Press, Cold Spring Harbor, N.Y.).

In some embodiments, the binding construct is directly joined to a heterologous moiety in the absence of a linker. In alternative aspects, the binding construct is indirectly connected to the heterologous moiety via one or more linkers. Whether directly joined together or indirectly joined together through a linker, the binding construct may be connected through covalent bonds (e.g., a peptide, ester, amide, or sulfhydryl bond) or non-covalent bonds (e.g., via hydrophobic interaction, hydrogen bond, van der Waals bond, electrostatic or ionic interaction), or a combination thereof. The binding construct of the invention and heterologous moiety may be connected via any means known in the art, including, but not limited to, via a linker of any of the invention.

Particular residues of the binding constructs described herein represent exemplary sites at which a heterologous moiety may be attached. For example, Cys, His, Lys and N-terminal residues, Arg, Tyr, Asp, Glu, Ser, Thr, Pro represent sites at which the heterologous moiety may be attached. In some aspects, the residue (or a part thereof) is activated with one or more agents and/or chemicals prior to attaching the heterologous moiety.

Derivatization with bifunctional agents is useful for cross-linking the binding construct to water-insoluble support matrixes. Such derivation may also provide the linker that may connect adjacent binding elements in a binding construct, or binding elements to a heterologous peptide, e.g., an Fc fragment. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidylpropioonate), and bifunctional maleimides such as bis-N-maleimido-1,8-octane. Derivatizing agents such as methyl-3-[(p-azidophenyl) dithio] propioimidate yield photoactivatable intermediates that are capable of forming cross links in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440, incorporated herein by reference, are employed for protein immobilization.

In general, chemical derivatization may be performed under any suitable condition used to react a protein with a heterologous moiety, e.g., an activated polymer molecule. Methods for preparing chemical derivatives of polypeptides will generally comprise the steps of (a) reacting the binding construct with the heterologous moiety, e.g., activated polymer molecule (such as a reactive ester or aldehyde derivative of the polymer molecule) under conditions whereby the binding construct becomes attached to one or more polymer molecules, and (b) obtaining the reaction product(s). The optimal reaction conditions will be determined based on known parameters and the desired result. For example, the larger the ratio of polymer molecules:protein, the greater the amount of attached polymer molecule. In some embodiments, the compound may have a single polymer molecule moiety at the amino terminus. (See, e.g., U.S. Pat. No. 5,234,784).

Derivatized binding constructs disclosed herein may have additional activities, enhanced or reduced biological activity, or other characteristics, such as increased or decreased half-life, as compared to the non-derivatized molecules.

Conjugates: Fc Fusions

For substituents such as an Fc region of human IgG, the fusion can be fused directly to a binding construct of the invention or fused through an intervening sequence. For example, a human IgG hinge, CH2 and CH3 region may be fused at either the N-terminus or C-terminus of a binding construct to attach the Fc region. The resulting Fc-fusion construct enables purification via a Protein A affinity column (Pierce, Rockford, Ill.). Peptide and proteins fused to an Fc region can exhibit a substantially greater half-life in vivo than the unfused counterpart. A fusion to an Fc region allows for dimerization/multimerization of the fusion polypeptide. The Fc region may be a naturally occurring Fc region, or may be modified for superior characteristics, e.g., therapeutic or diagnostic qualities, circulation time, reduced aggregation. As noted above, in some embodiments, the binding constructs are conjugated, e.g., fused to an immunoglobulin or portion thereof (e.g., variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable heterologous moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

Heterologous Moieties: Polymers, Carbohydrates, and Lipids

In exemplary embodiments, the heterologous moiety is a polymer. The polymer may be branched or unbranched. The polymer may be of any molecular weight. The polymer in some embodiments has an average molecular weight of between about 2 kDa to about 100 kDa (the term "about" indicating that in preparations of a water soluble polymer, some molecules will weigh more, some less, than the stated molecular weight). The average molecular weight of the polymer is in some aspect between about 5 kDa and about 50 kDa, between about 12 kDa to about 40 kDa or between about 20 kDa to about 35 kDa.

In some embodiments, the polymer is modified to have a single reactive group, such as an active ester for acylation or an aldehyde for alkylation, so that the degree of polymerization may be controlled. The polymer in some embodiments is water soluble so that the protein to which it is attached does not precipitate in an aqueous environment, such as a physiological environment. In some embodiments, when, for example, the composition is used for therapeutic use, the polymer is pharmaceutically acceptable. Additionally, in some aspects, the polymer is a mixture of polymers, e.g., a co-polymer, a block co-polymer.

In some embodiments, the polymer is selected from the group consisting of: polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

In some aspects, the polymer is a biodegradable polymer, including a synthetic biodegradable polymer (e.g., polymers of lactic acid and glycolic acid, polyanhydrides, poly(ortho) esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In some embodiments, the polymer is a water-soluble polymer or a hydrophilic polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof. In some aspects, the water soluble polymers or mixtures thereof include, but are not limited to, N-linked or O-linked carbohydrates, sugars, phosphates, carbohydrates; sugars; phosphates; polyethylene glycol (PEG) (including the forms of PEG that have been used to derivatize proteins, including mono-(C1-C10) alkoxy- or aryloxy-polyethylene glycol); monomethoxy-polyethylene glycol; dextran (such as low molecular weight dextran, of, for example about 6 kD), cellulose; cellulose; other carbohydrate-based polymers, poly-(N-vinyl pyrrolidone)polyethylene glycol, propylene glycol homopolymers, a polypropylene oxide/ethylene oxide co-polymer, polyoxyethylated polyols (e.g., glycerol) and polyvinyl alcohol. Also encompassed by the present invention are bifunctional crosslinking molecules which may be used to prepare covalently attached multimers.

A particularly preferred water-soluble polymer for use herein is polyethylene glycol (PEG). As used herein, polyethylene glycol is meant to encompass any of the forms of PEG that can be used to derivatize other proteins, such as mono-(C1-C10) alkoxy- or aryloxy-polyethylene glycol. PEG is a linear or branched neutral polyether, available in a broad range of molecular weights, and is soluble in water and most organic solvents. PEG is effective at excluding other polymers or peptides when present in water, primarily through its high dynamic chain mobility and hydrophibic nature, thus creating a water shell or hydration sphere when attached to other proteins or polymer surfaces. PEG is nontoxic, non-immunogenic, and approved by the Food and Drug Administration for internal consumption.

Methods for preparing pegylated compounds may comprise the steps of (a) reacting the compound with polyethylene glycol (such as a reactive ester or aldehyde derivative of PEG) under conditions whereby the compound becomes attached to one or more PEG groups, and (b) obtaining the reaction product(s). In general, the optimal reaction conditions for the acylation reactions will be determined based on known parameters and the desired result. For example, the larger the ratio of PEG:compound, the greater the percentage of poly-pegylated product. In some embodiments, the binding construct will have a single PEG moiety at the N-terminus. See U.S. Pat. No. 8,234,784, herein incorporated by reference.

In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

Heterologous Moieties: Therapeutic Agents

In some embodiments, the heterologous moiety is a therapeutic agent. The therapeutic agent may be any of those known in the art. Examples of therapeutic agents that are contemplated herein include, but are not limited to, natural enzymes, proteins derived from natural sources, recombinant proteins, natural peptides, synthetic peptides, cyclic peptides, antibodies, receptor agonists, cytotoxic agents, immunoglobins, beta-adrenergic blocking agents, calcium channel blockers, coronary vasodilators, cardiac glycosides, antiarrhythmics, cardiac sympathomemetics, angiotensin converting enzyme (ACE) inhibitors, diuretics, inotropes, cholesterol and triglyceride reducers, bile acid sequestrants, fibrates, 3-hydroxy-3-methylgluteryl (HMG)-CoA reductase inhibitors, niacin derivatives, antiadrenergic agents, alpha-adrenergic blocking agents, centrally acting antiadrenergic agents, vasodilators, potassium-sparing agents, thiazides and related agents, angiotensin II receptor antagonists, peripheral vasodilators, antiandrogens, estrogens, antibiotics, retinoids, insulins and analogs, alpha-glucosidase inhibitors, biguanides, meglitinides, sulfonylureas, thizaolidinediones, androgens, progestogens, bone metabolism regulators, anterior pituitary hormones, hypothalamic hormones, posterior pituitary hormones, gonadotropins, gonadotropin-releasing hormone antagonists, ovulation stimulants, selective estrogen receptor modulators, antithyroid agents, thyroid hormones, bulk forming agents, laxatives, antiperistaltics, flora modifiers, intestinal adsorbents, intestinal anti-infectives, antianorexic, anticachexic, antibulimics, appetite suppressants, antiobesity agents, antacids, upper gastrointestinal tract agents, anticholinergic agents, aminosalicylic acid derivatives, biological response modifiers, corticosteroids, antispasmodics, 5-HT4 partial agonists, antihistamines, cannabinoids, dopamine antagonists, serotonin antagonists, cytoprotectives, histamine H2-receptor antagonists, mucosal protective agent, proton pump inhibitors, *H. pylori* eradication therapy, erythropoieses stimulants, hematopoietic agents, anemia agents, heparins, antifibrinolytics, hemostatics, blood coagulation factors, adenosine diphosphate inhibitors, glycoprotein receptor inhibitors, fibrinogen-platelet binding inhibitors, thromboxane-$A_2$ inhibitors, plasminogen activators, antithrombotic agents, glucocorticoids, mineralcorticoids, corticosteroids, selective immunosuppressive agents, antifungals, drugs involved in prophylactic therapy, AIDS-associated infections, cytomegalovirus, non-nucleoside reverse transcriptase inhibitors, nucleoside analog reverse transcriptse inhibitors, protease inhibitors, anemia, Kaposi's sarcoma, am inoglycosides, carbapenems, cephalosporins, glycopoptides, lincosam ides, macrolies, oxazolidinones, penicillins, streptogram ins, sulfonamides, trimethoprim and derivatives, tetracyclines, anthelmintics, amebicies, biguanides, cinchona alkaloids, folic acid antagonists, quinoline derivatives, *Pneumocystis carinii* therapy, hydrazides, imidazoles, triazoles, nitroimidzaoles, cyclic amines, neuraminidase inhibitors, nucleosides, phosphate binders, cholinesterase inhibitors, adjunctive therapy, barbiturates and derivatives, benzodiazepines, gamma aminobutyric acid derivatives, hydantoin derivatives, iminostilbene derivatives, succinimide derivatives, anticonvulsants, ergot alkaloids, antimigrane preparations, biological response modifiers, carbamic acid eaters, tricyclic derivatives, depolarizing agents, nondepolarizing agents, neuromuscular paralytic agents, CNS stimulants, dopaminergic reagents, monoamine oxidase inhibitors, COMT inhibitors, alkyl sulphonates, ethylenimines, imidazotetrazines, nitrogen mustard analogs, nitrosoureas, platinum-containing compounds, antimetabolites, purine analogs, pyrimidine analogs, urea derivatives, antracyclines, actinomycinds, camptothecin derivatives, epipodophyllotoxins, taxanes, vinca alkaloids and analogs, antiandrogens, antiestrogens, nonsteroidal aromatase inhibitors, protein kinase inhibitor antineoplastics, azaspirodecanedione derivatives, anxiolytics, stimulants, monoamind reuptake inhibitors, selective serotonin reuptake inhibitors, antidepressants, benzisooxazole derivatives, butyrophenone derivatives, dibenzodiazepine derivatives, dibenzothiazepine derivatives, diphenylbutylpiperidine derivatives, phenothiazines, thienobenzodiazepine derivatives, thioxanthene derivatives, allergenic extracts, nonsteroidal agents, leukotriene receptor antagonists, xanthines, endothelin receptor antagonist, prostaglandins, lung surfactants, mucolytics, antimitotics, uricosurics, xanthine oxidase inhibitors, phosphodiesterase inhibitors, metheamine salts, nitrofuran derivatives, quinolones, smooth muscle relaxants, parasympathomimetic agents, halogenated hydrocarbons, esters of amino benzoic acid, amides (e.g. lidocaine, articaine hydrochloride, bupivacaine hydrochloride), antipyretics, hynotics and sedatives, cyclopyrrolones, pyrazolopyrimidines, nonsteroidal anti-inflammatory drugs, opioids, para-aminophenol derivatives, alcohol dehydrogenase inhibitor, heparin antagonists, adsorbents, emetics, opioid antagonists, cholinesterase reactivators, nicotine replacement therapy, vitamin A analogs and antagonists, vitamin B analogs and antagonists, vitamin C analogs and antagonists, vitamin D analogs and antagonists, vitamin E analogs and antagonists, vitamin K analogs and antagonists.

Conjugates: Detecting Agents

In exemplary embodiments, the binding construct is conjugated to a detecting agent. In exemplary embodiments, the detecting agent is capable of emitting a detectable (measurable) signal based on enzymatic activity, radioactivity, chromogenic activity, and/or binding activity. In exemplary embodiments, the signal is radioactive, chromogenic, colorimetric, fluorometric, chemiluminescent, enhanced chemiluminescent, direct fluorescent, time-resolved fluorescent, direct chemiluminescent, phosphorescent, enzymatic, or based on binding of a micro- or nanoparticle, streptavidin/avidin-biotin and protein A. In exemplary embodiments, the detecting agent comprises an enzyme, a radioactive isotope, a DNA reporter, a chromogenic or fluorogenic reporter, or an electrochemiluminescent tag. In exemplary aspects, the enzyme is horseradish peroxidase (HRP), alkaline phosphatase (AP), glucose oxidase, or beta-galactosidase. In exemplary aspects, the enzyme when exposed to certain reagents cause chemiluminescence or light production. In exemplary aspects, the radioisotope is $I^{125}$. In exemplary aspects, the DNA reporter is a DNA probe. In exemplary aspects, the fluorogenic reporter is phycoerythrin (PE), e.g., B-PE, R-PE, or allophycocyanin (APC).

Conjugates: Dimers & Multimers

In some embodiments, the binding construct is provided as a dimer or a multimer in which more than one binding construct of the invention are linked together. The dimer in some aspects is a homodimer comprising two binding constructs of the same type (e.g., same structure) linked together. In alternative aspects, the dimer is a heterodimer comprising two binding constructs of the invention, wherein the two binding constructs are structurally distinct from each other. The multimer in some aspects is a homomultimer comprising more than one binding construct of the invention and each binding construct is of the same type (e.g., same structure). In alternative aspects, the multimer is a heteromultimer comprising more than one binding construct of the invention and wherein at least two binding constructs of the heteromultimer are structurally distinct from the other. In exemplary aspects, the binding construct comprises a dimer, e.g., a homodimer, of two Fab fragments, each Fab fragment of which binds to FIXp and not to WT FIX, e.g., binds to FIXp even in the presence of WT FIX or in a sample comprising human plasma. In exemplary aspects, the homodimer comprising two Fab fragments is bivalent yet monospecific for FIXp. In exemplary aspects, each Fab fragment of the homodimer comprises the amino acid sequence of SEQ ID NOs: 6-11. In exemplary aspects, one or more amino acids are present between each of SEQ ID NOs: 6-11. In exemplary aspects, each Fab fragment of the homodimer comprises the sequence of SEQ ID NO: 24 or SEQ ID NO: 25 or both SEQ ID NOs: 24 and 25. In exemplary aspects, each Fab fragment of the homodimer comprises the sequence of SEQ ID NO: 26 or SEQ ID NO: 27 or both SEQ ID NOs: 26 and 27.

Two or more of the binding constructs can be linked together using standard linking agents and procedures known to those skilled in the art. In certain embodiments, the linker connecting the two (or more) binding constructs is a linker known in the art. In some embodiments, the linker is a disulfide bond. For example, each monomer of the dimer may comprise a sulfhydryl and the sulfur atom of each participates in the formation of the disulfide bond. In some embodiments, the linker is a helix-turn-helix motif. In exemplary aspects, each monomer of the dimer is connected via a helix-turn-helix motif. In exemplary aspects, each monomer of the dimer is connected via an alkaline phosphatase domain.

In exemplary aspects, the homodimer comprising two Fab fragments comprises a linker connecting the two Fab fragments. In exemplary aspects, the homodimer comprises a synthetic double helix loop helix motif, such as that described in Haylock et al., Int J. Oncol. 48(2): 461-470 (2016) or Wang et al., Anal. Chem. 78: 997-1004 (2006). In exemplary aspects, the homodimer comprises a constant antibody domain. Such antibody domains are described in Hu et al., Cancer Res 56: 3055-3061 (1996) and McGregor et al., Mol Immuno 31: 219-226 (1994). In exemplary aspects, the homodimer comprises a bacterial alkaline phosphatase domain, such as that described in Wang et al. (2006), supra. In exemplary aspects, the homodimer comprises the sequence of SEQ ID NO: 28 or SEQ ID NO: 27 or both SEQ ID NOs: 28 and 27.

Nucleic Acids

Further provided herein are nucleic acids comprising a nucleotide sequence encoding any of the binding constructs (e.g., antibodies, antigen-binding fragments, polypeptides, or conjugates) described herein. By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered inter-nucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridme, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouratil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

In some aspects, the nucleic acid encodes only a portion of the antibodies, antigen-binding fragments, polypeptides, or conjugates. For example, when the conjugate comprises a polymer, which does not comprise amino acids and thus is not encoded by a nucleic acid, the nucleic acid encodes only the part of the conjugate which can be encoded by a nucleic acid. In exemplary embodiments, the nucleic acid comprises a nucleotide sequence encoding a polypeptide comprising an amino acid sequence comprising each of SEQ ID NOs: 6-11. In exemplary aspects, the nucleic acid encodes the polypeptide comprising an amino acid sequence comprising each of SEQ ID NOs: 6-11 wherein one or more amino acids are present between each of SEQ ID NOs: 6-11. In exemplary aspects, the nucleic acid encodes the polypeptide which further comprises an expression tag, e.g., a FLAG tag comprising DYKDDDDK (SEQ ID NO: 12) and/or a hexa-His tag comprising HHHHHH (SEQ ID NO: 13).

The nucleic acids are useful in e.g., methods of recombinant production of the binding constructs of the invention.

Recombinant Expression Vector

The nucleic acids of the invention can be incorporated into a recombinant expression vector, or "vector". In this regard, the invention provides recombinant expression vectors or "vectors" comprising any of the nucleic acids of the invention. For purposes herein, the term "recombinant expression vector" or "vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the altered nucleotides or non-naturally occurring internucleotide linkages do not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as AGTIO, AGTI 1, AZapll (Stratagene), AEMBL4, and ANMI 149, also can be used. Examples of plant expression vectors include pBIO1, pBI101.2, pBI101.3, pBI121 and pBIN19 (Clontech). Examples of animal expression vectors include pEUK-CI, pMAM and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2 p plasmid, A, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can comprise a native or normative promoter operably linked to the nucleotide sequence encoding the polypeptide (including functional portions and functional variants thereof), or to the nucleotide sequence which is complementary to or which hybridizes to the nucleotide sequence encoding the polypeptide. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

Host Cells

The invention further provides a host cell comprising any of the nucleic acids or recombinant expression vectors described herein. As used herein, the term "host cell" refers to any type of cell that can contain and express the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5a cell. For purposes of producing a recombinant polypeptide the host cell is preferably a mammalian cell, e.g., a CHO cell.

Kits

Provided herein are kits comprising any one or more of the binding constructs of the present disclosure. In exemplary embodiments, the kit comprises an antibody or antigen-binding fragment or polypeptide or conjugate or nucleic acid or vector or host cell, as described herein or a combination of any of the foregoing. In exemplary aspects, the binding construct is provided in the kit in a predetermined amount or concentration. For example, the kit may be a detection kit comprising a predetermined amount of the binding construct for detecting FIX Padua in a sample. In exemplary embodiments, the one or more of the binding constructs of the present disclosure is provided in the kit in an aqueous solution. In exemplary aspects, the aqueous solution is provided to the end-user on dry ice. In some aspects, the aqueous solution is provided to the end-user separately from the other components of the kit. In exemplary embodiments, the binding constructs of the present disclosure are provided in the kit in a lyophilized or other freeze-dried form. In exemplary aspects, the binding constructs of the present disclosures are provided in the kit in a frozen or cryopreserved form. In exemplary aspects, the concentration of the antibody or antigen-binding fragment or polypeptide or conjugate provided in the kit is about 1-10 µg/mL or about 1-5 µg/mL. In exemplary aspects, the concentration of the antibody or antigen-binding fragment or polypeptide or conjugate provided in the kit is about 1.5 µg/mL to about 2.0 µg/m L.

In exemplary aspects, the kit comprises a solid support, and in exemplary aspects the antibody or antigen-binding fragment or polypeptide or conjugate is pre-coated onto the solid support. In exemplary aspects, the kit comprises a solid support selected from the group consisting of a tube, a dish, a flask, a bag, a plate (e.g., a microtiter plate), a membrane, a filter, a bead, a fiber, a probe, and the like. In exemplary aspects, the solid support is made of a polymer. In exemplary aspects, the solid support is made of agarose, cellulose, dextran, polyacrylamide, latex, or controlled pore glass. In exemplary aspects, the solid support is made of agarose. In exemplary aspects, the solid support is made of polyvinyl difluoride (PVDF), nitrocellulose, nylon 66, protran nitrocellulose, or paper. In exemplary aspects, the membrane is one of the Immobilon®, Protran®, QuickDraw®, Westran®, Whatman® or Hybond® membranes (Sigma-Aldrich, St. Louis, Mo.). In exemplary aspects, the solid support is a polymer bead, a microtiter plate, a membrane or a filter. In exemplary aspects, the kit comprises a solid support pre-coated with a solution comprising about 100 ng or more, about 150 ng or more, about 200 ng or more, about 500 ng or more of the antibody or antigen-binding fragment or polypeptide or conjugate. In certain aspects, the kit comprises a solid support pre-coated with a solution comprising about 50 ng to about 550 ng, about 100 ng to about 500 ng, about 125 ng to about 400 ng, about 150 ng to about 350 ng, about 175 ng to about 300 ng, or about 200 ng to about 250 ng of the antibody or antigen-binding fragment or polypeptide or conjugate. In certain aspects, the kit comprises a solid support pre-coated with a solution comprising about 100 ng to about 150 ng, about 150 ng to about 200 ng, about 200 ng to about 500 ng of the antibody or antigen-binding fragment or polypeptide or conjugate. In exemplary aspects, the kit comprises a solid support comprising pre-aliquoted amounts of the antibody or antigen-binding fragment or polypeptide or conjugate. In exemplary aspects, the kit comprises a microtiter plate, wherein each well of the microtiter plate comprises a solution comprising about 100 µL to about 500 µL of a solution comprising about 1-10 µg/mL or about 1-5 µg/mL of the antibody or antigen-binding fragment or polypeptide or conjugate. In exemplary aspects, the kit comprises a microtiter plate, wherein each well of the microtiter plate comprises a solution comprising about 100 µL to about 500 µL of a solution comprising about 2.5 µg/mL of the antibody or antigen-binding fragment or polypeptide or conjugate.

In exemplary aspects, the kit comprises additional reagents, substrates, solvents, buffers, diluents, etc., used in the detection methods described herein. In exemplary aspects, any one or more of the additional components are provided in the kit in a predetermined amount, e.g., the amount necessary and suitable for a detection assay. In exemplary aspects, the kit comprises a secondary antibody which binds to the FIX Padua-binding antibody, antigen-binding fragment, polypeptide or conjugate. In exemplary aspects, the secondary antibody comprising a detecting agent. In exemplary embodiments, the detecting agent comprises an enzyme, a radioactive isotope, a DNA reporter, a chromogenic or fluorogenic reporter, or an electrochemiluminescent tag. The detecting agent can be any of the detecting agents described herein. In exemplary aspects, the secondary antibody or the FIX Padua-binding antibody, antigen-binding fragment, polypeptide or conjugate is attached to a detecting agent.

Compositions

Provided herein are compositions comprising any one or more of the binding constructs of the present disclosure. In exemplary aspects, the composition comprises a binding construct as described herein admixed with a detecting agent. In exemplary aspects, the detecting agent is any detecting agent described herein. See the section entitled "Conjugates: Detecting Agents".

In exemplary aspects, the composition comprises a binding construct as described herein admixed with a biological sample obtained from a subject. In exemplary aspects, the biological sample is any biological sample described herein. See the section entitled "Samples". In exemplary aspects, the composition comprises an antibody or antigen-binding fragment or polypeptide or conjugate, as described herein, admixed with a biological sample comprising human plasma, or a diluted fraction thereof. In exemplary aspects, the composition comprises an antibody or antigen-binding fragment or polypeptide or conjugate, as described herein, admixed with a biological sample comprising human tissue, or cells thereof. In exemplary aspects, the biological sample comprises liver tissue. In exemplary aspects, the composition further comprises a detecting agent.

Compositions comprising any one or more of the binding constructs of the present disclosure admixed with a sample, e.g., a biological sample, comprising human plasma proteins is further provided herein. In exemplary aspects, the composition comprises an antibody or antigen-binding fragment or polypeptide or conjugate, as described herein, admixed with at least one of the human plasma proteins selected from the group consisting of Factor IX, Factor II, and Factor X, and variants thereof. In exemplary aspects, the composition further comprises a detecting agent.

Detection Methods

Binding constructs provided herein are useful in, e.g., detection methods that allow for unambiguous or specific detection of FIX Padua in samples, e.g., clinical samples comprising, e.g., FIX Padua and WT FIX. The binding constructs can be used in any antibody-based assay or technique or any immunoassay known in the art, such as, but not limited to, radioimmunoassay (RIA), magnetic immunoassay (MIA), immunocytochemical (ICC) assays, immunohistochemical (IHC) assays, immunofluorescent assays, ELISA, EIA, ELISPOT, enzyme multiplied immunoassay, radiobinding assay, Western blotting, immunoprecipitation, dot blots, flow cytometry, real-time immunoquantitative PCR, protein microarrays and the like. See, e.g., *The Immunoassay Handbook* (Fourth Edition); Theory and Applications of Ligand Binding, ELISA and Related Techniques, ed. Wild, Elsevier Ltd. (Oxford, UK) 2013, Green and Sambrook, *Molecular Cloning: A Laboratory Manual*, 4th ed., Cold Spring Harbor Laboratory Press (Cold Spring Harbor, N.Y.) 2012, and *Immunoassay*, Diamandis and Christopolous, Academic Press 1996.

Accordingly, provided herein are uses of the binding construct (e.g., antibody or antigen-binding fragment, polypeptide, or conjugate), nucleic acid, vector, host cell, and/or kit described herein for detecting Factor IX Padua in a sample. In exemplary aspects, the sample is a biological sample that has been obtained from a subject who has been administered an expression vector comprising a nucleic acid encoding FIX Padua. For example, in various embodiments, the subject is suffering from a bleeding disorder and is undergoing Factor IX replacement therapy, optionally achieved by expression of a nucleic acid comprising a nucleotide sequence encoding a heterologous Factor IX Padua.

Also provided herein are methods of detecting Factor IX Padua in a sample obtained from a subject. In exemplary embodiments, the method comprises (i) contacting the sample with a binding construct (e.g., an antibody or antigen-binding fragment or polypeptide or conjugate) as described herein to form a complex (e.g., an immunocomplex) comprising FIX Padua and the binding construct (e.g., antibody, antigen-binding fragment, polypeptide, or conjugate), and (ii) detecting the complex.

In exemplary embodiments, the FIX Padua comprises the amino acid sequence of SEQ ID NO: 1.

In exemplary embodiments, detecting the complex comprises detecting a signal of a detecting agent. In exemplary embodiments, the signal is based on enzymatic activity, radioactivity, chromogenic activity, and/or binding activity. In exemplary embodiments, the signal is radioactive, chromogenic, colorimetric, fluorometric, chemiluminescent, enhanced chemiluminescent, direct fluorescent, time-resolved fluorescent, direct chemiluminescent, phosphorescent, enzymatic, or based on binding of a micro- or nanoparticle, streptavidin/avidin-biotin and protein A. In exemplary embodiments, the detecting agent comprises an enzyme, a radioactive isotope, a DNA reporter, a chromogenic or fluorogenic reporter, an electrochemiluminescent tag. In exemplary embodiments, detecting the complex comprises carrying out surface plasmon resonance to detect the complex or measuring change in resistance on an electrode (as FIX Padua binds to the antibody, antigen-binding fragment, polypeptide, or conjugate). See, Gonzalez-Diaz et al., "Plasmonic Au/Co/Au nanosandwiches with Enhanced Magneto-Optical Activity" Small 4(2): 202-5 (2008) and Tsekenis (2008). "Label-less immunosensor assay for myelin basic protein based upon an ac impedance protocol." Analytical Chemistry 80 (6): 2058-62 (2008). In exemplary aspects, the enzyme is horseradish peroxidase (HRP), alkaline phosphatase (AP), glucose oxidase, or beta-galactosidase. In exemplary aspects, the enzyme is exposed to reagents which cause them to chemiluminesce or produce light. In exemplary aspects, the radioisotope is 1125. In exemplary aspects, the DNA reporter is a DNA probe. See, e.g., Rajkovic, "Immunoquantitative real-time PCR for detection and quantification of *Staphylococcus aureus* enterotoxin B in foods." Applied and Environmental Microbiology 72 (10): 6593-9 (2006); and Gofflot "Immunoquantitative polymerase chain reaction for detection and quantitation of prion protein." Journal of Immunoassay and Immunochemistry 25 (3): 241-58 (2004). In exemplary aspects, the fluorogenic reporter is phycoerythrin (PE) e.g., B-PE, R-PE, or allophycocyanin (APC).

In exemplary embodiments, the antibody or antigen-binding fragment or polypeptide is conjugated to a detecting agent. In exemplary embodiments, the conjugate comprises a detecting agent. In exemplary embodiments, the antibody or antigen-binding fragment or polypeptide is not conjugated to a detecting agent or the conjugate does not comprises a detecting agent. In such exemplary embodiments, the methods comprise contacting the sample with a secondary antibody comprising a detecting agent, wherein the secondary antibody binds to the antibody or antigen-binding fragment or polypeptide or conjugate. The secondary antibody may be any antibody of any isotype or class, provided that the secondary antibody will bind to the anti-FIX Padua antibody, antigen-binding fragment thereof, polypeptide or conjugate.

In exemplary embodiments, the antibody or antigen-binding fragment or polypeptide is conjugated to a solid support. In exemplary embodiments, the conjugate comprises a solid support. For example, the solid support is selected from the group consisting of a tube, a dish, a flask, a bag, a plate (e.g., a microtiter plate), a membrane, a filter, a bead, a fiber, a probe, and the like. In exemplary aspects, the solid support is made of a polymer. In exemplary aspects, the solid support is made of agarose, cellulose, dextran, polyacrylamide, latex, or controlled pore glass. In exemplary aspects, the solid support is made of agarose. In exemplary aspects, the solid support is made of polyvinyl difluoride (PVDF), nitrocellulose, nylon 66, protran nitrocellulose, or paper. In exemplary aspects, the membrane is one of the Immobilon®, Proton®, QuickDraw®, Westran®, Whatman® or Hybond® membranes (Sigma-Aldrich, St. Louis, Mo.). In exemplary aspects, the solid support is a polymer bead, a magnetic or paramagnetic bead, a microtiter plate, a membrane or a filter.

Subjects

In exemplary embodiments, the subject referenced herein is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In exemplary aspects, the mammal is a human. In exemplary aspects, the human subject is an adult, e.g., 18 years or older, or an adolescent. In exemplary aspects, the subject has been administered an expression vector comprising a nucleotide sequence encoding FIX Padua comprising the amino acid sequence of SEQ ID NO: 1. In exemplary aspects, the subject has a bleeding disorder. In exemplary aspects, the subject has a bleeding disorder in which the subject's blood does not clot properly. In exemplary aspects, the subject has a lack of expression or a low expression level of Factor IX, e.g., WT Factor IX. In exemplary aspects, the subject has a mutation in the gene encoding Factor IX. In exemplary aspects, the subject suffers from hemophilia, e.g., hemophilia B (also known as Christmas Disease). In exemplary aspects, the subject exhibits a higher than normal clotting activity. In exemplary aspects, the subject has a naturally-occurring FIX Padua, e.g., has a gene mutation leading to expression of FIX Padua.

Samples

In exemplary embodiments, the sample referenced herein is a biological sample comprising one or more bodily fluids, e.g., human bodily fluids. In exemplary aspects, the sample comprises a bodily fluid, including, but not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In exemplary aspects, the sample comprises blood, plasma, or serum. In exemplary aspects, the sample is prepared from blood, plasma, or serum. In exemplary aspects, the sample is a fraction of blood, plasma, or serum. In exemplary aspects, the sample is a blood sample, a plasma sample, or a serum sample. In exemplary aspects, the sample comprises blood or a fraction thereof (e.g., plasma, serum). In exemplary aspects, the sample comprises or is plasma.

In exemplary aspects, the sample is a human tissue sample. In exemplary aspects, the human tissue sample comprises muscle tissue, epithelial tissue, connective tissue, or nervous tissue. In exemplary aspects, the human tissue sample comprises bone tissue. In exemplary aspects, the human tissue sample comprises heart tissue, spleen tissue, lymph node tissue, brain tissue, spinal cord tissue, nerve tissue, ear, nose or eye tissue, breast tissue, subcutaneous tissue, mammary gland tissue, myeloid tissue, lymphoid tissue, nasopharynx tissue, larynx tissue, tracheal tissue brochus tissue, lung tissue, skin tissue, salivary gland tissue, tissue from the tongue or mouth, oropharynx tissue, larngopharynx tissue, esophagus tissue, stomach tissue, small intestine tissue, appendix tissue, colon tissue, rectal tissue, anal tissue, liver tissue, biliary tract tissue, pancreas tissue, gall bladder tissue, kidney tissue, ureter tissue, bladder tissue, urethra tissue, uterine tissue, vaginal tissue, vulvar tissue, ovary tissue, placenta tissue, scrotum tissue, penis tissue, prostate tissue, testicle tissue, seminal vesicle tissue, pituitary tissue, pineal tissue, thyroid tissue, parathyroid tissue, adrenal tissue, or islet of Langerhans tissue. In exemplary aspects, the human tissue sample comprises liver tissue or spleen tissue or kidney tissue. In exemplary aspects, the human tissue sample comprises liver tissue.

The following examples are given merely to illustrate the present invention and not in any way to limit its scope.

EXAMPLES

Example 1

This example demonstrates a method of making an antibody or antigen-binding fragment thereof of the invention.

A phage display method was used to select candidate specific FIX Padua binding construct. The phage library was screened using a linear peptide that enclosed the single amino acid substitution at position 338, a structural peptide that enclosed the single amino acid substitution at position 338, or a full-length recombinant FIX Padua to capture candidates. Three rounds of panning, with and without competition with wild-type FIX sequences, led to the identification of several candidate binding constructs. BIACORE and ELISA experiments were performed to determine the specificity and affinity of the candidates obtained.

One candidate (termed BC1) was obtained with a linear peptide comprising the sequence DRATCLLSTKFT and two candidates (termed BC2 and BC3) were obtained with a structural peptide comprising the sequence LVDRATCLL-STKFTIYNNMFCAGFH. Yet another candidate (BC4) was obtained with a peptide comprising a linear peptide or a structural peptide alternating with FIX Padua.

Screening assays demonstrated that the candidates bind to FIX Padua. For BC2 and BC3 the binding signal (fold over background) to wild-type FIX was less than 11 while the binding signal (fold over background) to FIX Padua was over 71. For BC1, the binding signal (fold over background) to wild-type FIX was 1, while the binding signal to FIX Padua was nearly 200. In a second set of screening assays, the binding signal to wild-type FIX was 1 or less for each of BC1, BC2, and BC3, while the binding signals for BC1, BC2, and BC3 to FIX Padua were 70, 30, and 10, respectively. BC4 demonstrated a binding signal to FIX Padua of more than 36, while the signal to wild-type FIX was about 1.

The binding of BC1 to FIX Padua was tested via ELISA on $Ni^{2+}$ plates in which coating concentrations of BC1 as well as concentrations of the FIX Padua were varied. The concentrations of BC1 and FIX Padua tested were 0.04 μg/ml, 0.2 μg/ml, 1 μg/ml, and 5 μg/ml. The binding signals of BC1 to FIX Padua were compared to a wt FIX control. At each concentration tested, the binding of FIX Padua to BC1 was greater than the binding of WT FIX to BC1 (FIG. 2).

Figure 3:
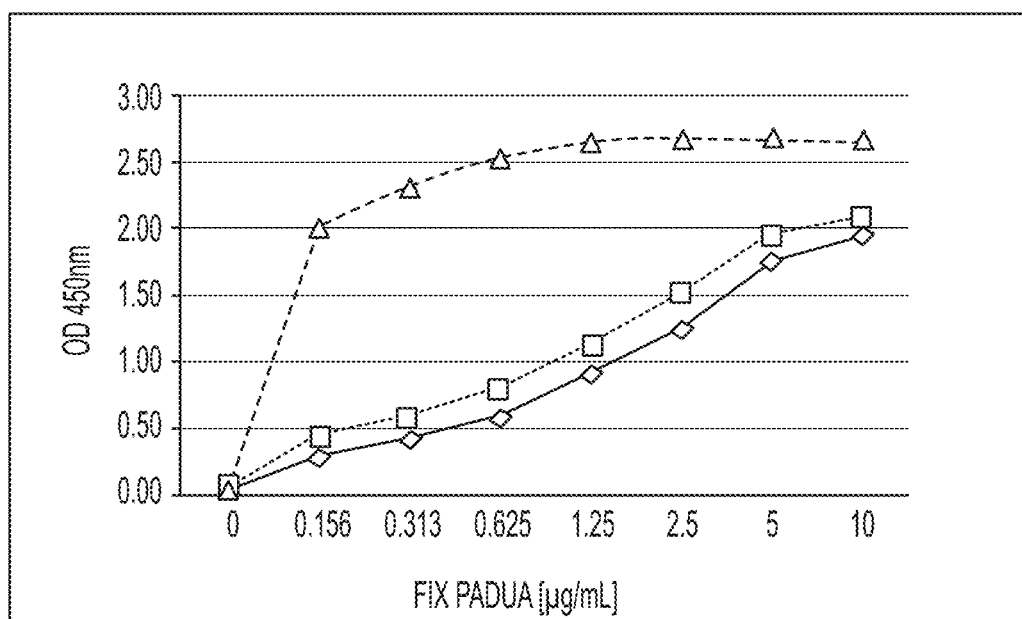
FIG. 3 represents a graph of the binding signals of BC1 (triangles), BC2 (diamonds), or BC3 (squares) coated on MaxiSorp plates to the indicated concentration of FIX Padua.
Figure 10:
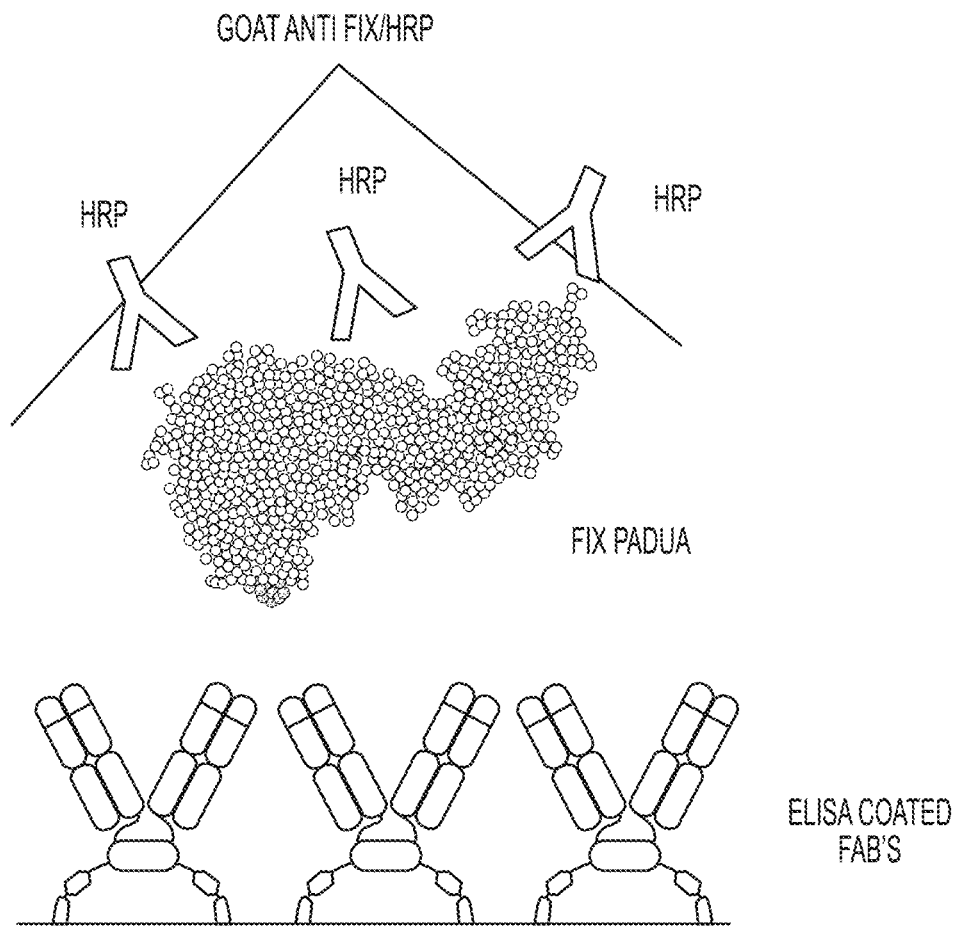
FIG. 10 represents a schematic of the components of the ELISA described in Example 1.

The binding of BC1, BC2, and BC3 to FIX Padua in the presence of wild-type FIX was tested via ELISA (as shown in FIG. 10). MaxiSorp plates were coated with 5 μg/mL of BC1, BC2, or BC3 and solutions containing FIX Padua at varying concentrations and 5 μg/mL wild-type FIX were added to the coated plates. The FIX Padua concentrations tested were 0 μg/mL, 0.156 μg/mL, 0.313 μg/mL, 0.625 μg/mL, 1.25 μg/mL, 2.5 μg/mL, 5 μg/mL, and 10 μg/mL. As shown in FIG. 3, BC1 demonstrates a strong affinity for FIX Padua, even in the presence of WT Factor IX. BC1 demonstrated the highest sensitivity in the presence of 5 μg/mL WT Factor IX.

Figure 4:
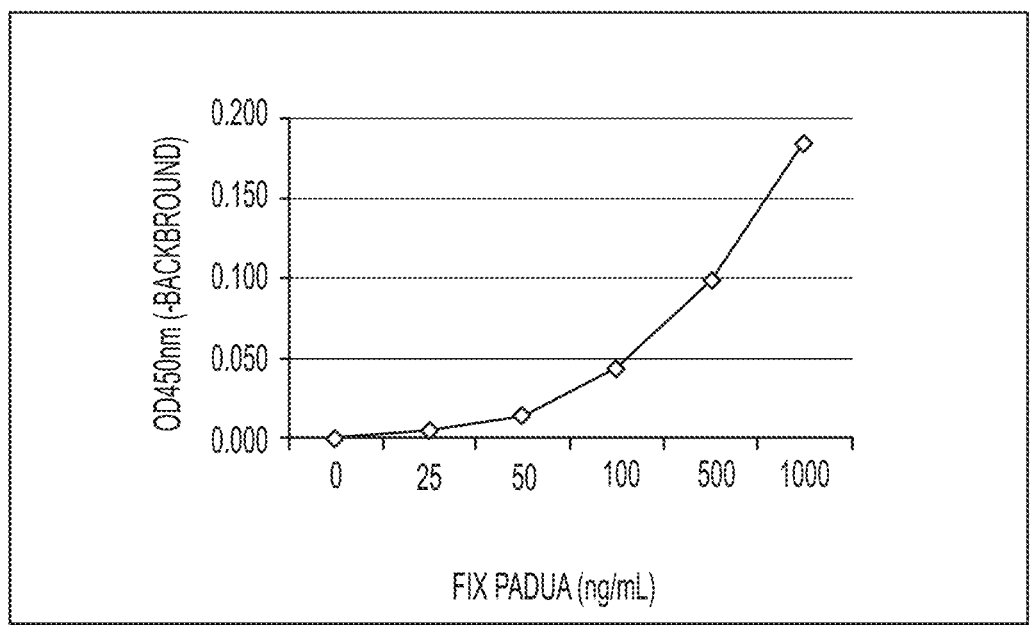
FIG. 4 represents a graph of the binding signals of BC1 to the indicated concentration of FIX Padua in 5% human plasma solution containing 5 μg/ml WT Factor IX without benzamidine.

The binding of BC1 to varied concentrations of FIX Padua in the presence of 5% human plasma and 5 μg/mL WT Factor IX was tested via ELISA (as shown in FIG. 10). As shown in FIG. 4, BC1 binding to FIX Padua increases as the concentration of FIX Padua increases, even in the presence of WT Factor IX and other plasma proteins. FIX Padua was varied from 25 ng/ml to 1000 ng/ml.

Figure 5:
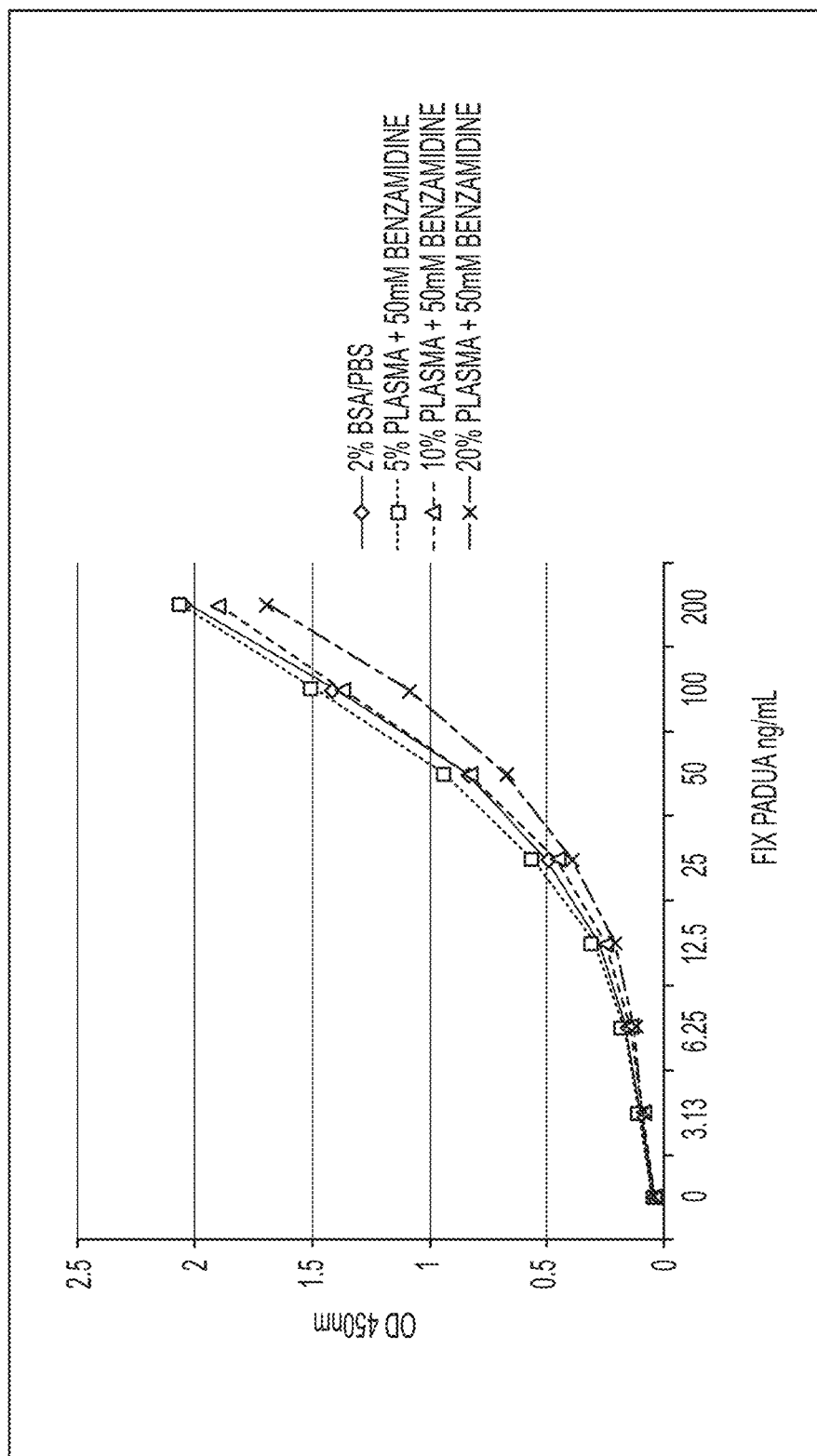
FIG. 5 represents a graph of the binding signals of BC1 to the indicated concentration of FIX Padua in 2% BSA/PBS (diamonds), 5% plasma solution containing 50 mM benzamidine (squares), 10% plasma solution containing 50 mM benzamidine (triangles), or 20% plasma solution containing 50 mM benzamidine (Xs).

The binding of BC1 to FIX Padua in varying % plasma solutions containing 50 mM benzamidine was tested via ELISA (as shown in FIG. 10). The solutions were 5%, 10%, or 20% (v/v) plasma. As shown in FIG. 5, BC1 could detect FIX Padua in the range of 3.13 ng/ml to 200 ng/ml in the 20% plasma solution.

Figure 6:
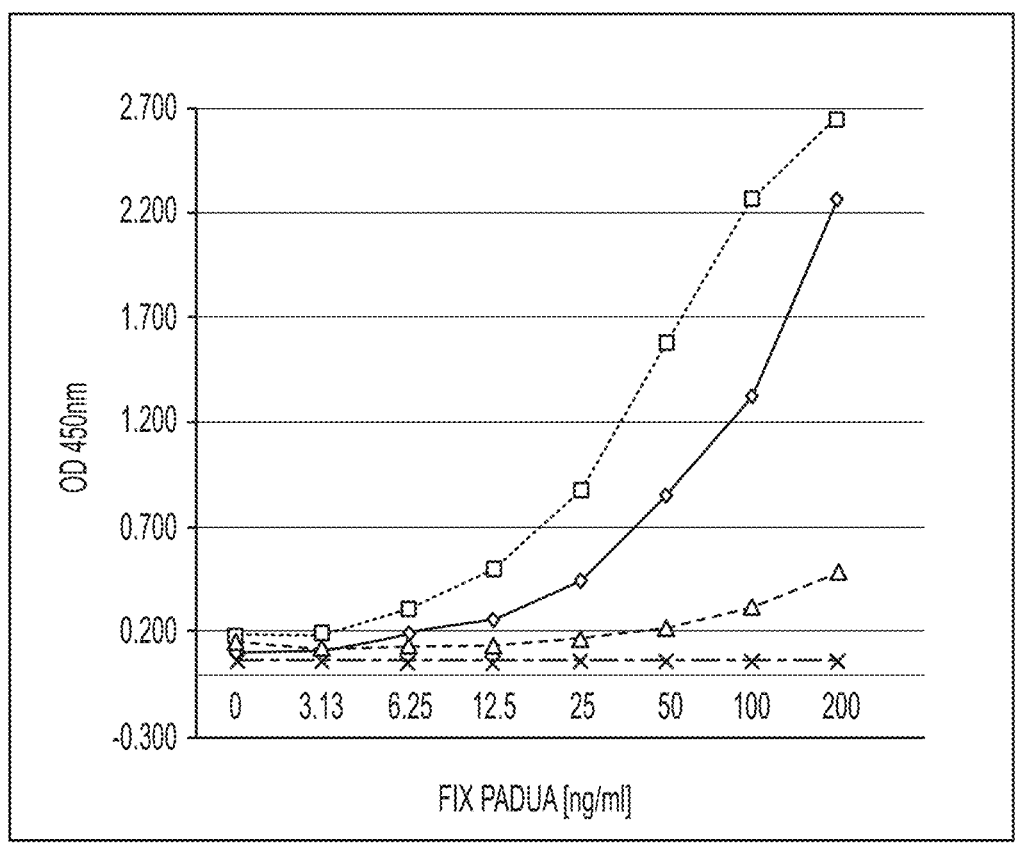
FIG. 6 represents a graph of the binding signals of BC1 (squares), BC2 (triangles), BC4 (diamonds), or a negative control (Xs) to the indicated concentration of FIX Padua in a 20% (v/v) plasma solution comprising WT Factor IX and 50 mM benzamidine.

The binding of BC1, BC2, and BC4 to FIX Padua in the presence of 20% human plasma containing 5 µg/mL WT Factor IX was tested by ELISA. The concentrations of FIX Padua used in this assay were 0, 3.13, 6.25, 12.5, 25, 50, 100 and 200 ng/ml. As shown in FIG. 6, BC1 exhibited the highest sensitivity, while BC2 exhibited the lowest sensitivity and failed to bind to FIX Padua in the 20% human plasma sample containing 5 µg/mL WT Factor IX. BC4 demonstrated a binding ability to FIX Padua lower than that of BC1 (FIG. 6). Like BC2, BC3 failed to function as a FIX Padua-specific detection antibody in a 20% human plasma containing sample (data not shown).

Figure 7:
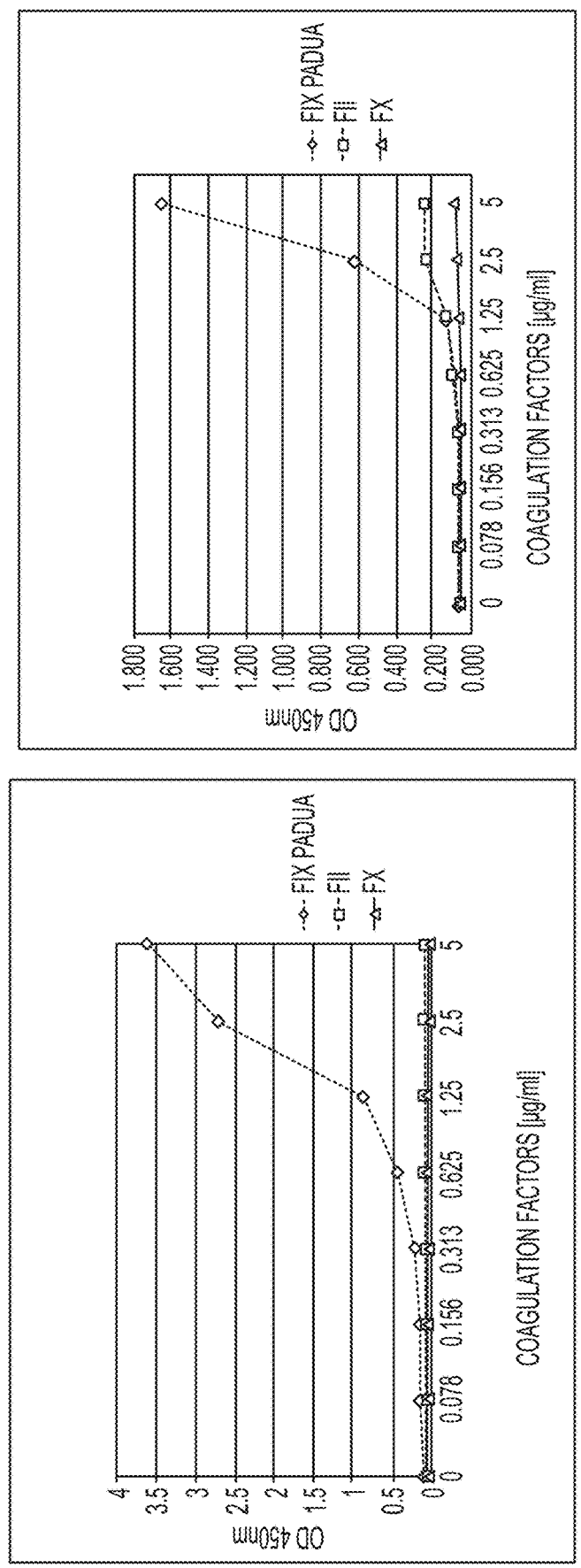
FIG. 7 represents two graphs of the binding signals of BC1 (left panel) and BC4 (right panel) to the indicated concentration of coagulation factors: FIX Padua (diamonds); Factor II (squares); and Factor X (triangles).

The binding of BC1 and BC4 to other coagulation factors were tested via ELISA. In specific, the binding of BC1 or BC4 to Factor II and Factor X were tested. As shown in FIG. 7, the binding of BC1 was highly specific for FIX Padua, showing no cross-reactivity against Factor II or Factor X, whereas BC4, in contrast, demonstrated a slight cross-reactivity to Factor II.

Figure 8:
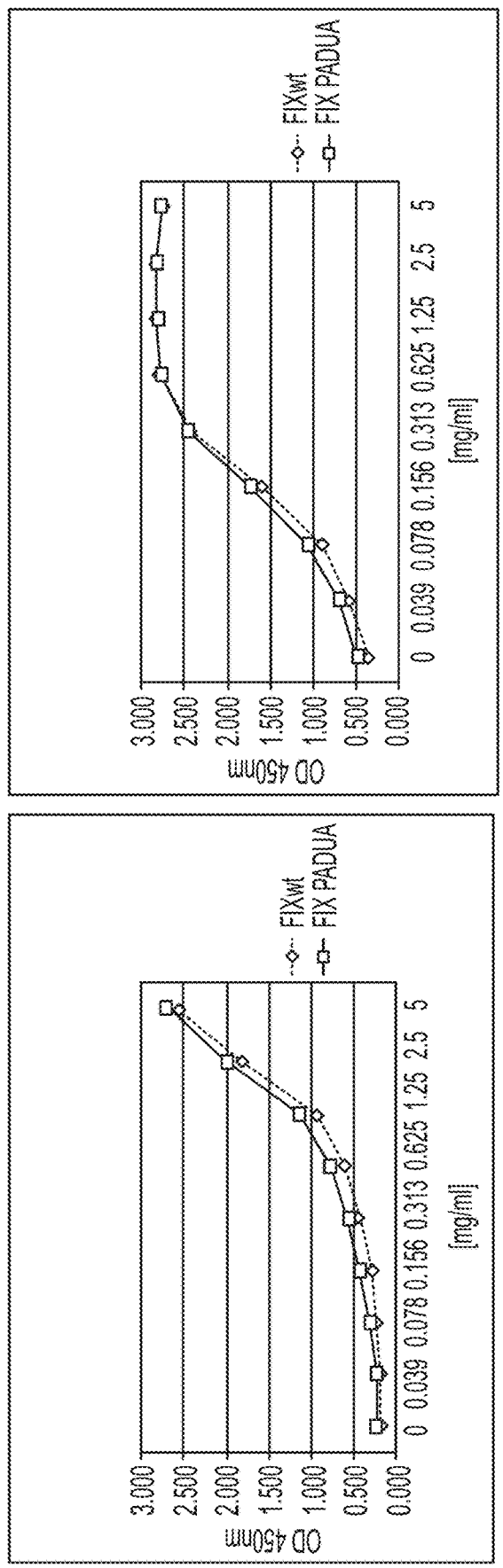
FIG. 8 represents two graphs of the binding signals of BC5 (left panel) and BC6 (right panel) to the indicated concentrations (μg/ml) of WT Factor IX (diamonds) or to FIX Padua (squares).

The binding of BC1 was specific for FIX Padua. In contrast, two other binding constructs (BC5 and BC6) were made via phase display using the structural peptide. As shown in FIG. 8, the binding of BC5 and BC6 was not specific for FIX Padua, since significant binding to WT FIX was demonstrated.

The KD value for BC1 was determined via Biacore surface plasmon resonance. The KD of BC1 was 56 nM. BC1 demonstrated the highest affinity for FIX Padua than the other candidates. That value is similar to, if not better than, the KD (M) values of commercial antibodies. For example, the KD(M) value of a commercially available sheet anti-human wild-type FIX antibody is $3.11 \times 10^{-9}$.

The sequences of the CDRs of the heavy and light chains of BC1 were determined by PCR followed by translation of the sequence and the sequences are as follows:

```
Heavy Chain CDR1
                              SEQ ID NO: 6
SSYAIS

Heavy Chain CDR2
                              SEQ ID NO: 7
GIVPAFGTANYAQKFQG

Heavy Chain CDR3
                              SEQ ID NO: 8
SWGVISFAY

Light Chain CDR1
                              SEQ ID NO: 9
RASQDISSYLN

Light Chain CDR2
                              SEQ ID NO: 10
AASNLQS

Light Chain CDR3
                              SEQ ID NO: 11
MQYDSLPFTF
```

BC1 obtained with the linear peptide provided a unique and specific FIX Padua binding and this activity was confirmed. BC1 exhibited a detection limit of ~3 ng/mL plasma and showed no cross reactivity to wild-type FIX even at highly elevated (>5 µg/mL) concentrations.

These data support that a highly specific anti-FIX Padua antibody was generated. This antibody binds to FIX Padua and not any of WT Factor IX, Factor II and Factor X in human plasma samples. These data support that this antibody can be used, e.g., for the development of clinical assays to selectively distinguish between wild-type FIX and FIX Padua antigen levels.

Example 2

This example demonstrates a method of using an antibody or antigen-binding fragment thereof of the invention.

Figure 9:
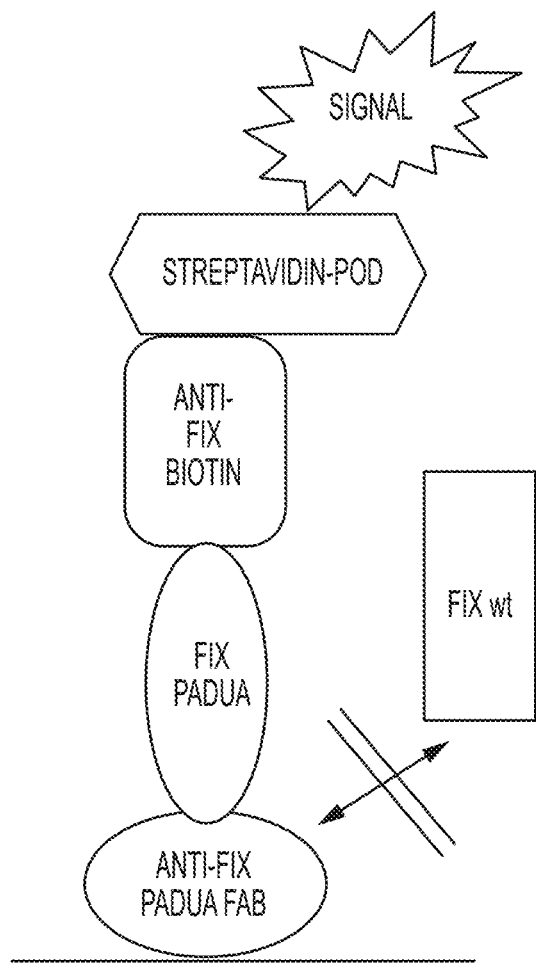
FIG. 9 represents a schematic of the components of the ELISA described in Example 2.

The Fab fragment of a newly developed Factor IX Padua (FIXp)-specific binding antibody (BC1) was coated on 96-well microplates at 2 µg/mL using standard conditions. A commercially-available biotinylated polyclonal sheep anti-human FIX IgG and streptavidin-peroxidase were used as a detection system. A schematic of the assay components is shown in FIG. 9.

Assay calibration was obtained by generating a six-point calibration curve with a FIXp preparation, covering a FIXp concentration range from 27.1-0.85 ng/mL. Patients' samples were diluted with HEPES/NaCl buffer containing 5 mg/mL bovine serum albumin, 10 mM benzamidine, 10 mM $CaCl_2$) and 0.05% Tween 20.

Normal human plasma or purified human FIX showed no signals in the FIXp-specific ELISA. Accurate calibration curves were obtained. FIXp spiked to 1/10-diluted normal human plasma showed acceptable recoveries with dilution response curves parallel to that obtained for the assay standard in buffer. Importantly, the analysis of samples of six patients treated with an expression vector encoding FIXp demonstrated highly similar FIXp protein and FIX activity curves over time, and the samples of cross-reactive material positive (CRM+) patients showed no increased signals for FIXp protein compared to CRM− patients, indicating the specificity of the assay.

The FIXp-specific ELISA allows additional monitoring of treatment outcome by the measurement of the FIXp protein.

Example 3

This example demonstrates a selective ELISA for FIX Padua and the use of the ELISA for testing human plasma samples.

A preparation of BC1 (0.94 mg/mL) was diluted 1/500 with 0.1 M $NaHCO_3$—$Na_2CO_3$, pH 9.5 and bound to the wells of a Maxisorp F96 plate by incubating 100 µL/well at 0 to +10° C. overnight. The dilution buffer (DB), used for the dilution of the samples and the reagents as well as for the blocking of the plates, was 0.1 M Hepes, 0.1 M NaCl, pH 7.2, containing 5 mg/mL biotin-free bovine serum albumin (BSA), 10 mM $Ca^{2+}$, 0.05% Tween 20 (Bio-Rad, EIA grade) and 10 mM benzamidine. After coating, the plate was washed with phosphate-buffered saline containing 0.05% Tween 20 and the wells were blocked by incubation with 200 µL DB/well at room temperature (RT, 18 to 26° C.) for 60 min. The blocking step was terminated by washing. Then the dilutions of the standard/samples were loaded, preparing the serial 1+1 dilution series directly on the plate. The dilutions (100 µL/well) were incubated with the plate at RT for 60 min. Then the plate was washed again and the biotinylated polyclonal sheep anti-human FIX detection antibody, prepared from F9-1030A (CoaChrom) was added (100 µL/well; working dilution 1/500). After an incubation at RT for 60 min, the plate was washed again, streptavidin peroxidase (DakoCytomation) was added (100 µL/well; dilution 1/4,000) and incubated at RT for 30 min. After a final, extensive washing procedure, bound peroxidase activity was measured with the ready-to-use peroxidase substrate SureBlue, stopping the reaction with 3 N sulfuric acid. The plate was then measured at 450 nm with an ELISA reader, subtracting the results obtained at 620 nm.

Figure 11:
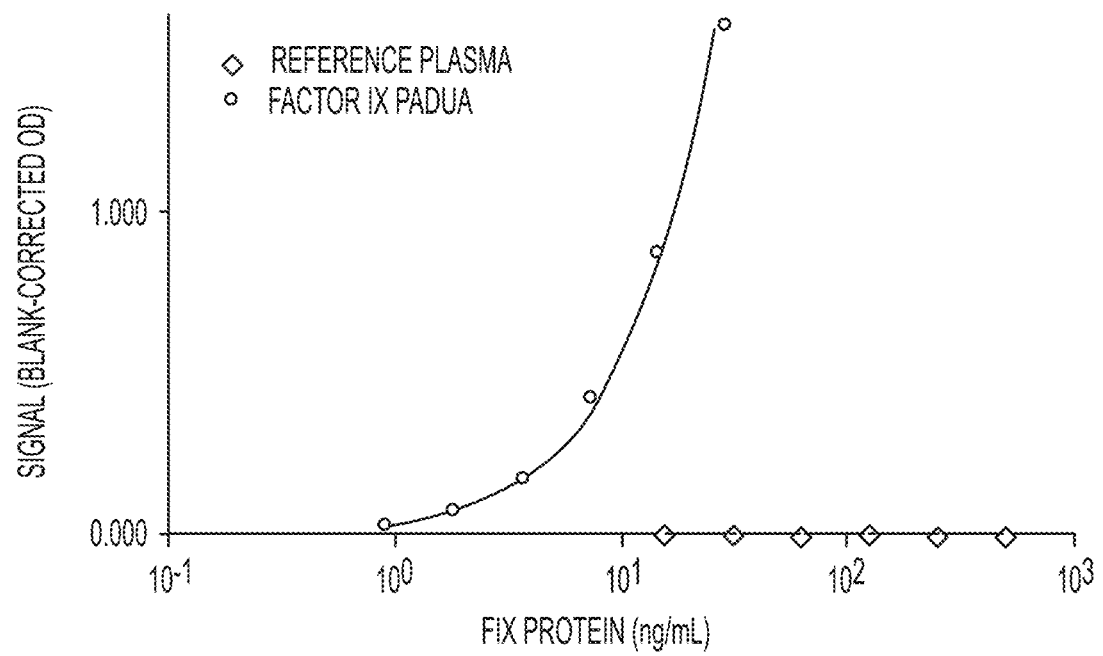
FIG. 11 represents a graph of concentration-response curves of the FIX Padua ELISA using a sample containing FIX Padua (circles) or a reference human plasma sample (diamonds).

FIG. 11 shows the concentration-response curves obtained for a purified human FIX Padua preparation and a fresh-frozen control plasma preparation (CRYOCheck; Precision Biologics) with a WT FIX concentration of 5 µg/m L.

The dose-response curve obtained for the recombinant human FIX Padua concentration covering a range from 29 to 0.91 ng/mL met accepted requirements for accuracy, precision and linearity and was thus deemed to be appropriate for extrapolating samples. In particular, the correlation coefficient of the log-log regression curve was 0.9985 with a mean accuracy of 101.4% and a precision of 7.0%. Accuracy and precision were calculated by back-fitting the signals measured for the six concentrations of the calibration curve. The data furthermore demonstrated the absolute specificity of the approach for FIX Padua: Human reference plasma, containing FIX wt at the normal plasma concentration of 5 µg/mL and measured using the minimum dilution of 1/10, did not elicit any signal.

Figure 12:
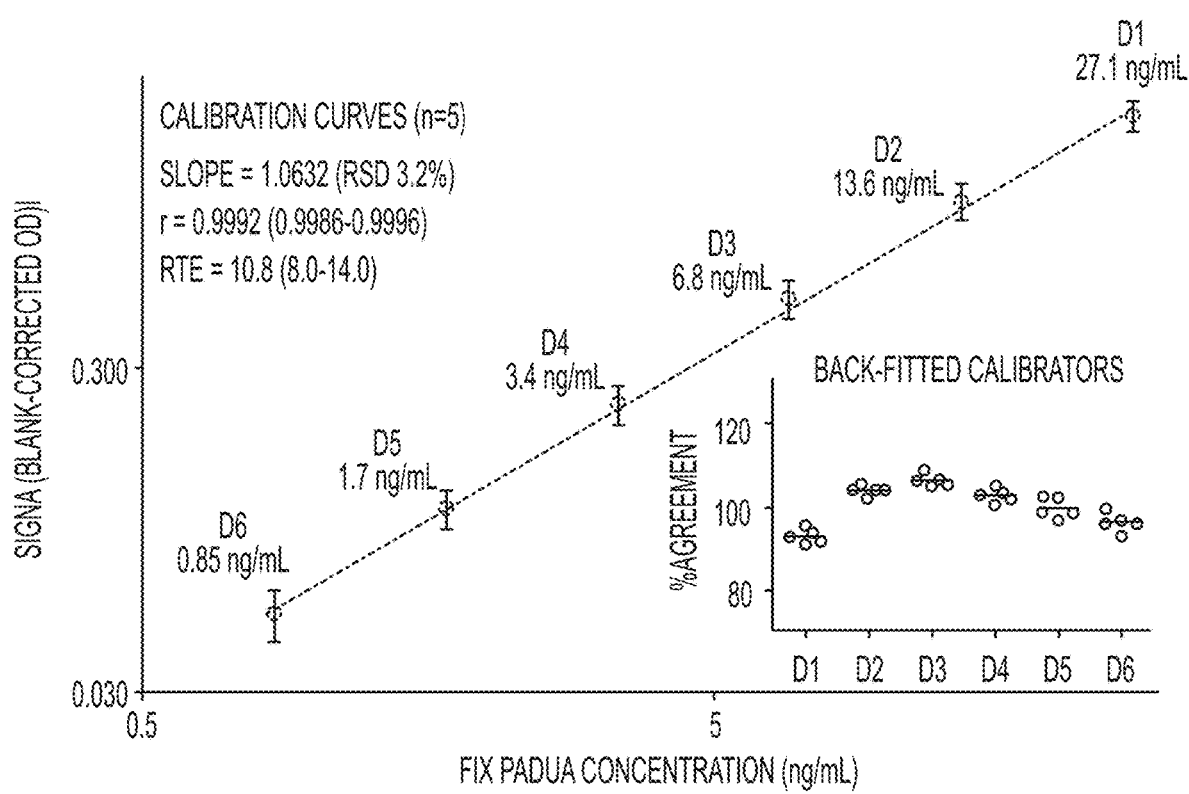
FIG. 12 represents a graph of a calibration curve of the FIX Padua ELISA using six standards of the indicated amounts of FIX Padua (standards D1 to D6).

The ELISA was carried out as described above. Calibration curves were obtained using another recombinant human FIX Padua preparation with a protein concentration of 542.42 µg/ml. The specific clotting activity of 2310 IU/mg protein clearly classified this preparation as the hyperactive FIX Padua variant. The serial dilution series ranged from 1/20,000 to 1/640,000 and defined a FIX concentration range from 27.1-0.85 ng/mL. FIG. 12 shows the mean calibration curve, obtained as the linear regression curves between the logarithms of the blank-corrected mean signals and the FIX concentrations of the six assay standards. The insert shows the agreement of the back-fitted assay calibrators D1 top D6 with their respective nominal concentrations. The calibration curves for FIX Padua showed a good linearity in the concentration range from 27.1 to 0.85 ng/mL. This was shown by the mean correlation coefficient r=0.9992 (range: 0.9986-0.9996) and supported by the back-fitted concentrations calculated for the individual points of the calibration curve, which differed by less than 9% (range: 91.1% to 108.6%) from the expected ones over the whole range. These back-fitting data easily met the requirement defined by the EMA guideline for bioanalytical method validation to identify suitable calibration curves of ligand-binding assays. The relative total error (RTE) of the calibration curve was low. In particular, RTE was calculated by back-fitting the mean blank-corrected optical densities (ODs) of the calibration curve standards. The concentrations obtained were normalized by multiplication with their dilution. The RTE was now calculated as the sum of the absolute difference between the nominal concentration of the assay standard and the mean concentration determined by the back-fitting approach and the double standard deviation of this mean concentration. Furthermore, the low RSD of the slope demonstrated that these curves could be obtained at a reproducibility required for an assay to be used in a clinical setting.

Figure 13:
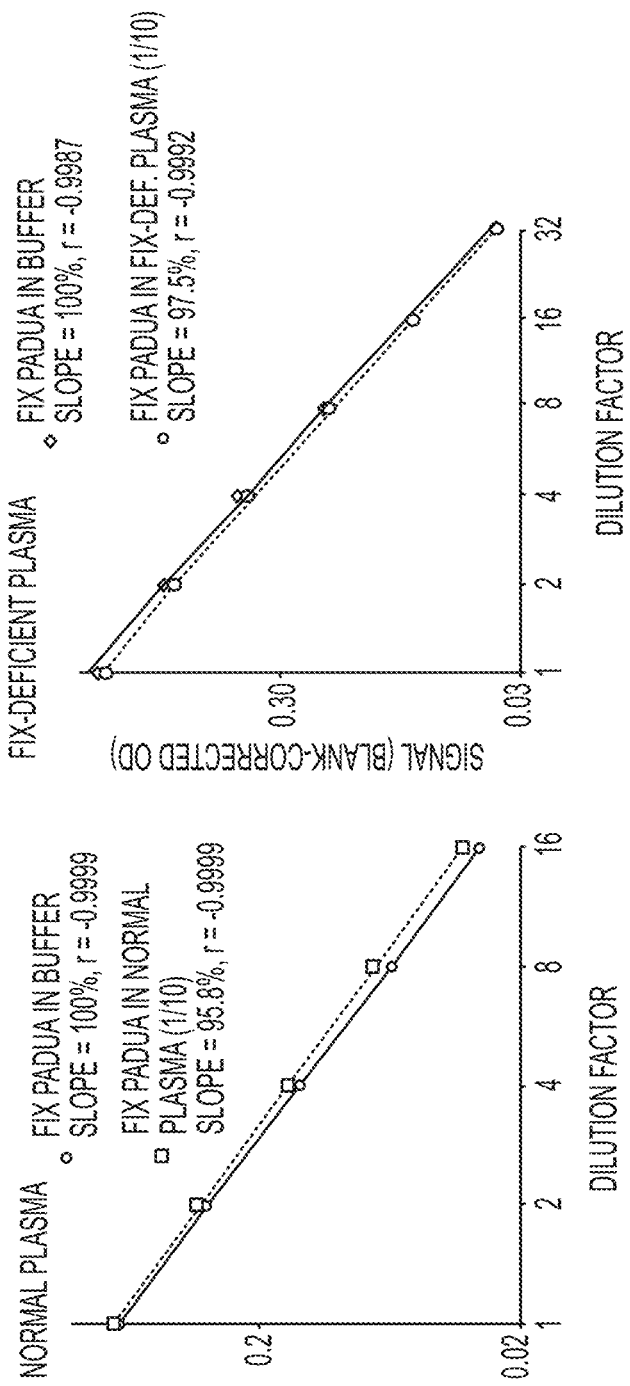
FIG. 13 represents a graph of dilution-response curves of the FIX Padua ELISA using FIX Padua in buffer or in normal plasma or FIX-deficient plasma.

The ELISA was carried out as described above. Normal fresh-frozen human plasma and FIX-deficient plasma were spiked with FIX Padua. The dilution series of the two spiked plasma preparations started at the dilution of 1/10. FIG. 13 shows the dilution-response curves of the two plasma samples in comparison to those obtained in buffer. The slopes of the dilution-response curves obtained for the FIX Padua-spiked plasma samples differed by less than 5% from that obtained for the buffer dilution series. This indicated that the plasma matrix had no influence on the assay performance.

Figure 14:
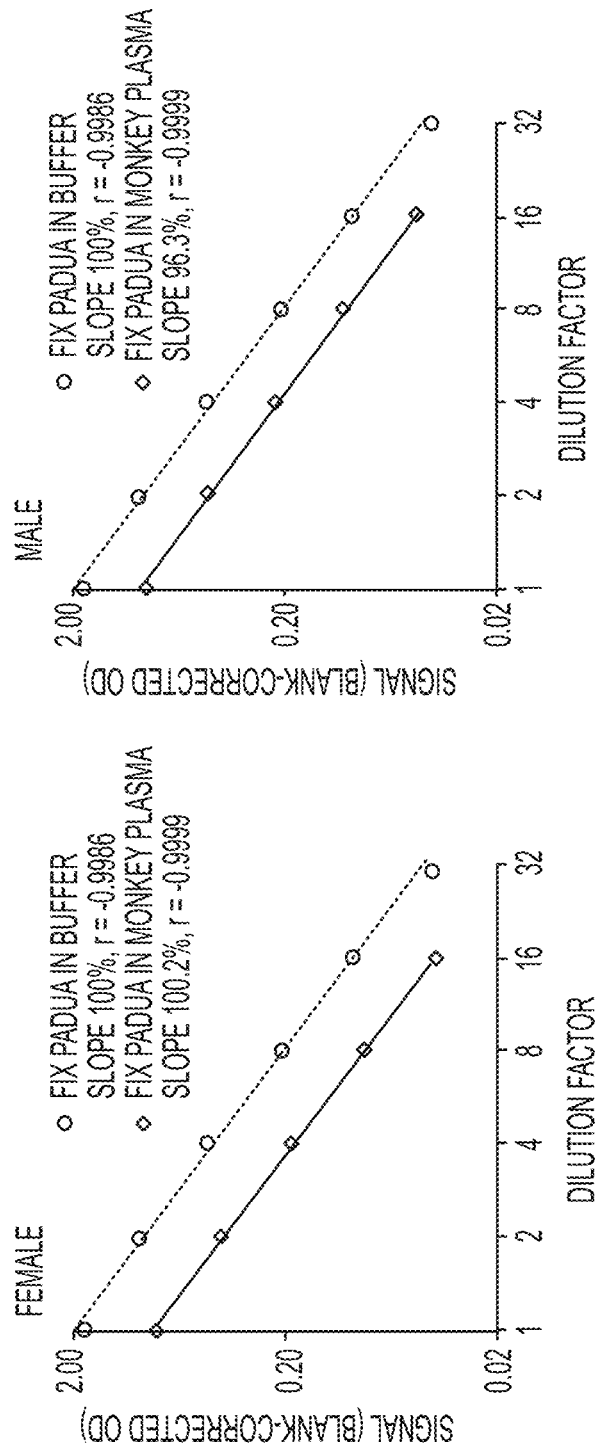
FIG. 14 represents a graph of dilution-response curves of the FIX Padua ELISA using citrated monkey plasma samples.

Conventional polyclonal anti-human FIX antibodies also bind to cynomolgus monkey FIX (data on file) due to the high sequence homology between human and monkey FIX. Therefore, the selectivity of the FIX Padua ELISA was checked also for the matrix of citrated monkey plasma. In particular, a female and male citrated monkey plasma sample was spiked with FIX Padua and measured starting the dilution series at the minimum dilution of 1/10. FIG. 14 shows the dilution-response curves of the two plasma samples in comparison to those obtained in buffer.

The slopes of the dilution-response curves obtained for the FIX Padua-spiked plasma samples differed by less than 4% from that obtained for the buffer dilution series. This indicated that the citrated monkey plasma matrix had no influence on the assay performance. Moreover, the recoveries of the spiked FIX Padua concentrations were 91.3% and 103.1% for the female and the male plasma sample, respectively.

Figure 15:
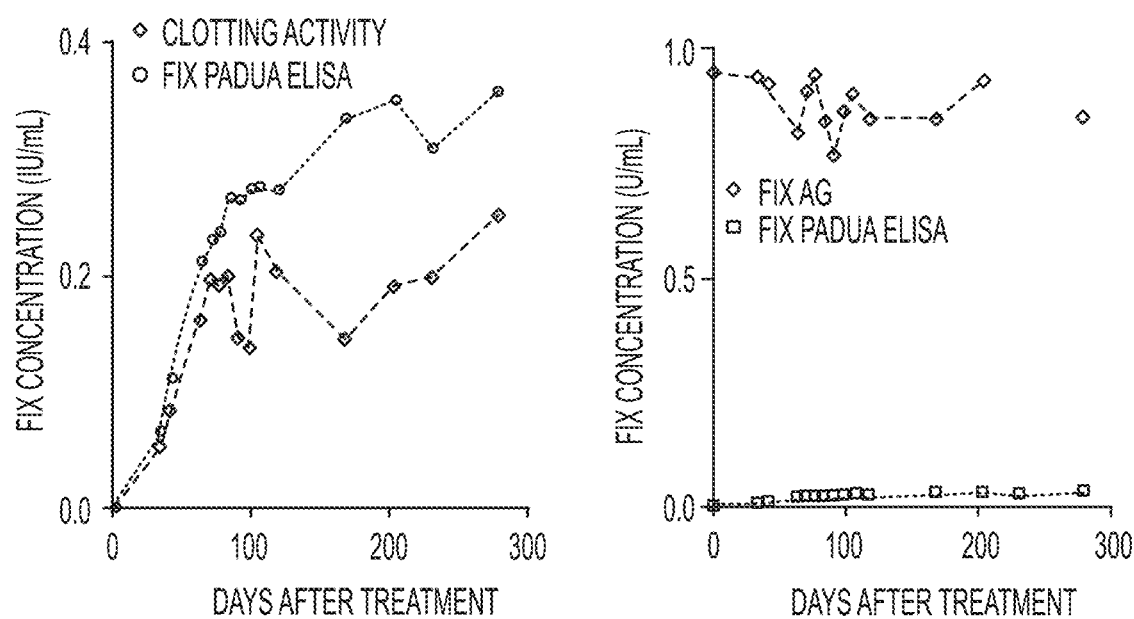
FIG. 15 represents a graph of the clotting activity and protein measurements of samples of a subject with FIX cross-reactive material (CRM+) after treatment with AAV2/8 viral vector expressing FIX Padua.

Measurements of FIX Padua in citrated plasma samples from a subject with FIX cross-reactive material (CRM+) in a Phase 1/2 clinical trial after treatment with AAV2/8 viral vector expressing FIX Padua were performed. Using the plasma samples from the subject, the FIX Padua ELISA was carried out as described above. The FIX coagulation activity and the FIX antigen measurements using the plasma samples obtained from the subject were performed by using standard methods. FIG. 15 shows the results of the FIX activity and FIX protein measurement carried out for the plasma samples obtained from a subject from a Phase1/2 clinical trial, which constantly demonstrated a FIX antigen concentration of close to 1 U/mL, but FIX activity below the lower limit of quantification. This data qualified the subject to demonstrate CRM+, i.e. coagulation-inactive FIX protein, measurable with a conventional FIX ELISA. The results of the FIX Padua ELISA, obtained in ng/mL, were transformed to activity and antigen units, using for the activity transformation the specific activity of the assay standard (2310 IU/mg) and for the antigen transformation a normal human FIX concentration of 5 µg/mL.

The FIX Padua ELISA data paralleled the FIX activity data, evidencing that the FIX activity measured was dependent on the expression of FIX Padua. In contrast, the FIX antigen concentrations measured with the FIX Padua-specific ELISA were clearly lower than those obtained with the standard ELISA, demonstrating that the FIX Padua ELISA allowed discrimination between CRM+ material and FIX Padua.

Figure 16:
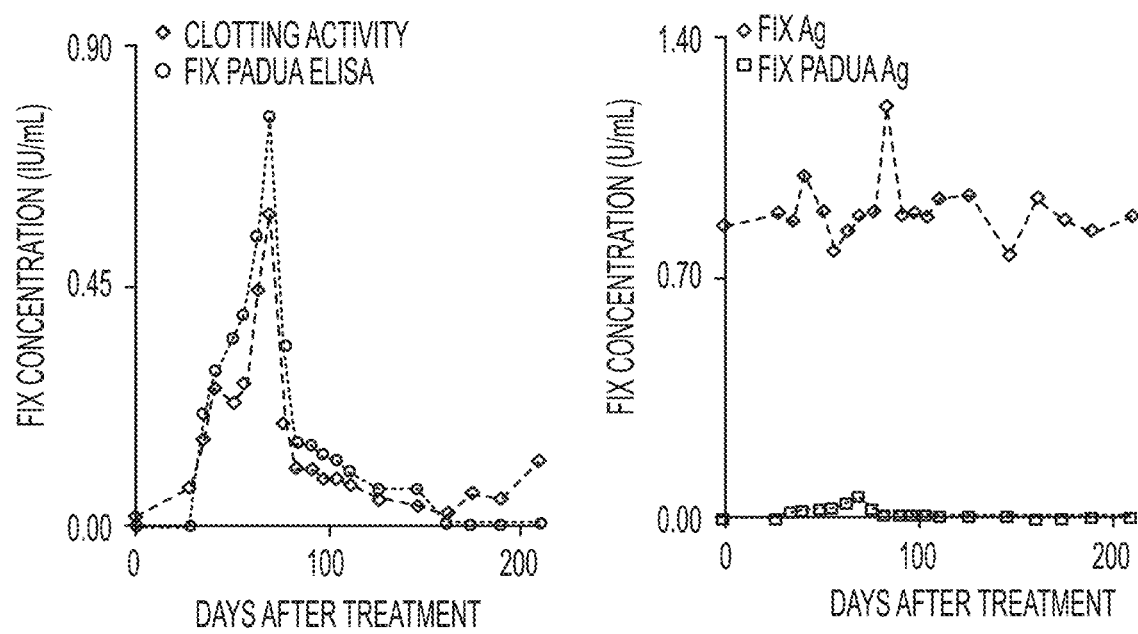
FIG. 16 represents a graph of the clotting activity and protein measurements of samples of a second subject with FIX cross-reactive material (CRM+) after treatment with AAV2/8 viral vector expressing FIX Padua.

Measurements of FIX Padua in citrated plasma samples from a second subject with FIX cross-reactive material (CRM+) in a Phase 1/2 clinical trial after treatment with AAV2/8 viral vector expressing FIX Padua were performed. Using the plasma samples from the second subject, the FIX Padua ELISA was carried out as described above. The FIX coagulation activity and the FIX antigen measurements using the plasma samples obtained from the second subject were performed by using standard methods. FIG. 16 shows the results of the FIX activity and FIX protein measurement carried out for the plasma samples obtained from the second subject, which constantly demonstrated a FIX antigen concentration of close to 0.8 U/mL, but FIX activity below the lower limit of quantification. This data qualified the subject to demonstrate CRM+, i.e., coagulation-inactive FIX protein, measurable with a conventional FIX ELISA. The results of the FIX Padua ELISA, obtained in ng/mL, were transformed to activity and antigen units, using for the activity transformation the specific activity of the assay standard (2310 IU/mg) and for the antigen transformation a normal human FIX concentration of 5 µg/mL.

The FIX Padua ELISA data paralleled the FIX activity data, evidencing that the FIX activity measured was dependent on the expression of FIX Padua. In contrast, the FIX antigen concentrations measured with the FIX Padua-specific ELISA were clearly lower than those obtained with the standard ELISA, demonstrating that the FIX Padua ELISA allowed discrimination between CRM+ material and FIX Padua.

Figure 17:
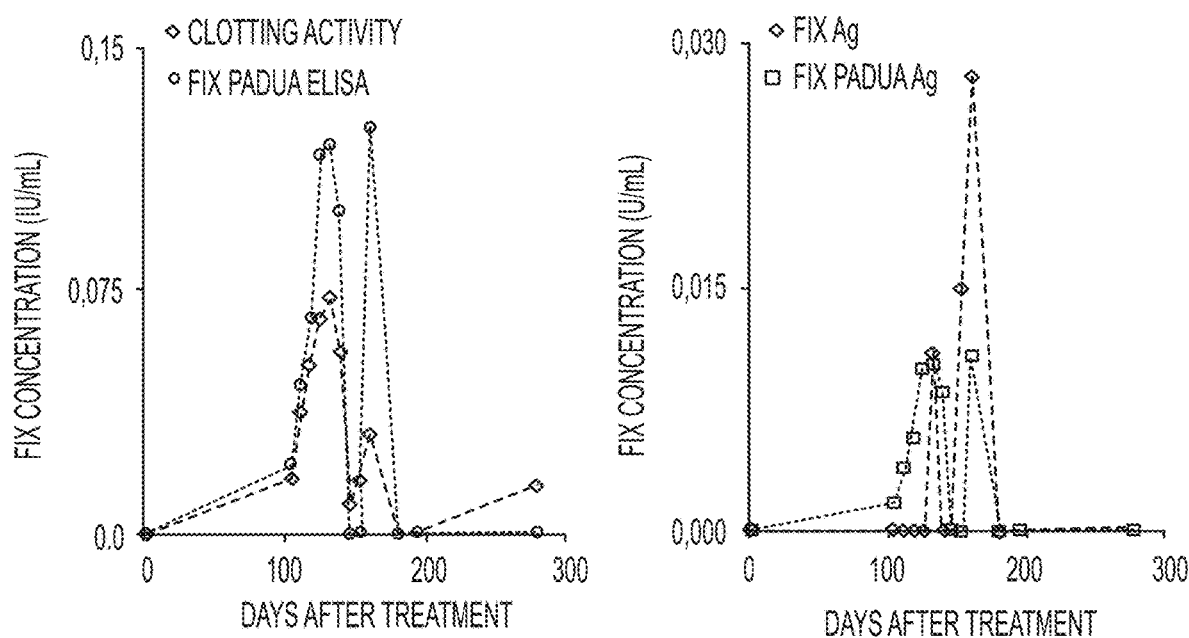
FIG. 17 represents a graph of the clotting activity and protein measurements of samples of a subject without FIX cross-reactive material (CRM+) after treatment with AAV2/8 viral vector expressing FIX Padua.

Measurements of FIX Padua in citrated plasma samples from a subject without FIX CRM+ in a Phase 1/2 clinical trial after treatment with AAV2/8 viral vector expressing FIX Padua were performed. Using the plasma samples from the subject without FIX CRM+, the FIX Padua ELISA was carried out as described above. The FIX coagulation activity and the FIX antigen measurements using the plasma samples from the subject without FIX CRM+ were performed by using standard methods. FIG. 17 shows the results of the FIX activity and FIX protein measurement carried out for the plasma samples obtained from the subject which constantly demonstrated no CRM+. The results of the FIX Padua ELISA, obtained in ng/mL, were transformed to activity and antigen units, using for the activity transformation the specific activity of the assay standard (2310 IU/mg) and for the antigen transformation a normal human FIX concentration of 5 µg/mL. The FIX Padua ELISA data paralleled the FIX activity and FIX protein data, evidencing that the FIX activity measured was dependent on the expression of FIX Padua.

Example 4

Figure 18:
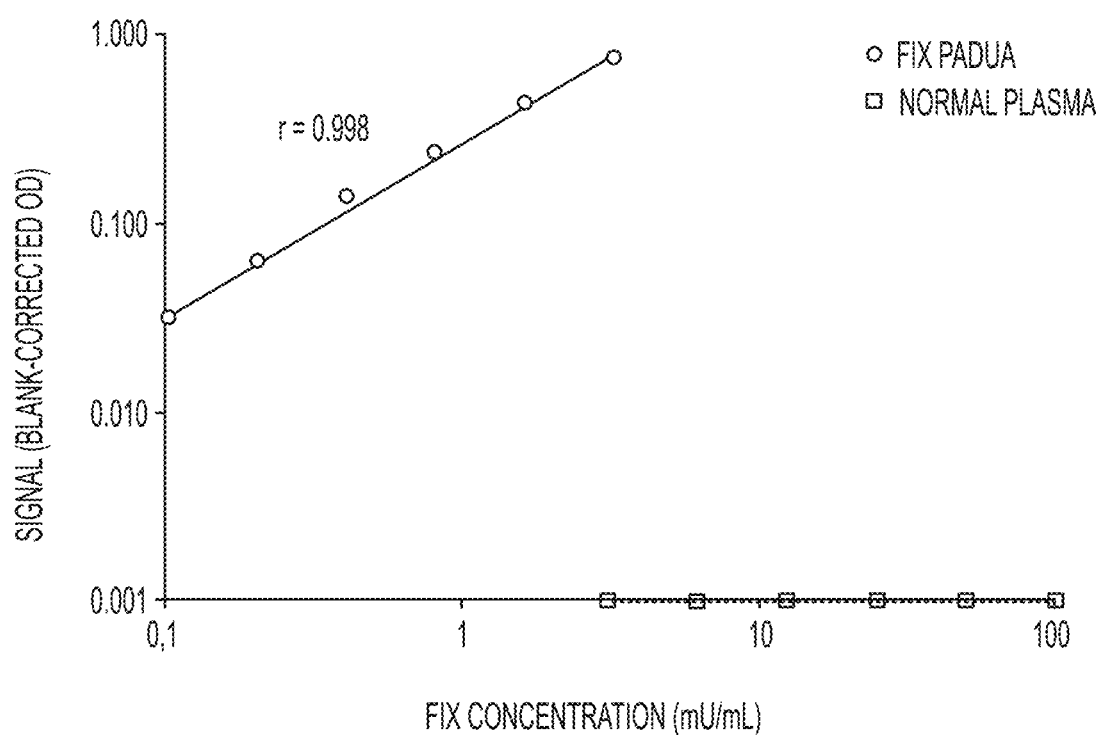
FIG. 18 represents a graph of the signal as a function of FIX concentration, where the signal is generated by a FIX Padua-specific chromogenic activity assay.

A FIX chromogenic activity assay was also developed using BC1. FIX Padua was selectively purified from the sample matrix by binding to the plate-bound BC1. Non-bound sample components, including human FIX wild type were removed by extensive washing, before the chromogenic Factor IX Test 221806 (Hyphen Biomed) was carried out on the wells of the microplate. The samples were diluted with the dilution buffer described above. FIG. 18 shows the dose response-curve obtained for FIX Padua and a normal reference plasma preparation.

FIX Padua showed a linear concentration-response curve, while the normal reference plasma concentration with a FIX concentration of about 1 U/mL did not demonstrate any measurable signal. These data demonstrated the feasibility of the approach, describing a FIX Padua-specific activity assay and at the same time confirmed its specificity.

Example 5

The following describes an isolation of antibodies that differentiate between FIX wild type and the FIX Padua variant.

FIX Padua is a naturally occurring hyper-functional variant of wild-type FIX with a single amino acid exchange (FIX R338L). The usefulness of FIX Padua for hemophilia B gene therapy has been shown in preclinical models and is currently being explored in clinical phase 1/2 programs. Assessment of the success of the therapy largely relies on the determination of the expression of the FIX Padua transgene, which is however hampered by the lack of an antibody that discriminates between wild-type FIX and FIX Padua. Antibodies that specifically recognize FIX Padua without cross reactivity to wild-type FIX allows the development of assays that unambiguously detect FIX Padua in clinical samples. A phage display method was used to select specific FIX Padua binders. The phage library was screened with a linear and a structural peptide that enclosed the single amino acid substitution at position 338, as well as full-length recombinant FIX Padua. Three rounds of panning, with and without competition with wild-type FIX sequences, led to the identification of several binders. BIACORE (surface plasmon resonance) and ELISA experiments were performed to determine the specificity and affinity of the antibodies obtained. Various antibodies were initially identified from the different phage display panning routes. An antibody generated from the linear peptide route demonstrated unique and specific FIX Padua binding. The selected antibody had a detection limit of ~3 ng/mL plasma and showed no cross reactivity to wild-type FIX even at highly elevated (>50 µg/mL) concentrations. The highly specific anti-FIX Padua antibody can be used for the development of clinical assays to selectively distinguish between wild-type FIX and FIX Padua antigen levels.

INTRODUCTION

FIX Padua is a naturally occurring hyper-functional variant of FIX wild-type (wt) with a single amino acid exchange (FIX R338L). This gain in function mutation leads to an 8- to 10-fold increase in specific clotting activity compared with normal FIX. In vitro, recombinant FIX-R338L had a 5- to 10-fold higher specific clotting activity than that of the recombinant FIX wild type [1]. The usefulness of FIX Padua for hemophilia B gene therapy has been shown in preclinical models, and is currently being explored in a clinical Phase 1/2 trial. Assessment of the success of the therapy largely relies on determination of the FIX Padua transgene expression, which is however hampered by the lack of an antibody that discriminates between FIX wt and FIX Padua.

The objective of this study was to generate antibodies that specifically bind FIX Padua without cross reactivity to FIX wild-type to allow detection of FIX Padua in the presence of FIX wt in clinical samples.

The following describes the methods carried out during this study.

Figure 19:
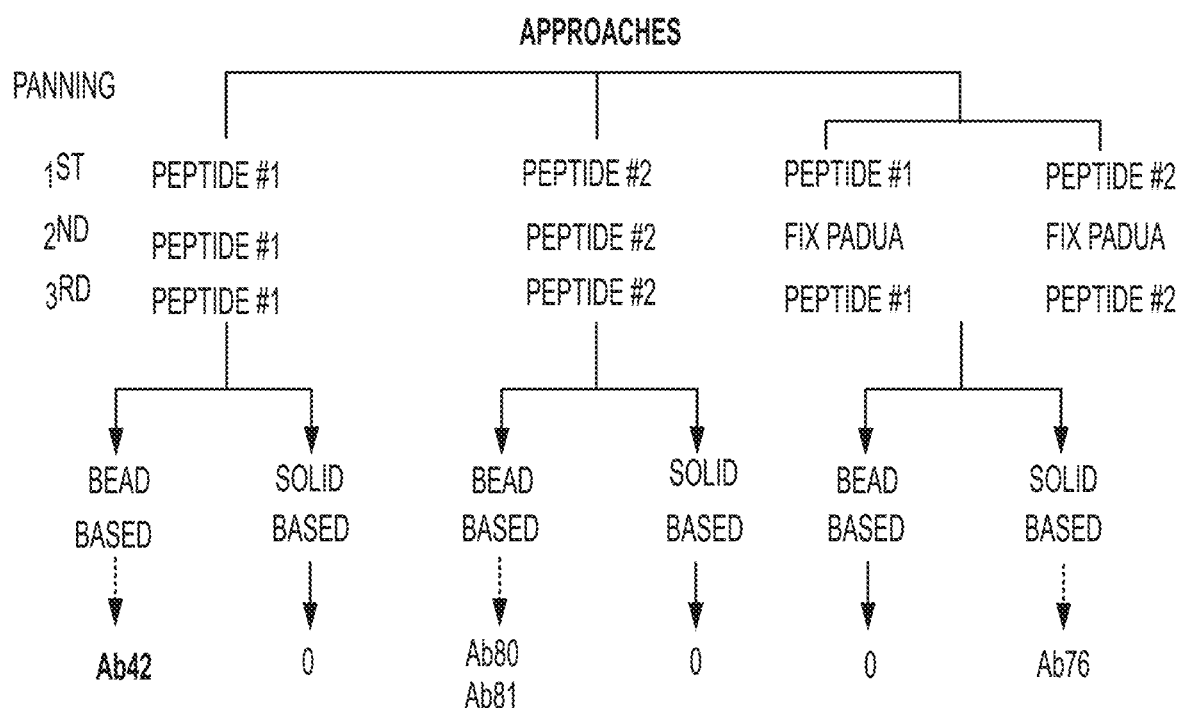
FIG. 19 represents a schematic of strategies for the generation of FIX Padua specific Fabs and sequences of used panning and blocking peptides (L338 in FIX Padua is indicated in red and boxed, R338 in FIX wt is indicated in green and boxed)
Figure 20:
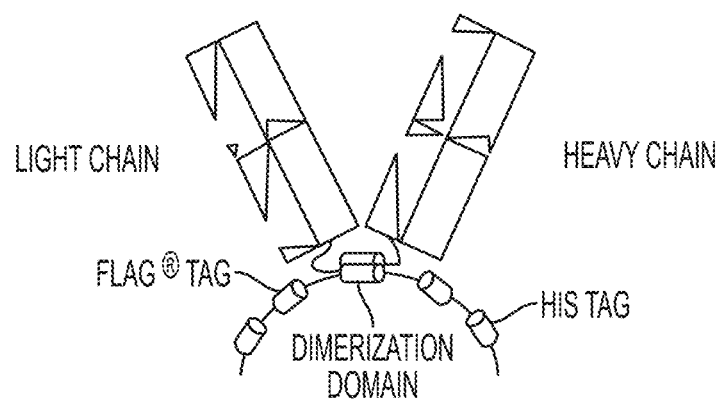
FIG. 20 represents a schematic structure of purified mini antibodies (bivalent Fabs).

Generation of anti Padua FIX specific antibodies: Antibodies (bivalent Fabs) were generated by Phage Display Technology based on HuCAL PLATINUM® library and CysDisplay® technology. Four different approaches were applied to isolate antibodies specifically for FIX Padua (FIG. 19). Two were performed with peptides that enclosed the single amino acid substitution at position 338 either in a solid or liquid (bead) phase assay. The third and fourth strategy included the full-length active FIX Padua protein. Three panning rounds were performed for each strategy, including the proper negative controls (wt peptides or FIX wt). Fabs of unique positive clones were produced and tested for specific binding to FIX Padua antigens. For ELISA, antigens [5 µg/mL] were coated and incubated with Fab fragments [2 µg/mL] followed by detection with an anti Fab AP conjugate.

Plasmatic ELISA: Fabs were coated on MaxiSorp ELISA plates [5 µg/mL] and incubated with 20% human plasma diluted in PBS buffer plus 50 mM benzamidine. Plasma was spiked with 5 µg/mL rFIX wt and increasing concentrations of rFIX Padua (in-house produced in HEK293). Detection was done using a HRP labeled polyclonal goat anti FIX antibody (100 ng/mL).

BiaCore: All experiments were performed at 25° C. using a Biacore™ 200 instrument and nickel-coated biosensor chips (NTA-Chip GE Healthcare). The instrument was first primed three times with HBS-EP running buffer, and flow cell 1 (FC1) was used as the reference flow cell, which was unmodified and lacked the Fab ligand. Flow cell 2 (FC2) was used for immobilization of ~500 RU FIX Padua specific Ab42. Ligand concentrations ranged from 100 to 6.25 nM.

The results of this study are described below.

Figure 21:
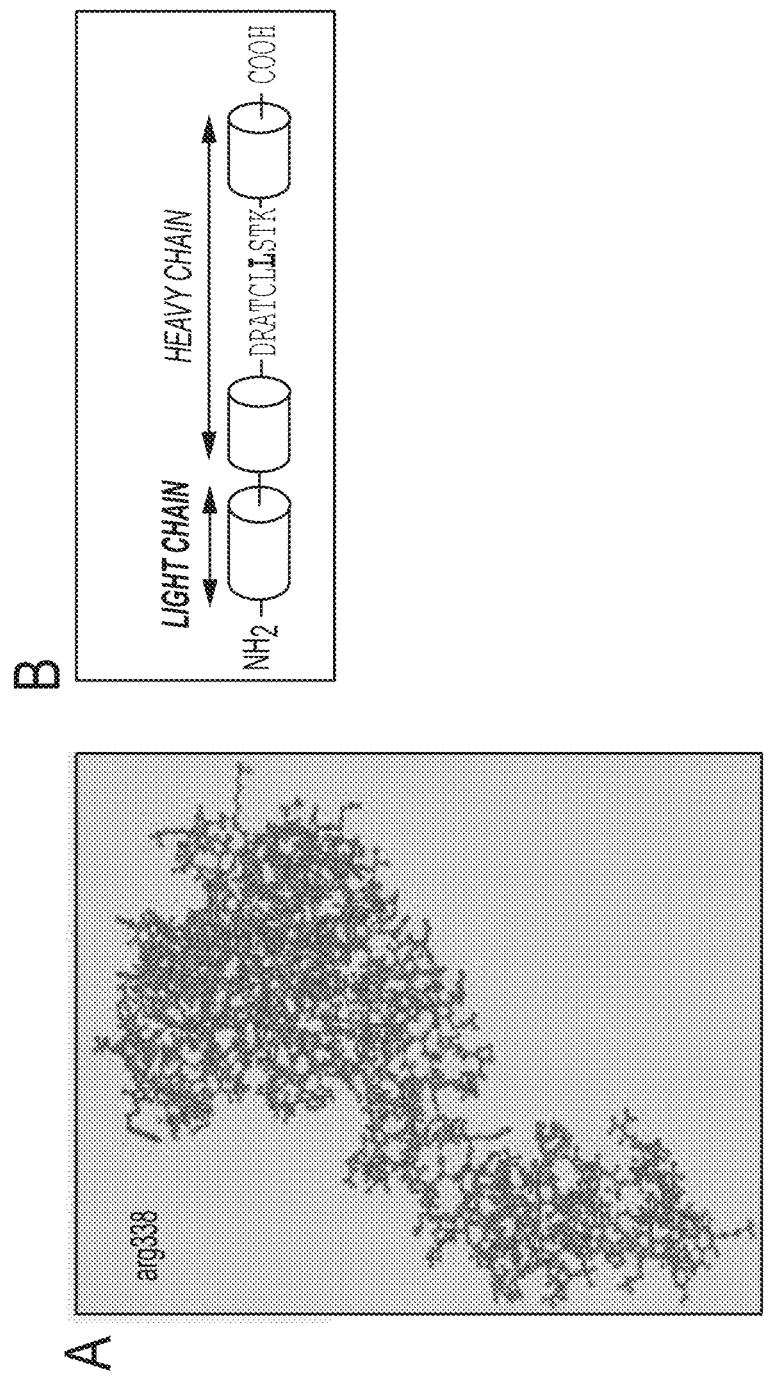
FIG. 21 represents (FIG. 21A) an X-ray structure of porcine FIXa and demonstrates that Arg338 is located on the surface of heavy chain of porcine FIXa and (FIG. 21B) a scheme of human FIX Padua and demonstrates Leu338.
Figure 22:
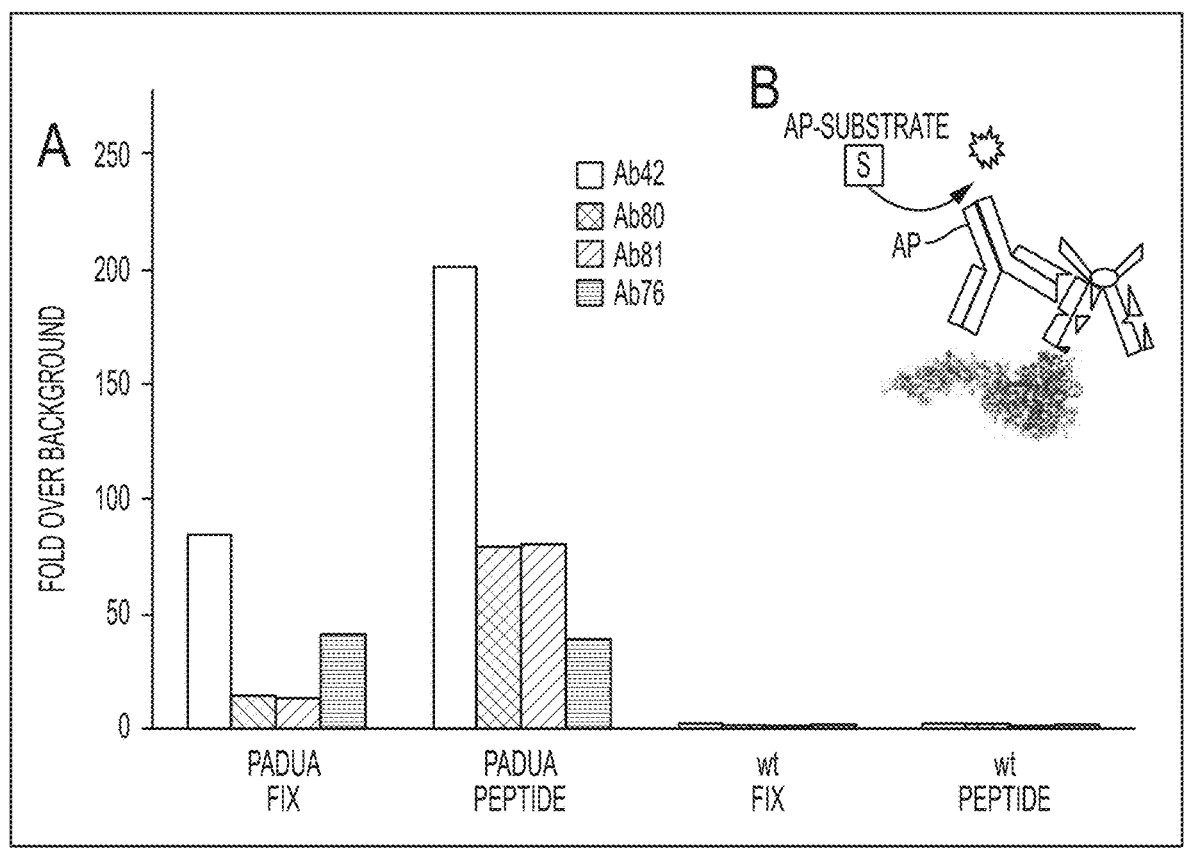
FIG. 22 represents a graph demonstrating that purified Fabs bind specifically to FIX Padua and not to FIX wt antigens.
Figure 23:
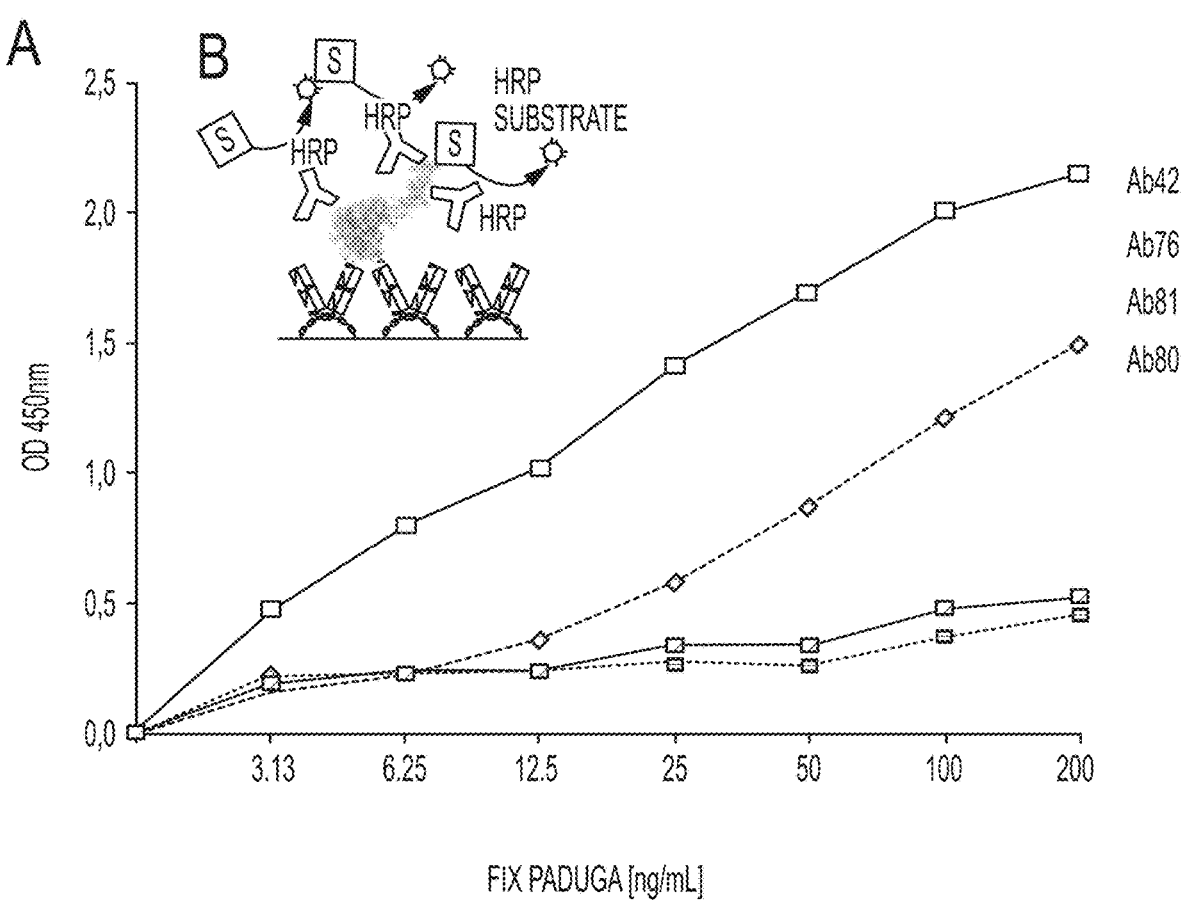
FIG. 23 represents a graph demonstrating that purified bivalent Fabs show no cross reactivity to FIX wt in 20% human plasma matrix.
Figure 24:
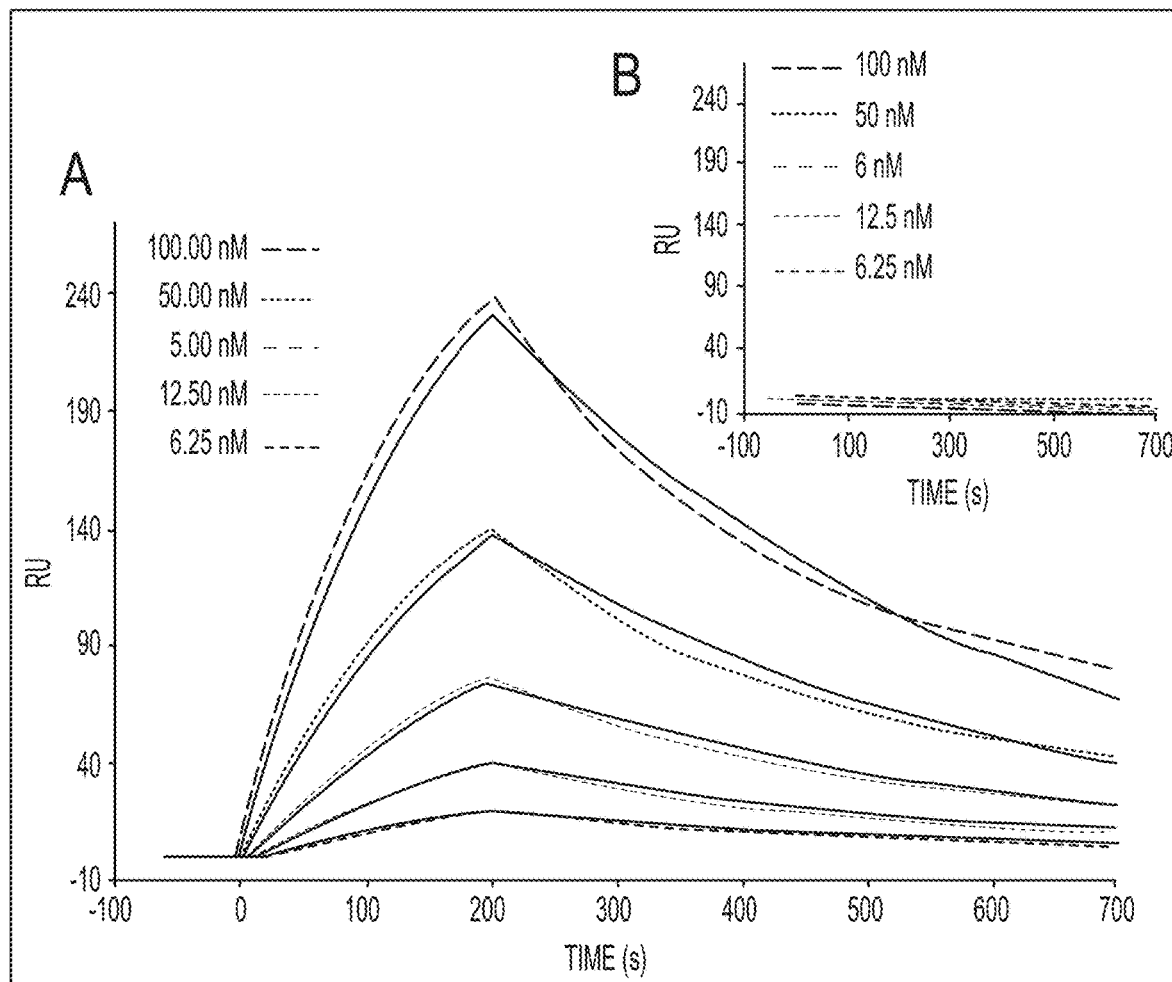
FIG. 24 represents a graph demonstrating surface plasmon resonance (SPR) analysis of selected candidate Ab42.

Structural analysis of porcine wt FIX revealed that the single Padua modification (R338L) is located on the surface of the protein [2] (FIG. 21), and is therefore a suitable epitope for the generation of highly specific antibodies. Purified bivalent Fabs were tested for antigen specificity (FIG. 22) and cross reactivity to FIX wt in 20% human plasma by ELISA (FIG. 23). In 20% plasma matrix containing 5 µg/mL spiked FIX wt, only two (Ab42 and Ab76) of four isolated bivalent Fabs bound specifically to FIX Padua. Only Ab42 did not show any cross reactivity against human FII and human FX (data not shown).

Based on these data, it was concluded that a highly specific anti FIX Padua mini antibody Ab42 was generated using Phage Display technology. The selected candidate shows no cross reactivity to FIX wild type or other common blood factor proteins such as FII or FX. Effective binding to FIX Padua was shown in a human plasma matrix (20%) and in the presence of common concentration of FIX wt. Mini antibody Ab42 is currently used for FIX Padua analysis in plasma from patients treated during a clinical Phase 1/2 trial (see below).

In the study described above, the following references are cited: (1) Simioni et al., X-Linked Thrombophilia with a Mutant Factor IX (Factor IX Padua) N Engl J Med 2009; 361: 1671-5; and (2) Brandstetter et al., X-ray structure of dotting factor IXa: active site and module structure related to Xase activity and hemophilia B. Proc Nail Acad Sci USA. 1995 Oct. 10; 92(21): 9796-800

The following describes a development and application of a FIX Padua-specific immunoassay for the monitoring of hemophilia B gene therapy.

Gene therapy holds great promise as a future treatment option for Hemophilia. In one clinical Phase 1/2 trial, an AAV2/8 viral vector is used to express FIX Padua (FIXp), a hyper-functional variant of FIX with a single amino acid exchange (R338L), in subjects with severe hemophilia B. Specific detection of the transgene product is key for assessing the success of the therapy, but challenging for patients with FIX cross-reactive material (CRM+). Development of a FIXp-specific ELISA and application of this assay for the measurement of FIXp expressed in the plasma of hemophilia B patients after treatment with AAV2/8 viral vector expressing FIX Padua. The Fab fragment of a newly developed FIXp-specific binding antibody was coated to 96-well microplates at 2 µg/mL using standard conditions. A biotinylated polyclonal sheep anti-human FIX IgG and streptavidin peroxidase were used as detection system. Assay calibration was obtained by generating a six-point calibration curve with a FIXp preparation, covering a FIXp concentration range from 27.1-0.85 ng/mL. Patients' samples were diluted with HEPES/NaCl buffer containing 5 mg/mL bovine serum albumin, 10 mM benzamidine, 10 mM $CaCl_2$) and 0.05% Tween 20. Normal human plasma or purified human FIX showed no signals in the FIXp-specific ELISA. Accurate calibration curves were obtained. FIXp spiked to 1/10-diluted normal human plasma showed acceptable recoveries with dilution response curves parallel to that obtained for the assay standard in buffer. Importantly, the analysis of samples of six patients treated with AAV encoding FIXp demonstrated highly similar FIXp protein and FIX activity curves over time, and the samples of CRM+ patients showed no increased signals for FIXp protein compared to CRM− patients, indicating the specificity of the assay. The FIXp-specific ELISA allows additional monitoring of treatment outcome by the measurement of the FIXp protein. This represents the first data demonstrating the feasibility of this approach.

INTRODUCTION

Gene therapy holds great promise as a future treatment option for hemophilia [1]. In a clinical Phase 1/2 trial, an AAV2/8 viral vector is used to express FIX Padua (FIXp) [2], a hyper-functional variant of FIX with a single amino acid exchange (R338L), in subjects with severe hemophilia B. Specific detection of the transgene product is crucial for assessing the success of the therapy, but challenging for patients with FIX cross-reactive material (CRM+).

Figure 25:
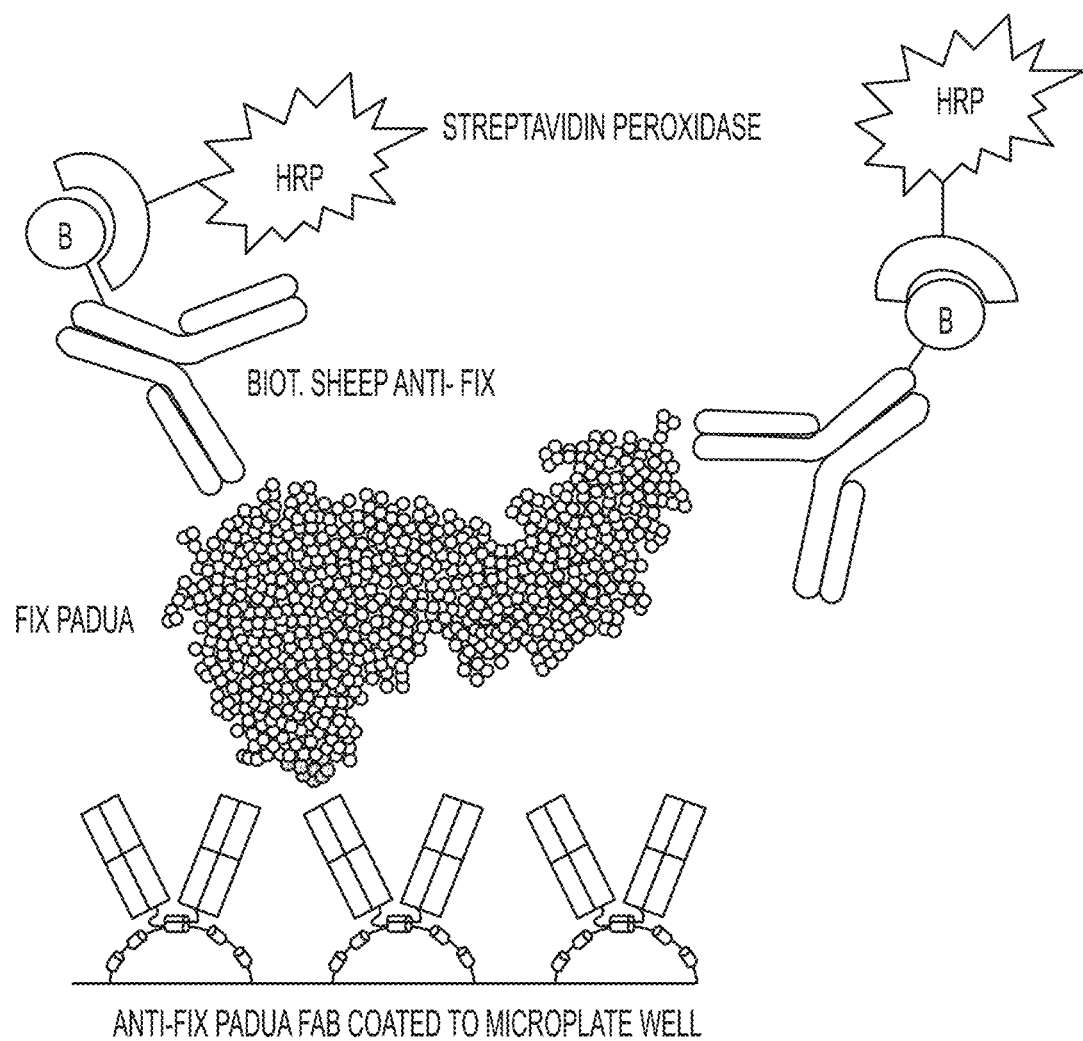
FIG. 25 represents an illustration of the immunoassay.
Figure 26:
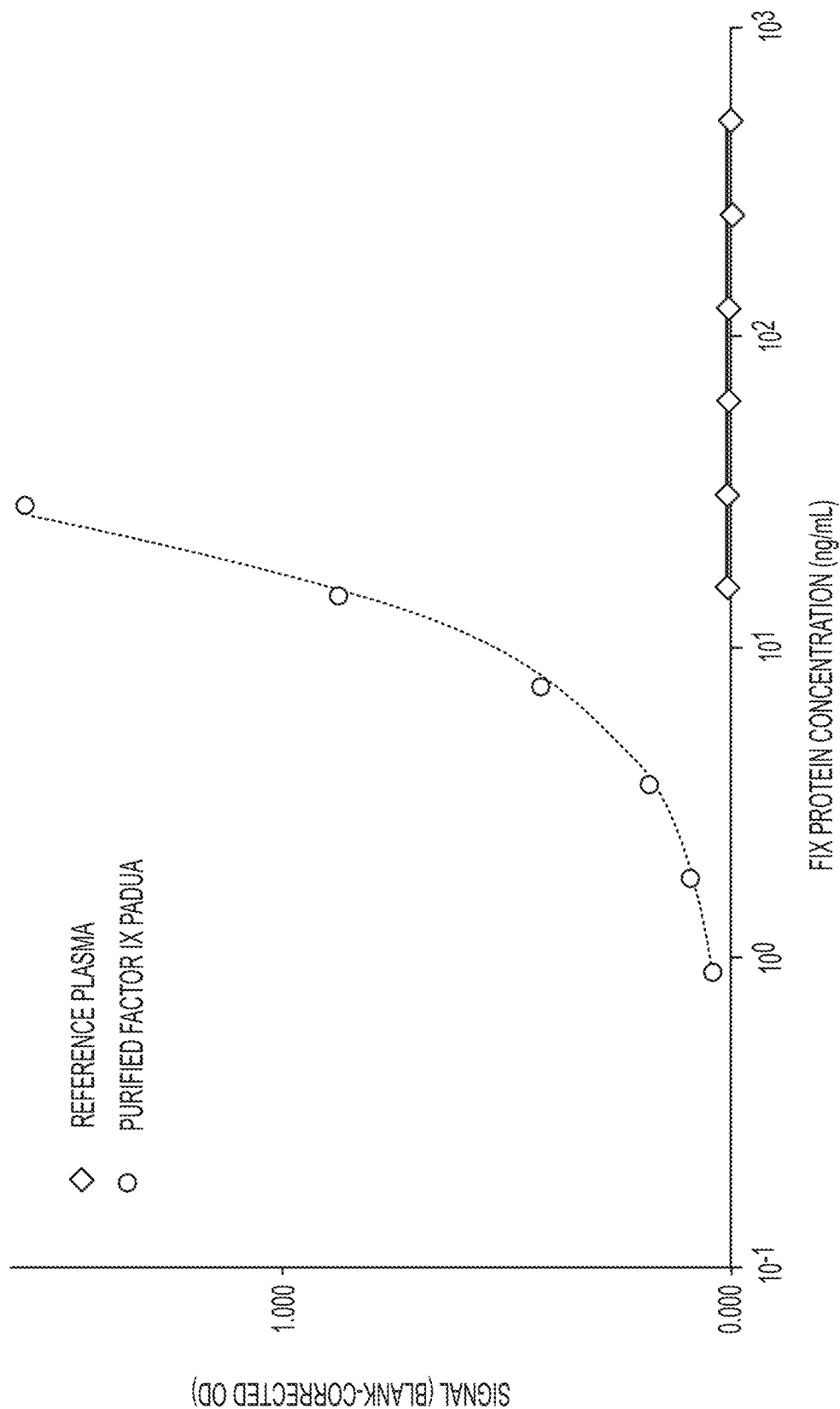
FIG. 26 represents a graph demonstrating assay selectivity as represented by concentration-response curves obtained for a purified FIXp sample and a fresh-frozen reference plasma preparation with a normal FIX concentration of 5 μg/mL demonstrate the selectivity of the assay. Human plasma showed essentially no response.
Figure 27:
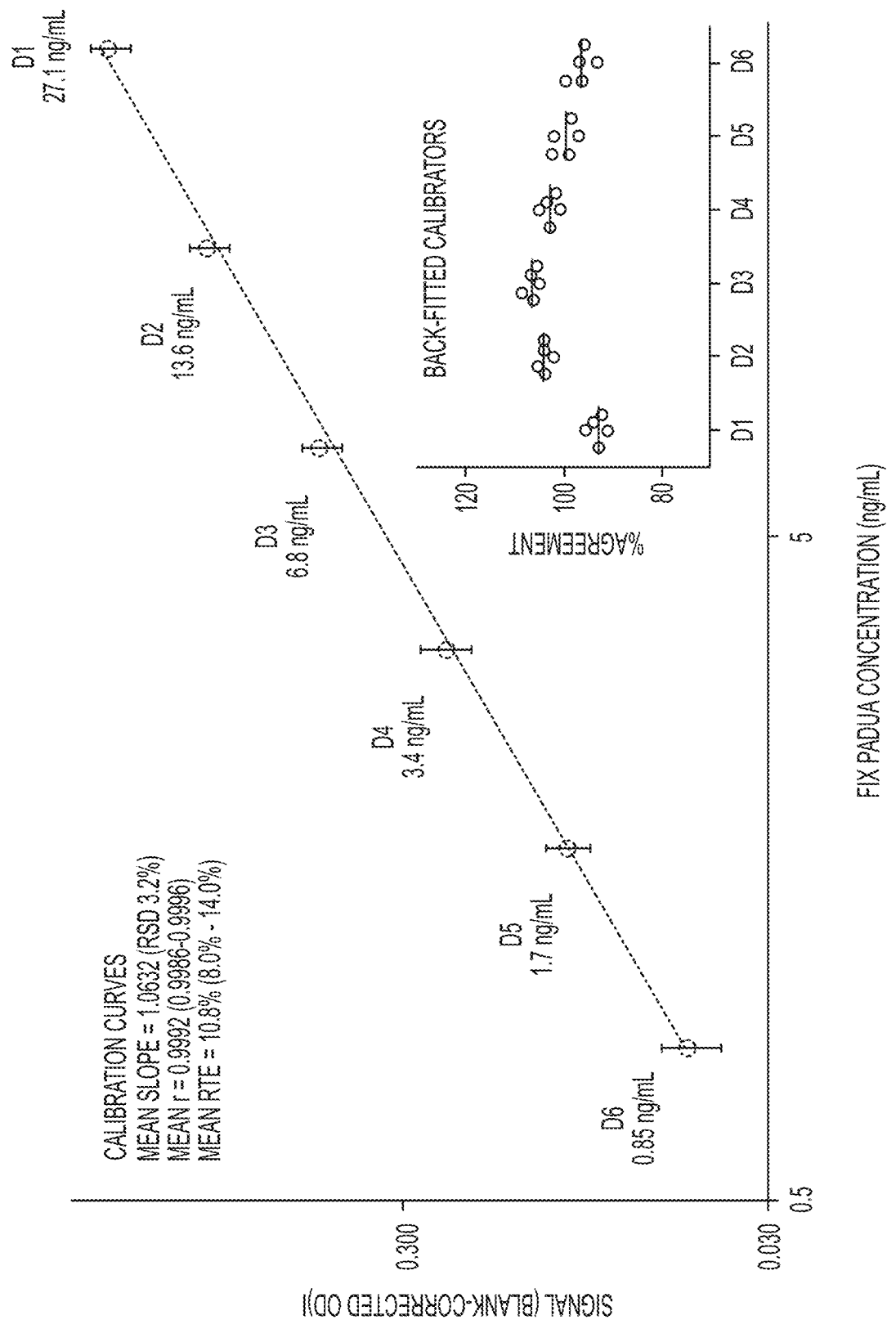
FIG. 27 represents a graph of the 6-point calibration curves, ranging from 0.85 to 27.1 ng FIXp/mL, had adequate linearity. Their accuracy was demonstrated by the correlation coefficients r, the low relative total errors (RTEs), and the results of the back-fitting approach.
Figure 28:
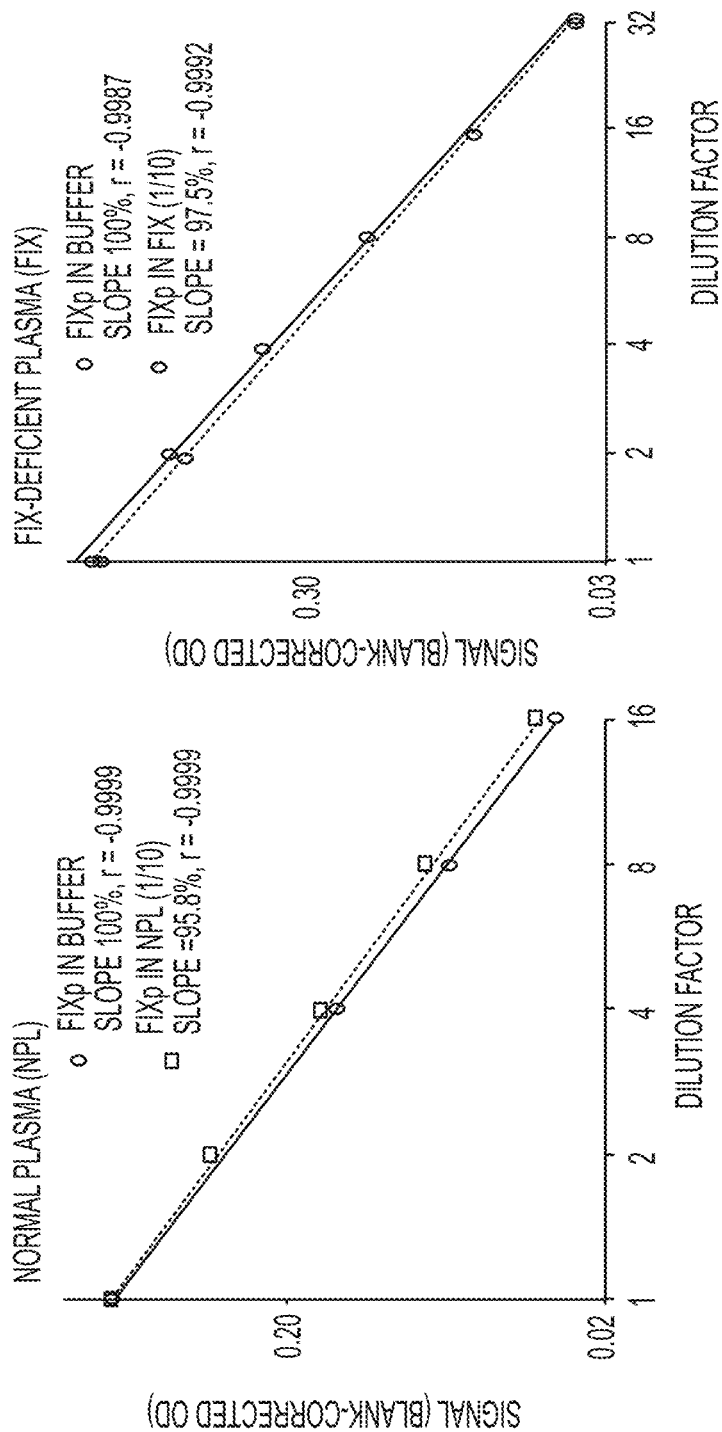
FIG. 28 represents a set of graphs demonstrating the parallelism study in normal and FIX-deficient plasma. The slopes of the dilution-response curves of the FIXp-spiked plasma differed by <5% from that obtained for the buffer dilution series, indicating that the plasma matrix had no influence on the assay performance.
Figure 29:
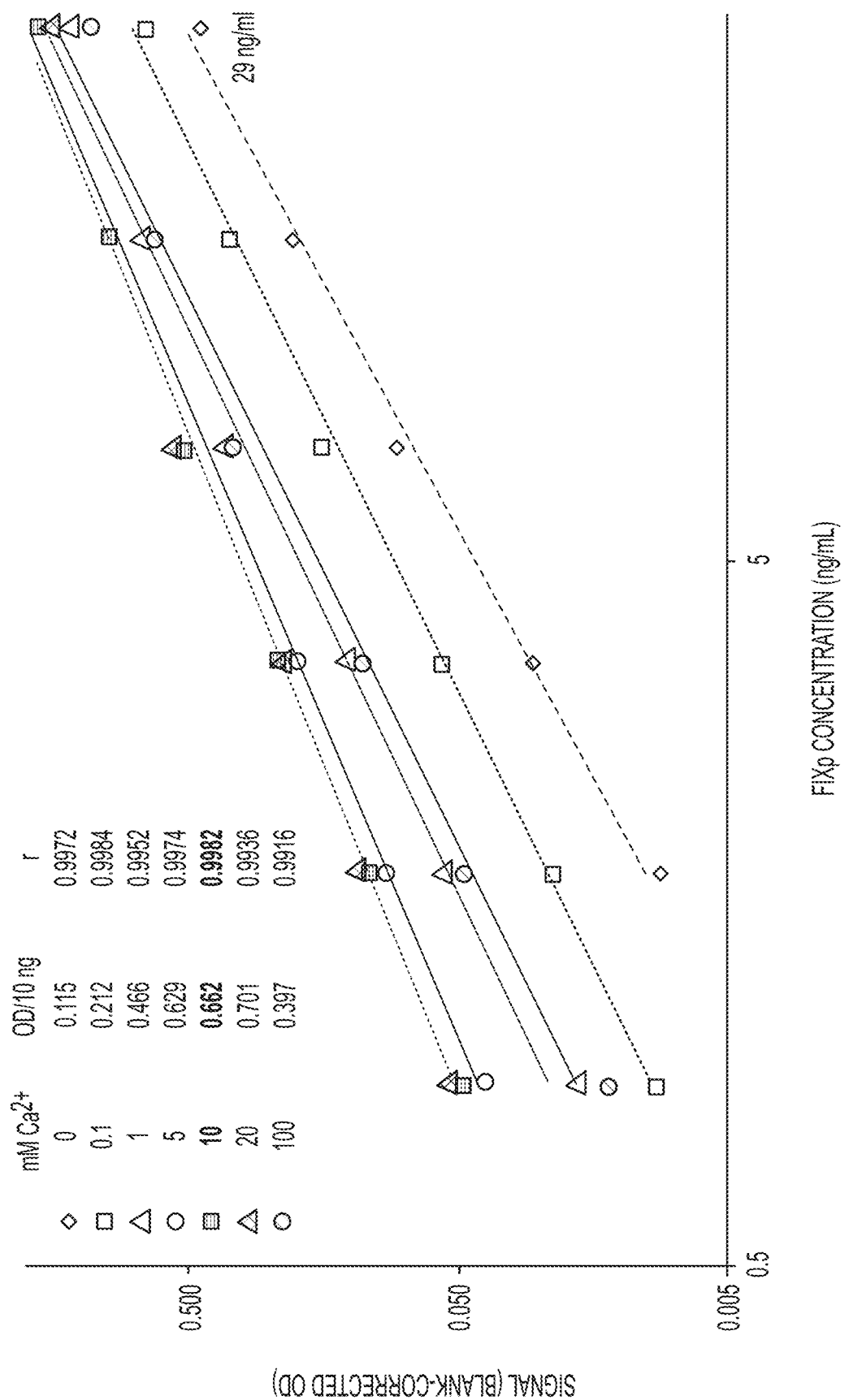
FIG. 29 represents a graph demonstrating the influence of $Ca^{2+}$ on the sensitivity of the ELISA. A clear increase in sensitivity triggered by $Ca^{2+}$ is shown, very likely caused by the polyclonal detection antibody and the Ca-dependent EGF domain of FIX.

FIG. 25 depicts the principle of the method (assay) described in this study. Anti-FIX Padua Fab is coated to microplate wells and selectively captures FIX Padua from the sample. After a washing step, removing non-bound sample compounds, the bound FIX Padua is detected using an in-house biotinylated polyclonal sheep anti-FIX IgG and streptavidin peroxidase. The bound HRP activity is measured using the ready-to-use HRP substrate SureBlue.

The following describes the methods carried out during this study.

ELISA procedure: The Fab preparation Ab42 (0.94 mg/mL) was diluted 1/500 with 0.1 M $NaHCO_3$—$Na_2CO_3$, pH 9.5 and bound to the wells of Maxisorp F96 plate by incubating 100 µL/well at 0 to +10° C. overnight. The dilution buffer (DB), used for dilution of the samples and reagents and for blocking of the plates, contained 0.1 M HEPES, 0.1 M NaCl, pH 7.2, 5 mg/mL biotin-free bovine serum albumin (BSA), 10 mM $Ca^{2+}$, 0.05% Tween 20 (Bio-Rad, EIA grade), and 10 mM benzamidine. After coating, the plate was washed with phosphate-buffered saline containing 0.05% Tween 20. The wells were then blocked by incubation with 200 µL DB/well at room temperature (RT) for 60 min. The blocking step was terminated by washing. Then, the dilutions of the standard/samples were loaded, preparing the serial 1+1 dilution series directly on the plate. The dilutions (100 µL/well) were incubated at RT for 60 min. The plate was washed again, and the biotinylated polyclonal sheep anti-human FIX detection antibody prepared from F9-1030A (A-Coa) added (100 µL/well; dilution 11500). After incubation at RT for 60 min, the plate was washed again, and streptavidin peroxidase (DakoCytomation) added (100 µL/well: dilution 1/4,000) and incubated at RT for 30 min. After a final washing procedure, the bound peroxidase activity was measured with the ready-to-use peroxidase substrate SureBlue (KPL), stopping the reaction with 3 N sulfuric acid. The plate was then measured at 450 nm, subtracting the results obtained at 620 nm. The calibration curve was constructed with a purified recombinant FIX Padua (FIXp) preparation, demonstrating a protein concentration of 542.4 µg/mL. The specific clotting activity of 2,310 IU/mg protein clearly classified this preparation as the hyperactive FIX Padua variant. The serial dilution series ranged from 1/20,000 to 1/640,000 and defined a FIX concentration range from 27.1 to 0.85 ng/m L.

Figure 32:
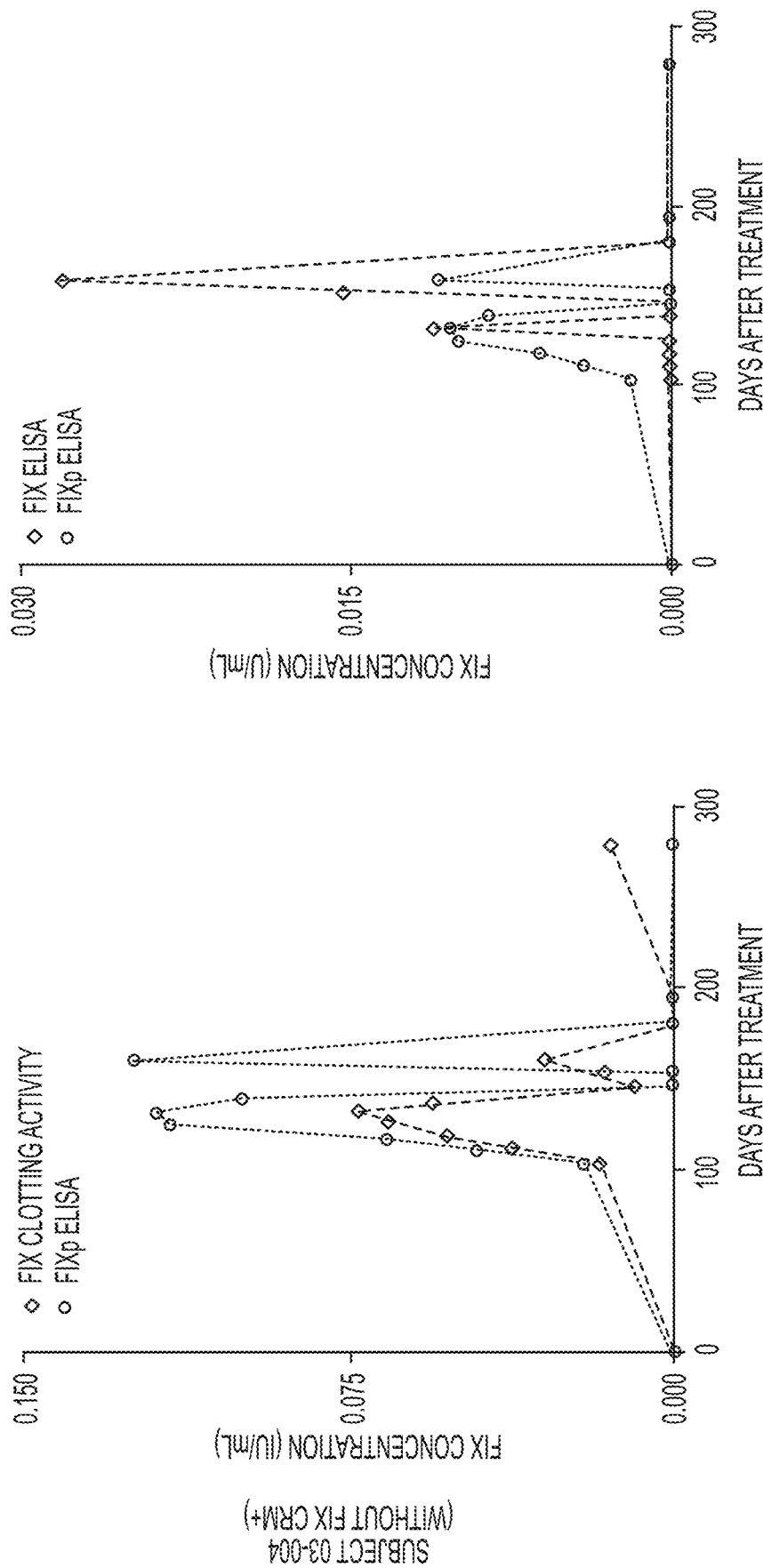
FIG. 32 represents a set of graphs demonstrating the analysis of citrated plasma samples from a third patient treated with an AAV2/8 viral vector in a phase 1/2 trial. The plasma sample obtained from the third patient was not FIX cross-reactive material positive (CRM+).

The results of this study are described below and in the figures. The FIX coagulation activity and the FIX antigen measurements were performed applying established standard methods; the citrated plasma samples were also subjected to specific measurement of FIX Padua protein with ELISA. The results of the FIX Padua ELISA, obtained in ng/mL, were transformed to activity and antigen units. In particular, the specific activity of the recombinant purified FIX Padua preparation of 2,310 IU FIX/mg, applied as assay standard for FIXp ELISA, was used to calculate activity units, while the transformation to antigen plasma units was based on the normal FIX plasma concentration of 5 µg/m L. FIGS. 26-29 demonstrate the assay selectivity, calibration curves, parallelism study in normal and FIX-deficient plasma and the influence of calcium on the sensitivity of ELISA, respectively Plasma samples were obtained from patients treated with an AAV2/8 viral vector. FIGS. 30-32 demonstrate activity and expression of FIX Padua in samples obtained from three patients. The plasma samples obtained from Subject 05-001 consistently demonstrated a FIX antigen concentration of close to 1 U/mL, but FIX activity below the lower limit of quantification. This data revealed the presence of FIX cross-reactive material (CRM+), i.e. coagulation-inactive FIX protein, measurable with a conventional FIX ELISA. The FIXp ELISA data paralleled the FIX activity data, demonstrating that the FIX activity measured was dependent on the expression of FIX Padua. In contrast, the FIX antigen concentrations measured with the FIX Padua-specific ELISA were clearly lower than those obtained with the standard ELISA, demonstrating that the FIX Padua ELISA allowed discrimination between CRM+ material and FIX Padua. Similar data, although at lower CRM+ levels, were found for the samples from Subject 10-005, while those from Subject 03-004 did not contain CRM+, resulting in parallel time-versus-concentration curves also for the two ELISA systems.

From these data, it was concluded that the FIX Padua-specific ELISA, based on using the highly specific Fab fragment for the capture of FIXp, allows additional monitoring of treatment outcome by the measurement of FIXp. These are the first data demonstrating the feasibility of this approach.

In the study described above, the following references are cited: [1] Simioni P, et al (2009): NEJM 361, 1671-1675. X-Linked thrombophilia with a Mutant Factor IX (Factor IX Padua); [2] Crudele J M, et al (2015). Blood 125:1553-1561. AAV liver expression of FIX-Padua prevents and eradicates FIX inhibitor without increasing thrombogenicity in hemophilia B dogs and mice.

Embodiments of the present specification may also be described as follows:
1. An antibody or antigen-binding fragment thereof that binds a Factor IX Padua comprising the amino acid sequence of SEQ ID NO: 1 and does not bind to a wild-type (WT) Factor IX comprising the amino acid sequence (SEQ ID NO: 2).
2. The antibody or antigen-binding fragment of embodiment 1, which binds an epitope of SEQ ID NO: 1, wherein the epitope is a linear epitope within the amino acid sequence DRATCLLSTKFT (SEQ ID NO: 3).
3. The antibody or antigen-binding fragment of embodiment 1, which binds to an epitope of SEQ ID NO: 1, wherein the epitope is a conformational epitope of the folded structure of the amino acid sequence LVDRATCLLSTKFTIYNNMFCAGFH (SEQ ID NO: 5).
4. The antibody or antigen-binding fragment of embodiment 1 or 3, wherein the folded structure comprises a disulfide bridge.
5. The antibody or antigen-binding fragment of any one of the previous embodiments, which does not bind to the amino acid sequence of DRATCLRSTKFT (SEQ ID NO: 14) or LVDRATCLRSTKFTIYNNMFCAGFH (SEQ ID NO:15).
6. The antibody or antigen-binding fragment of any one of the previous embodiments, wherein the antibody or antigen-binding fragment binds to the Factor IX Padua with a $K_D$ of about 100 nM or less.
7. The antibody or antigen-binding fragment of any one of the previous embodiments, wherein the antibody or antigen-binding fragment binds to the Factor IX Padua with a $K_D$ within a range of about 25 to about 75 nM.
8. The antibody or antigen-binding fragment of any one of the previous embodiments, wherein the antibody or antigen-binding fragment binds to the Factor IX Padua with a $K_D$ within a range of about 50 nM to about 60 nM.
9. The antibody or antigen-binding fragment of any one of the previous embodiments, wherein the antibody or antigen-binding fragment binds to the Factor IX Padua with a $K_D$ within a range of about 20 nM to about 100 nM, about 25 nM to about 95 nM, about 30 nM to about 90 nM, about 35 nM to about 85 nM, about 40 nM to about 80 nM, about 45 nM to about 75 nM, about 50 nM to about 70 nM, or about 55 nM to about 65 nM.
10. The antibody or antigen-binding fragment of any one of the previous embodiments, wherein the antibody or antigen-binding fragment binds to the Factor IX Padua and does not bind to a WT Factor IX in a sample comprising human plasma, optionally, wherein the sample comprises at least or about 5%, at least or about 10%, or at least or about 20% human plasma and the sample comprises at least or about 5 µg/mL WT Factor IX.
11. The antibody or antigen-binding fragment of any one of the previous embodiments, wherein the antibody or antigen-binding fragment does not bind to a Factor II polypeptide or a Factor X polypeptide.
12. The antibody or antigen-binding fragment of any one of the previous embodiments, wherein the antibody or antigen-binding fragment binds to neither Factor II nor Factor X.
13. The antibody or antigen-binding fragment of any one of the previous embodiments, which is a Fab or Fab2' antibody fragment.
14. The antibody or antigen-binding fragment of any one of the previous embodiments, which is monospecific.
15. The antibody or antigen-binding fragment of any one of the previous embodiments, which is fully human.
16. The antibody or antigen-binding fragment of any one of the previous embodiments, which is bivalent.
17. The antibody or antigen-binding fragment of any one of the previous embodiments, which is bivalent but monospecific for FIX Padua.
18. The antibody or antigen-binding fragment of any one of the previous embodiments, comprising dimerized Fab fragments or dimerized Fab mini antibody.
19. The antibody or antigen-binding fragment of any one of the previous embodiments, which is a dimerized Fab fragment via a linker.
20. The antibody or antigen-binding fragment of any one of the previous embodiments, comprising (i) the amino acid sequences of: SSYAIS (SEQ ID NO: 6); GIVPAFGTANYAQKFQG (SEQ ID NO: 7); SWGVISFAY (SEQ ID NO: 8); RASQDISSYLN (SEQ ID NO: 9); AASNLQS (SEQ ID NO: 10); and MQYDSLPFTF (SEQ ID NO: 11) or (ii) the amino acid sequence of SEQ ID NO: 24 or SEQ ID NO: 25 or SEQ ID NOs: 24 and 25 or (iii) the amino acid sequence of SEQ ID NO: 26 or SEQ ID NO: 27 or SEQ ID NOs: 26 and 27.
21. A polypeptide comprising an amino acid sequence comprising each of SEQ ID NOs: 6-11, optionally, wherein (i) one or more amino acids are present between each of SEQ ID NOs: 6-11, and/or (ii) the polypeptide optionally further comprises a FLAG tag comprising DYKDDDDK (SEQ ID NO: 12) and/or a hexa-His tag comprising HHHHHH (SEQ ID NO: 13).
22. The polypeptide of embodiment 21, wherein the FLAG tag and/or the hexa-His tag are located at the C-terminal end of the polypeptide.
23. A conjugate comprising the antibody or antigen-binding fragment or polypeptide of any one of the previous embodiments, conjugated to a heterologous moiety.
24. A conjugate of embodiment 23, wherein the heterologous moiety can be selected from the group consisting of: a polymer, a carbohydrate, a lipid, a nucleic acid, an oligonucleotide, an amino acid, peptide, polypeptide, protein and a detecting agent.
25. The conjugate of embodiment 23 or 24, wherein the antibody or antigen-binding fragment or polypeptide is conjugated to agarose, cellulose, dextran, polyacrylamide, latex or controlled pore glass.
26. The conjugate of any one of embodiments 23 to 25, wherein the antibody or antigen-binding fragment or polypeptide is conjugated to a fluorophore, chromophore, radioisotope, enzymatic label, or biotin.
27. The conjugate of any one of embodiments 23 to 26, comprising a homodimer of the polypeptide of embodiment 19.
28. The conjugate of any one of embodiment 27, wherein the polypeptides of the dimer are linked via a helix-turn-helix structure.
29. A nucleic acid comprising a nucleotide sequence encoding the antibody, antigen-binding fragment, polypeptide, conjugate, or a fragment thereof, of any one of the previous embodiments.
30. A vector comprising the nucleic acid of embodiment 29.
31. A host cell comprising the nucleic acid of embodiment 29 or the vector of embodiment 30.
32. A kit comprising the antibody or antigen-binding fragment of any one of embodiments 1 to 20, the polypeptide of embodiment 21 or 22, the conjugate of any one of embodiments 23 to 28, the nucleic acid of embodiment 29, the vector of embodiment 30, and/or the host cell of embodiment 31.
33. The kit of embodiment 32, further comprising a secondary antibody which binds to the antibody, antigen-binding fragment, polypeptide, or conjugate.
34. The kit of embodiment 32 or 33, further comprising a solid support.
35. The kit of any one of embodiments 32 to 34, wherein the antibody, antigen-binding fragment, polypeptide or conjugate is pre-coated on a solid support.
36. The kit of embodiment 34 or 35, wherein the solid support is a polymer bead, a microtiter plate, a membrane, or a filter.
37. The kit of embodiment 35 or 36, comprising a solid support pre-coated with a solution comprising about 100 ng or more, about 150 ng or more, about 200 ng or more, about 500 ng or more of the antigen binding fragment.
38. The kit of any one of embodiments 32 to 37, wherein the kit further comprises instructions for use.
39. A composition comprising an antibody or antigen-binding fragment thereof according to any one of embodiments 1 to 20 admixed with a biological sample obtained from a human comprising human plasma, or a diluted fraction thereof, and/or human tissue, or cells thereof, wherein, optionally, the composition comprises a detecting agent.
40. A composition comprising an antibody or antigen-binding fragment thereof according to any one of embodiments 1 to 20 admixed with a biological sample obtained from a human comprising human plasma proteins, wherein at least one of the human plasma proteins is selected from the group consisting of Factor IX, a variant of Factor IX, Factor II, a variant of Factor II, Factor X, and a variant of Factor X.
41. A composition of embodiment 40, wherein the composition comprises a detecting agent.
42. Use of the antibody or antigen-binding fragment of any one of embodiments 1 to 20, the polypeptide of embodiment 21 or 22, the conjugate of any one of embodiments 23 to 28, the nucleic acid of embodiment 29, the vector of embodiment 30, the host cell of embodiment 31, and/or the kit of any one of embodiments 32 to 38 for detecting Factor IX Padua in a sample.
43. A method of detecting Factor IX Padua in a sample obtained from a subject, comprising (i) contacting the sample with the antibody or antigen-binding fragment of any one of embodiments 1 to 20, the polypeptide of embodiment 21 or 22, or the conjugate of any one of embodiments 23 to 28 to form a complex comprising the Factor IX Padua and the antibody, antigen-binding fragment, polypeptide or conjugate, and (ii) detecting the complex in the sample.
44. The method of embodiment 43, wherein the antibody or antigen-binding fragment or polypeptide is conjugated to a detecting agent and/or a solid support or wherein the conjugate comprises a detecting agent.
45. The method of embodiment 43 or 44, comprising contacting the sample with a secondary antibody comprising a detecting agent, wherein the secondary antibody binds to the antibody or antigen-binding fragment or polypeptide or conjugate.
46. The method of any one of embodiments 43 to 35, wherein detecting the complex comprises detecting a signal of the detecting agent.
47. The method of embodiment 46, wherein the signal is an enzymatic activity, binding activity and/or chromogenic activity.
48. The method of any one of embodiments 43 to 47, wherein the sample is a blood sample, a serum sample, or a plasma sample.
49. The method of any one of embodiments 43 to 48, wherein the subject has been treated with a vector comprising a nucleotide sequence encoding Factor IX Padua.
50. A binding construct described herein.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. An antibody or antigen-binding fragment thereof that binds a Factor IX Padua comprising the amino acid sequence of SEQ ID NO: 1 and does not bind to a wild-type (WT) Factor IX comprising the amino acid sequence (SEQ ID NO: 2), wherein the antibody or antigen-binding fragment thereof comprises:
   (i) the amino acid sequences of: SSYAIS (SEQ ID NO: 6), GIVPAFGTANYAQKFQG (SEQ ID NO: 7), SWGV-ISFAY (SEQ ID NO: 8), RASQDISSYLN (SEQ ID NO: 9), AASNLQS (SEQ ID NO: 10), and MQYD-SLPFTF (SEQ ID NO: 11); or
   (ii) the amino acid sequences of SEQ ID NOs: 24 and 25; or
   (iii) the amino acid sequences of SEQ ID NOs: 26 and 27.

2. The antibody or antigen-binding fragment of claim 1, which binds an epitope of SEQ ID NO: 1, wherein the epitope is a linear epitope within the amino acid sequence DRATCLLSTKFT (SEQ ID NO: 3).

3. The antibody or antigen-binding fragment of claim 1, which binds to an epitope of SEQ ID NO: 1, wherein the epitope is a conformational epitope of the folded structure of the amino acid sequence LVDRATCLL-STKFTIYNNMFCAGFH (SEQ ID NO: 5), optionally, wherein the folded structure comprises a disulfide bridge.

4. The antibody or antigen-binding fragment of claim 1, which does not bind to the amino acid sequence of DRAT-CLRSTKFT (SEQ ID NO: 14) or LVDRAT-CLRSTKFTIYNNMFCAGFH (SEQ ID NO:15).

5. The antibody or antigen-binding fragment of claim 1, wherein the antibody or antigen-binding fragment binds to the Factor IX Padua with a $K_D$ of about 100 nM or less.

6. The antibody or antigen-binding fragment of claim 5, wherein the antibody or antigen-binding fragment binds to the Factor IX Padua with a $K_D$ within a range of about 25 to about 75 nM, optionally, wherein the antibody or antigen-binding fragment binds to the Factor IX Padua with a $K_D$ within a range of about 50 nM to about 60 nM.

7. The antibody or antigen-binding fragment of claim 1, wherein the antibody or antigen-binding fragment binds to the Factor IX Padua and does not bind to a WT Factor IX in a sample comprising human plasma, optionally, wherein the sample comprises at least or about 5%, at least or about 10%, or at least or about 20% human plasma and the sample comprises at least or about 5 µg/mL WT Factor IX.

8. The antibody or antigen-binding fragment of claim 1, wherein the antibody or antigen-binding fragment does not bind to a Factor II polypeptide or a Factor X polypeptide, optionally, wherein the antibody or antigen-binding fragment binds to neither Factor II nor Factor X.

9. The antibody or antigen-binding fragment of claim 1, which is a Fab or Fab2' antibody fragment.

10. The antibody or antigen-binding fragment of claim 1, which is monospecific.

11. The antibody or antigen-binding fragment of claim 1, which is fully human.

12. The antibody or antigen-binding fragment of claim 1, which is bivalent.

13. The antibody or antigen-binding fragment of claim 1, comprising dimerized Fab fragments or dimerized Fab mini antibody.

14. The antibody or antigen-binding fragment of claim 1, which is a dimerized Fab fragment via a linker.

15. An antibody or antigen-binding fragment comprising an amino acid sequence comprising each of SEQ ID NOs: 6-11, wherein the antibody or antigen-binding fragment binds a Factor IX Padua comprising the amino acid sequence of SEQ ID NO: 1 and does not bind to a wild-type (WT) Factor IX comprising the amino acid sequence (SEQ ID NO: 2), and optionally, wherein the antibody or antigen-binding fragment further comprises a FLAG tag comprising DYKDDDDK (SEQ ID NO: 12) and/or a hexa-His tag comprising HHHHHH (SEQ ID NO: 13), optionally, wherein the FLAG tag and/or the hexa-His tag are located at the C-terminal end of the antibody or antigen-binding fragment.

16. A conjugate comprising the antibody or antigen-binding fragment of claim 1, conjugated to a heterologous moiety, optionally selected from the group consisting of: a polymer, a carbohydrate, a lipid, a nucleic acid, an oligonucleotide, an amino acid, peptide, polypeptide, protein and a detecting agent.

17. The conjugate of claim 16, wherein the antibody or antigen-binding fragment is conjugated to agarose, cellulose, dextran, polyacrylamide, latex or controlled pore glass.

18. The conjugate of claim 16, wherein the antibody or antigen-binding fragment is conjugated to a fluorophore, chromophore, radioisotope, enzymatic label, or biotin.

19. The conjugate of claim 16, comprising a homodimer, which is a dimerized Fab fragment via a linker, optionally, wherein the polypeptides of the dimer are linked via a helix-turn-helix structure.

20. A nucleic acid comprising a nucleotide sequence encoding the antibody or antigen-binding fragment of claim 1.

21. A vector comprising the nucleic acid of claim 20.

22. A host cell comprising the nucleic acid of claim 20.

23. A kit comprising (i) the antibody or antigen-binding fragment of claim 1, and optionally, instructions for use, and optionally, (ii) a secondary antibody which binds to the antibody or antigen-binding fragment of (i).

24. The kit of claim 23, further comprising a solid support.

25. The kit of claim 24, wherein the antibody or antigen-binding fragment is pre-coated on the solid support.

26. The kit of claim 24, wherein the solid support is a polymer bead, a microtiter plate, a membrane, or a filter.

27. The kit of claim 26, comprising a solid support pre-coated with a solution comprising about 50 ng to about 500 ng of the antibody or antigen binding fragment.

28. A composition comprising an antibody or antigen-binding fragment of claim 1 admixed with a biological sample obtained from a human comprising human plasma, or a diluted fraction thereof, and/or human tissue, or cells thereof, wherein, optionally, the composition comprises a detecting agent.

29. A composition comprising an antibody or antigen-binding fragment of claim 1 admixed with a biological sample obtained from a human comprising human plasma proteins, wherein at least one of the human plasma proteins is selected from the group consisting of Factor IX, or a variant thereof, Factor II, and Factor X, wherein, optionally, the composition comprises a detecting agent.

30. A method of detecting Factor IX Padua in a sample obtained from a subject, comprising (i) contacting the sample with the antibody or antigen-binding fragment of claim 1 to form a complex comprising the Factor IX Padua and the antibody or antigen-binding fragment, and (ii) detecting the complex in the sample.

31. The method of claim 30, wherein the antibody or antigen-binding fragment is conjugated to a detecting agent and/or a solid support.

32. The method of claim 30, comprising contacting the sample with a secondary antibody comprising a detecting agent, wherein the secondary antibody binds to the antibody or antigen-binding fragment.

33. The method of claim 31, wherein detecting the complex comprises detecting a signal of the detecting agent.

34. The method of claim 33, wherein the signal is an enzymatic activity, binding activity and/or chromogenic activity.

35. The method of claim 30, wherein the sample is a blood sample, a serum sample, or a plasma sample.

36. The method of claim 30, wherein the subject has been treated with a vector comprising a nucleotide sequence encoding Factor IX Padua.

37. A method of detecting Factor IX Padua in a sample obtained from a subject, comprising (i) contacting the sample with the antibody or antigen-binding fragment of claim 15 to form a complex comprising the Factor IX Padua and the antibody or antigen-binding fragment, and (ii) detecting the complex in the sample.

38. The method of claim 33, wherein the antibody or antigen-binding fragment is conjugated to a detecting agent and/or a solid support.

39. The method of claim 33, comprising contacting the sample with a secondary antibody comprising a detecting agent, wherein the secondary antibody binds to the antibody or antigen-binding fragment.

40. The method of claim 38, wherein detecting the complex comprises detecting a signal of the detecting agent.

41. The method of claim 40, wherein the signal is an enzymatic activity, binding activity and/or chromogenic activity.

42. The method of claim 33, wherein the sample is a blood sample, a serum sample, or a plasma sample.

43. The method of claim 33, wherein the subject has been treated with a vector comprising a nucleotide sequence encoding Factor IX Padua.

44. A method of detecting Factor IX Padua in a sample obtained from a subject, comprising (i) contacting the sample with the conjugate of claim 16 to form a complex comprising the Factor IX Padua and the conjugate, and (ii) detecting the complex in the sample.

45. The method of claim 44, wherein the conjugate comprises a detecting agent.

46. The method of claim 44, comprising contacting the sample with a secondary antibody comprising a detecting agent, wherein the secondary antibody binds to the conjugate.

47. The method of claim 45, wherein detecting the complex comprises detecting a signal of the detecting agent.

48. The method of claim 47, wherein the signal is an enzymatic activity, binding activity and/or chromogenic activity.

49. The method of claim 44, wherein the sample is a blood sample, a serum sample, or a plasma sample.

50. The method of claim 44, wherein the subject has been treated with a vector comprising a nucleotide sequence encoding Factor IX Padua.

51. A kit comprising (i) the antibody or antigen-binding fragment of claim 15, and optionally, instructions for use, and optionally, (ii) a secondary antibody which binds to the antibody or antigen-binding fragment of (i).

52. A kit comprising (i) the conjugate of claim 16, and optionally, instructions for use, and optionally, (ii) a secondary antibody which binds to the conjugate of (i).

* * * * *